(12) United States Patent
Littlejohn et al.

(10) Patent No.: US 10,779,518 B2
(45) Date of Patent: Sep. 22, 2020

(54) GENETIC MARKERS AND USES THEREFOR

(71) Applicant: Livestock Improvement Corporation Limited, Hamilton (NZ)

(72) Inventors: Mathew Douglas Littlejohn, Auckland (NZ); Stephen Richard Davis, Hamilton (NZ)

(73) Assignee: Livestock Improvement Corporation Limited, Hamilton (NZ)

( * ) Notice: Subject to any disclaimer, the term of this patent is extended or adjusted under 35 U.S.C. 154(b) by 698 days.

(21) Appl. No.: 15/029,124

(22) PCT Filed: Oct. 24, 2014

(86) PCT No.: PCT/NZ2014/000224
§ 371 (c)(1),
(2) Date: Apr. 13, 2016

(87) PCT Pub. No.: WO2015/060732
PCT Pub. Date: Apr. 30, 2015

(65) Prior Publication Data
US 2016/0262360 A1 Sep. 15, 2016

(30) Foreign Application Priority Data

Oct. 25, 2013 (NZ) ........................................ 617040
May 20, 2014 (NZ) ........................................ 625150
Jul. 8, 2014 (NZ) ........................................ 627209
Sep. 12, 2014 (NZ) ........................................ 630540

(51) Int. Cl.
*C12Q 1/68* (2018.01)
*A01K 67/027* (2006.01)
*C12Q 1/6876* (2018.01)
*C07K 14/72* (2006.01)

(52) U.S. Cl.
CPC ........ *A01K 67/027* (2013.01); *A01K 67/0273* (2013.01); *C07K 14/72* (2013.01); *C12Q 1/6876* (2013.01); *A01K 2227/101* (2013.01); *C12Q 2600/124* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 4,873,191 A | 10/1989 | Wagner et al. |
| 5,142,047 A | 8/1992 | Summerton et al. |
| 5,185,444 A | 2/1993 | Summerton et al. |
| 5,763,240 A | 6/1998 | Zarling et al. |
| 5,948,653 A | 9/1999 | Pati et al. |
| 6,169,172 B1 | 1/2001 | Devauchelle et al. |
| 6,613,752 B2 | 9/2003 | Kay et al. |
| 7,199,281 B2 | 4/2007 | Murray et al. |
| 7,361,641 B2 | 4/2008 | Calos |
| 8,586,526 B2 | 11/2013 | Gregory et al. |
| 2002/0160372 A1 | 10/2002 | Rothschild et al. |
| 2003/0232410 A1 | 12/2003 | Liljedahl et al. |
| 2005/0003542 A1 | 1/2005 | Kay et al. |
| 2005/0014166 A1 | 1/2005 | Trono et al. |
| 2010/0105140 A1 | 4/2010 | Fahrenkrug et al. |
| 2010/0138939 A1 | 6/2010 | Bentzon et al. |
| 2010/0146655 A1 | 6/2010 | Fahrenkrug et al. |
| 2011/0023140 A1 | 1/2011 | Bedell et al. |
| 2011/0059160 A1 | 3/2011 | Essner et al. |
| 2011/0197290 A1 | 8/2011 | Fahrenkrug et al. |
| 2011/0201118 A1 | 8/2011 | Yang et al. |
| 2011/0207221 A1 | 8/2011 | Cost et al. |
| 2011/0287545 A1 | 11/2011 | Cost et al. |
| 2011/0301073 A1 | 12/2011 | Gregory et al. |
| 2012/0117870 A1 | 5/2012 | Ness et al. |
| 2012/0149115 A1 | 6/2012 | Kim et al. |
| 2012/0196370 A1 | 8/2012 | Urnov et al. |
| 2012/0198878 A1 | 8/2012 | Pellegrini et al. |
| 2012/0212722 A1 | 8/2012 | Smith et al. |
| 2012/0222143 A1 | 8/2012 | Fahrenkrug et al. |
| 2013/0212723 A1 | 8/2013 | West |
| 2013/0212725 A1 | 8/2013 | Kühn et al. |
| 2013/0217131 A1 | 8/2013 | Kim et al. |
| 2013/0298268 A1 | 11/2013 | West |
| 2013/0326645 A1 | 12/2013 | Cost et al. |

(Continued)

FOREIGN PATENT DOCUMENTS

| | | |
|---|---|---|
| JP | 2009-225807 A | 10/2009 |
| NZ | 565337 A | 1/2007 |

(Continued)

OTHER PUBLICATIONS

Collins, Complete Field Guide to American Wildlife, Harper & Row, New York, 1959, pp. 77, 335, and 339.*
AgGenetics Investor Webinar, PDF presentation from Feb. 2016, (print of webpage), download information retrieved from https://agfunderweb.s3.amazonaws.com/slides/AgGenetics/AgGenetics%20Company%20Overview_February%202016.pdf, 1 page.
Alamer, "The Role of Prolactin in Thermoregulation and Water Balance During Heat Stress in Domestic Ruminants," *Asian Journal of Animal and Veterinary Advances* 6(12):1153-1169, 2011.
Alexander et al., "A Limousin specific myostatin allele affects longissimus muscle are and fatty acid profiles in a Wagyu-Limousin $F_2$ population," *J. Anim.* Sci 87:1576-1581, 2009.
Anders et al., "Differential expression analysis for sequence count data," *Genome Biology* 11:R106, 2010, 12 pages.

(Continued)

*Primary Examiner* — James Martinell
(74) *Attorney, Agent, or Firm* — Seed IP Law Group LLP

(57) ABSTRACT

The present invention relates, inter alia, to methods for determining whether or not an animal and/or its offspring is more likely than not to have an increased tolerance to heat, an increased resistance to ticks, and/or a desirable coat texture. It also provides methods for selecting or rejecting animals, one or more cells or embryos, estimating the worth of an animal, generating animals having a desired genotype/phenotype, cloning and breeding animals and herd formation.

22 Claims, 5 Drawing Sheets
Specification includes a Sequence Listing.

(56) References Cited

U.S. PATENT DOCUMENTS

| | | |
|---|---|---|
| 2014/0041066 A1 | 2/2014 | Carlson et al. |
| 2014/0120612 A1 | 5/2014 | Doyon et al. |
| 2015/0018604 A1 | 1/2015 | West et al. |
| 2015/0064149 A1 | 3/2015 | West et al. |
| 2015/0067898 A1 | 3/2015 | Fahrenkrug et al. |
| 2015/0156996 A1 | 6/2015 | Fahrenkrug et al. |
| 2015/0320019 A1 | 11/2015 | West |
| 2016/0044901 A1 | 2/2016 | West |
| 2016/0081313 A1 | 3/2016 | West |

FOREIGN PATENT DOCUMENTS

| | | |
|---|---|---|
| NZ | 598457 A | 6/2014 |
| NZ | 598457 B | 6/2014 |
| WO | 98/03682 A1 | 1/1998 |
| WO | 2007/070965 A1 | 6/2007 |
| WO | 2009/045289 A2 | 4/2009 |
| WO | 2010/079430 A1 | 7/2010 |
| WO | 2011/017315 A3 | 2/2011 |
| WO | 2011/019385 A1 | 2/2011 |
| WO | 2011/028134 A1 | 3/2011 |
| WO | 2011/072246 A3 | 6/2011 |
| WO | 2011/146121 A1 | 11/2011 |
| WO | 2011/154393 A1 | 12/2011 |
| WO | 2012/012738 A1 | 1/2012 |
| WO | 2012/116274 A3 | 8/2012 |
| WO | 2012/152912 A1 | 11/2012 |
| WO | 2012/168304 A1 | 12/2012 |
| WO | 2012/168307 A3 | 12/2012 |
| WO | 2013/088446 A1 | 6/2013 |
| WO | 2013/123365 A1 | 8/2013 |
| WO | 2013/191769 A1 | 12/2013 |
| WO | 2013/192316 A1 | 12/2013 |
| WO | 2014/189680 A1 | 1/2014 |
| WO | 2014/022120 A1 | 2/2014 |
| WO | 2014/070887 A1 | 5/2014 |
| WO | 2014/110552 A1 | 7/2014 |
| WO | 2014/145196 A3 | 9/2014 |
| WO | 2014/193583 A2 | 12/2014 |
| WO | 2014/193584 A2 | 12/2014 |
| WO | 2015/009571 A1 | 1/2015 |
| WO | 2015/030881 A1 | 3/2015 |
| WO | 2015/035034 A1 | 3/2015 |
| WO | 2016/049182 A1 | 3/2016 |

OTHER PUBLICATIONS

Bailey, "Heat Stress Consequences and Mechanics Presentation," retrieved from https://ecommons.cornell.edu/handle/1813/36554, 2011, 6 pages.

Bedell et al., "In vivo genome editing using a high-efficiency TALEN system," Nature 491:114-120, 2012.

Ben-Jonathan, "Extrapituitary Prolactin: Distribution, Regulation, Functions, and Clinical Aspects," Endocrine Reviews 17(6):639-669, 1996.

Blok et al., "Growth hormone substitution in adult growth hormone-deficient men augments androgen effects on the skin," Clinical Endocrinology 47:29-36, 1997.

Bocchinfuso et al., "Induction of Mammary Gland Development in Estrogen Receptor-α Knockout Mice," Endocrinology 141(8):2982-2994, 2000.

Brisken et al., "Prolactin Controls Mammary Gland Development via Direct and Indirect Mechanisms," Developmental Biology 210:96-106, 1999.

Browning et al., "A Unified Approach to Genotype Imputation and Haplotype-Phase Inference for Large Data Sets of Trios and Unrelated Individuals," The American Journal of Human Genetics 84:210-223, 2009.

Bu et al., Characterization of the novel duplicated PRLR gene at the late-feathering K locus in Lohmann Chickens, Journal of Molecular Endocrinology 51(2):261-276, 2013.

Business Wire, A Berkshire Hathaway Company, "Chromatin Transfer Promises to Improve Survival, Efficiency in Cattle Cloning, Journal Reports," 2003, 2 pages.

Carbery et al., "Targeted Genome Modification in Mice Using Zinc-Finger Nucleases," Genetics 186:451-459, 2010.

Carlson et al., "Adding and subtracting livestock genes with transposons and nucleases," Transgenic Res 21(4):901-925, 2012, (Abstract). (2 pages).

Carlson et al., "Strategies for selection marker-free swine transgenesis using the Sleeping Beauty transposon system," Transgenic Res 20:1125-1137, 2011.

Carlson et al., "Efficient TALEN-mediated gene knockout in livestock," PNAS 109(43):17382-17387, 2012.

Carlson et al., "Editing livestock genomes with site-specific nucleases," Reproduction, Fertility and Development 26:74-82, 2014.

Carlson et al., "Control of Sexual Maturation in Animals," U.S. Appl. No. 61/720,187, filed Oct. 30, 2012, 56 pages.

Carvalho et al., "Breed Affects Thermoregulation and Epithelial Morphology in Imported and Native Cattle Subjected to Heat Stress," J. Anim. Sci. 73:3570-3573, 1995.

Casas et al., "Quantitative trait loci affecting growth and carcass composition of cattle segregating alternate forms of myostatin," J. Anim. Sci. 78:560-569, 2000.

Cermak et al., "Efficient design and assembly of custom TALEN and other TAL effector-based constructs for DNA targeting," Nucleic Acids Research 39(12): e82, 2011, 11 pages.

Chang et al., "Androgen Receptor (AR) Physiological Roles in Male and Female Reproductive Systems: Lesson Learned from AR-Knockout Mice Lacking AR in Selective Cells," Biology of Reproduction 89(1):1-16, 2013.

Chase Jr. et al., "A Microsatellite Based Test for Slick Hair Phenotype in Senepol-Derived Cattle," Plant & Animal Genomes XV Conference, Jan. 13-17, 2007, 2 pages (Abstract P548: Cattle).

Christian et al., "Targeting DNA Double-Strand Breaks with TAL Effector Nucleases," Genetics 186:757-761, 2010.

Cingolani et al., "A program for annotating and predicting the effects of single nucleotide polymorphisms, SnpEff: SNPs in the genome of Drosophila melanogaster strain $w^{1118}$; iso-2; iso-3," Fly 6(2):80-92, 2012.

Clark et al., "Enzymatic engineering of the porcine genome with transposons and recombinases," BMC Biotechnology 7(42): 2007, 17 pages.

Cleary et al., "Joint Variant and De Novo Mutation Identification on Pedigrees from High-Throughput Sequencing Data," Journal of Computational Biology 21(6):405-419, 2014.

Craven et al., "Prolactin Signaling Influences the Timing Mechanism of the Hair Follicle: Analysis of Hair Growth Cycles in Prolactin Receptor Knockout Mice," Endocrinology 142(6):2533-2539, 2001.

Davis, "Genetic Parameters for Tropical Beef Cattle in Northern Australia: a Review," Aust. J. Agric. Res. 44:179-198, 1993.

Davis, "Genome Editing: Which Should I Choose, TALEN or CRISPR?," 2014, retrieved from http://www.genecopoeia.com/resource/genome-editing-talen-or-crisp/, retrieved on Sep. 30, 2016, 4 pages.

DePristo et al., "A framework for variation discovery and genotyping using next-generation DNA sequencing data," Nature Genetics 43:491-498, 2011.

Dikmen et al., "The SLICK hair locus derived from Senepol cattle confers thermotolerance to intensively managed lactating Holstein cows," J. Dairy Sci. 97:5508-5520, 2014.

Dikmen at al., "Differences in Thermoregulatory Ability Between Slick-Haired and Wild-Type Lactating Holstein Cows in Response to Acute Heat Stress," J. Dairy Sci. 91:3395-3402, 2008.

Dong et al., "Heritable Targeted Inactivation of Myostatin Gene in Yellow Catfish (Pelteobagrus fulvidraco) Using Engineered Zinc Finger Nucleases," PLoS ONE 6(12): e28897, 2011, 7 pages.

Doyon et al., "Heritable Targeted Gene Disruption in Zebrafish Using Designed Zinc Finger Nucleases," Nat Biotechnol. 26(6):702-708, 2008. (18 pages).

Endo et al., "CIS1 Interacts with the Y532 of the Prolactin Receptor and Suppresses Prolactin-Dependent STAT5 Activation," J. Biochem. 133:109-113, 2003.

(56) References Cited

OTHER PUBLICATIONS

Fahrenkrug et al., "Gene Inactivation and Nonmeiotic Allele Introgression in Livestock Species Using TALENs," *Reproduction, Fertility and Development* 25:318, 2012 (Abstract). (5 pages).

Fahrenkrug et al., "337 Nonmeiotic Introgression of Quantitative Trait Nucleotides and Correction of Congenital Mutations in Livestock with Transcription Activator-like Effector Nucleases," *Reproduction, Fertility and Development* 25:316, 2012 (Abstract). (5 pages).

Fahrenkrug, "Molecular breeding to accelerate livestock improvement," 2014 Beef Improvement Federation Research Symposium & Annual Meeting, retrieved from http://www.bifconference.com/bif2014/newsroom.html on Oct. 27, 2016, 10 pages.

Fahrenkrug et al., "95 Production of Gene-Edited Pigs, Cattle, and Lambs by Embryo Injection of TALENS or ZFNs," *Reproduction, Fertility and Development*, 26(1):161, 2013 (Abstract).

Fahrenkrug et al., "Methods and Compositions for Targeted Gene Modification," U.S. Appl. No. 61/441,651, filed Feb. 25, 2011, 48 pages.

Fahrenkrug et al., "Genetically Modified Animals and Methods for Making the Same," U.S. Appl. No. 61,662,767, filed Jun. 21, 2012, 90 pages.

Fahrenkrug et al., "Production of FMDV-Resistant Livestock by Allele Substitution," U.S. Appl. No. 61/677,904, filed Jul. 31, 2012, 8 pages.

Fahrenkrug et al., "Hornless Livestock," U.S. Appl. No. 61/752,232, filed Jan. 14, 2013, 126 pages.

Fahrenkrug et al., "Efficient Non-Meiotic Allele Intogression in Livestock," U.S. Appl. No. 61/870,401, filed Aug. 27, 2013, 79 pages.

Fahrenkrug et al., "Control of Sexual Maturation in Animals," U.S. Appl. No. 61/870,510, filed Aug. 27, 2013, 107 pages.

Fahrenkrug et al., "Hornless Livestock," U.S. Appl. No. 61/870,570, filed Aug. 27, 2013, 140 pages.

Farzadfard et al., "Tunable and Multifunctional Eukaryotic Transcription Factors Based on CRISPR/Cas," *ACS Synth. Biol.* 2:604-613, 2013.

Ferguson et al., "The Function of Cattle Sweat Glands," *Aust. J. Agric. Res.* 6:640-644, 1955.

Flori et al., "A Quasi-Exclusive European Ancestry in the Senepol Tropical Cattle Breed Highlights in Importance of the slick Locus in Tropical Adaptation," *PLoS ONE* 7(5): e36133, 2012, 10 pages.

Foitzik et al., "Prolactin and the Skin: A Dermatological Perspective on an Ancient Pleiotropic Peptide Hormone," *Journal of Investigative Dermatology* 129:1071-1087, 2009.

Foitzik et al., "Human Scalp Hair Follicles Are Both a Target and a Source of Prolactin, which Serves as an Autocrine and/or Paracrine Promoter of Apoptosis-Driven Hair Follicle Regression," *American Journal of Pathology* 168(3):748-756, 2006.

Gaj et al., "ZFN, TALEN, and CRISPR/Cas-based methods for genome engineering," *Trends in Biotechnology* 31(7):397-405, 2013.

Garcia et al., "Precision Breeding to Improve Tropical Cattle: Increasing Production and Quality," Livestock Industry Conference on Genetics, 2015, 68 pages.

Gasparin et al.,"Mapping of quantitative trait loci controlling tick[*Riphocephalus (Boophilus) microplus*] resistance on bovine chromosomes 5, 7 and 14," *Animal Genetics* 38:453-459, 2007.

GenBank Accession No. AF027403.1, Nov. 8, Schuler et al., "Bos Taurus prolactin receptor short form mRNA, complete cds," 1997, 2 pages.

GenBank Accession No. NM_001039726.2, Jul. 15, 2012, Lu et al., "Bos Taurus prolactin receptor (PRLR), transcript variant 2, mRNA," retrieved Feb. 9, 2014, 3 pages.

GenBank Accession No. EE958171.1, Lehnert, "K21350A FNM Bos Taurus cDNA clone K21355-, mRNA sequence," Dec. 10, 2006, 2 pages.

GenBank Accession No. BM89500.1, "503266 MARC 2BOV Bos Taurus cDNA 5-, mRNA sequence," Nov. 19, 2001, 2 pages.

GenBank Accession No. FJ901281.1, Jul. 24, 2016, Iso-Touru et al., "Bos indicus haplotype Bos_PRLR4 prolactin receptor (PRLR) gene, exon 10 and partial cds," retrieved Sep. 30, 2016, 1 page.

GenBank Accession No. FJ901295.1, Iso-Touru et al., "Bos grunniens haplotype BOSgr_PRLR1 prolactin receptor (PRLR) gene, exon 10 and partial cds," Jul. 24, 2016, 1 page.

GenBank Accession No. NM_001039726.1, Feb. 9, 2014, Lu et al., "Bos Taurus prolactin receptor (PRLR), transcript variant 2, mRNA," retrieved Jul. 15, 2012, 3 pages.

GenBank Accession No. NM_174155.2, Lu et al., "Bos taurus prolactin receptor (PRLR), transcript variant 1, mRNA," Jul. 15, 2012, 3 pages.

GenBank, "PREDICTED: Bos Taurus prolactin receptor (PRLR), transcript variant X3, mRNA," Accession No. XM_005221577.1, Aug. 5, 2013, 4 pages.

GenBank Accession No. NP_001034815.1, Dec. 25, 2015, Pratt et al., "prolactin receptor long form precursor [Bos Taurus]," retrieved Dec. 25, 2015, 3 pages.

GenBank Accession No. AC_000177.1, Zimin et al., "Bos Taurus breed Hereford chromosome 20, Bos_taurus_UMD_3.1.1, whole genome shotgun sequence," Jan. 26, 2016, 41 pages.

Geurts et al., "Knockout Rats via Embryo Microinjection of Zinc-Finger Nucleases," *Science* 325:433, 2009.

Gill et al., "AGGenetics—Meeting Agricultural Demands in a Socially Responsible Way," Company Overview, Feb. 2016, 25 pages.

Hammond et al., "Heat Tolerance in Two Tropically Adapted Bos taurus Breeds, Senepol and Romosinuano, Compared with Brahman, Angus, and Hereford Cattle in Florida," *Journal of Animal Science* 74:295-303, 1996.

Hauschild et al., "Efficient generation of a biallelic knockout in pigs using zinc-finger nucleases," *PNAS* 108(36):12013-12017, 2011.

High, "The Moving Finger," *Nature* 435:577-578, 1997.

Horseman et al., "Defective mammopoiesis, but normal hematopoiesis, in mice with a targeted disruption of the prolactin gene," *The EMBO Journal* 16(23):6926-6935, 1997.

Huang et al., "Interactions of the bovine placental lactogen and prolactin receptor genes are associated with fertility traits in cattle," *Animal* 3(12):1743-1745, 2009.

Huang et al., "Heritable gene targeting in zebrafish using customized TALENs," *Nature Biotechnology* 29(8):699-700, 2011.

Hüe et al., "Comparison of tick resistance of crossbred Senepol'Limousin to purebred Limousin cattle," *Trop Anim Health Prod* 46:447-453, 2014.

Huson et al., "Genome-wide association study and ancestral origins of the slick-hair coat in tropically adapted cattle," *Frontiers in Genetics* 5: 2014, 12 pages.

Ibelli et al., "Resistance of cattle of various genetic groups to the tick *Rhipicephalus microplus* and the relationship with coat traits," *Veterinary Parasitology* 186:425-430, 2012.

Iso-Touru et al., "Divergent evolution in the cytoplasmic domains of PRLR and GHR genes in Artiodactyla," *BMC Evolutionary Biology* 9(172): 2009, 11 pages.

Jinek et al., "RNA-programmed genome editing in human cells," *eLife*, 9 pages, 2013.

Kaufman, "Androgen Metabolism as it Affects Hair Growth in Androgenetic Alopecia," *Dermatologic Clinics* 14(4):697-711, 1996.

Kawakami, "Tol2: a versatile gene transfer vector in vertebrates," *Genome Biology* 8(Suppl. I): S7.1-S7.10, 2007.

Kim et al., "A guide to genome engineering with programmable nucleases," *Nature Reviews Genetics* 15:321-334, 2014.

Kim et al., "TopHat2: accurate alignment of transcriptomes in the presence of insertions, deletions and gene fusions," *Genome Biology* 14(R3 6): 2013, 13 pages.

Kleinberg, "Early Mammary Development: Growth Hormone and IGF-1," *Journal of Mammary Gland Biology and Neoplasia* 2(1):49-57, 1997.

Kondo et al., "Organ culture of human scalp hair follicles: effect of testosterone and oestrogen on hair growth," *Archives of Dermatological Research*, 282:442-445, 1990.

Larson, "The Experiment—The birth of twin monkeys whose DNA was altered with the new genome-editing tool CRISPR proves it's

(56) References Cited

OTHER PUBLICATIONS possible to create primates with precise genetic mutations," *MIT Technology Review* 117(3):27-37, 2014.
Li et al., "Fast and accurate short read alignment with Burrows-Wheeler transform," *Bioinformatics* 25(14):1754-1760, 2009.
Li et al., "In vivo genome editing restores haemostasis in a mouse model of haemophilia," *Nature* 475:217-223, 2011.
Lillico et al., "Live pigs produced from genome edited zygotes," *Scientific Reports* 3(2847), 2013, 4 pages.
Lü et al., "Novel SNPs of the Bovine PRLR Gene Associated with Milk Production Traits," *Biochemical Genetics* 49:177-189, 2011.
Lü et al., "Single nucleotide polymorphisms of the prolactin receptor (PRLR) gene and its association with growth traits in chinese cattle," *Mol Biol Rep* 38:261-266, 2011.
Ma et al., "High Efficiency In Vivo Genome Engineering with a Simplified 15-RVD GoldyTALEN Design," *PLoS ONE* 8(5): e65259, 2013, 8 pages.
Mariasegaram et al., "The slick hair coat locus maps to chromosome 20 in Senepol-derived cattle," *Animal Genetics* 38, 54-59, 2007.
Meng et al., "Targeted gene inactivation in zebrafish using engineered zinc finger nucleases," *Nat Biotechnol.* 26(6):695-701, 2008. (17 pages).
Miller et al., "A TALE nuclease architecture for efficient genome editing," *Nature Biotechnology* 29(2):143-150, 2011.
Mills et al., "Response of Plasma Prolactin to Changes in Ambient Temperature and Humidity in Man," *Journal of Clinical Endocrinology and Metabolism* 52(2):279-283, 1981.
Miskey et al., "The Ancient mariner Sails Again: Transposition of the Human *Hsmar 1* Element by a Reconstructed Transposase and Activities of the SETMAR Protein on Transposon Ends," *Molecular and Cellular Biology* 27(12):4589-4600, 2007.
Miskey et al., "The Frog Prince: a reconstructed transposon from Rana pipiens with high transpositional activity in vertebrate cells," *Nucleic Acids Research* 31(24)6873-6881, 2003.
Mussolino et al., "A novel TALE nuclease scaffold enables high genome editing activity in combination with low toxicity," *Nucleic Acids Research* 39(21):9283-9293, 2011.
NCBI "PRLR prolactin receptor [*Bos taurus* (cattle)]" Gene ID 281422, updated Aug. 8, 2016, 8 pages.
Oftedal et al., "Evo-Devo of the Mammary Gland," *J Mammary Gland Biol Neoplasia* 18:105-120, 2013.
Oftedal et al., "The Mammary Gland and Its Origin During Synapsid Evolution," *Journal of Mammary Gland Biology and Neoplasia* 7(3):225-252, 2002.
Oh et al., "An estrogen receptor pathway regulates the telogen-anagen hair follicle transition and influences epidermal cell proliferation," *Proc. Natl. Acad. Sci* 93:12525-12530, 1996.
Olson et al., "Evidence of a major gene influencing hair length and heat tolerance in *Bos taurus* cattle," *Journal of Animal Science* 81:80-90, 2003.
Pavlapoulos et al., "The DNA transposon Minos as a tool for transgenesis and functional genomic analysis in vertebrate and invertebrates," *Genome Biology* 8(Suppl I):S2.1-S2.7, 2007.
Peippo et al., "Birth of Correctly Genotyped Calves After Multiplex Marker Detection From Bovine Embryo Microblade Biopsies," *Molecular Reproduction and Development* 74:1373-1378, 2007.
Porteus et al., "Gene targeting using zinc finger nucleases," *Nature Biotechnology* 23(8): 967-973, 2005.

Proudfoot et al., "Genome edited sheep and cattle," *Transgenic Res* 24:147-153, 2015.
Purcell et al., "PLINK: A Tool Set for Whole-Genome Association and Population-Based Linkage Analysis," *The American Journal of Human Genetics* 81:559-575, 2007.
Purchas et al., "Composition and quality differences between the longissimus and infraspinatus muscles for several groups of pasture-finished cattle," *Meat Science* 80:470-479, 2008.
Ramirez et al., "Unexpected failure rates for modular assembly of engineered zinc fingers," *Nature Methods*, 5(5):374-375, 2008.
Sander et al., "Engineering Zinc Finger Nucleases for Targeted Mutagenesis of Zebrafish," *Methods in Cell Biology* 104:51-58, 2011.
Shen, "CRISPR technology leaps from lab to industry," Dec. 3, 2013, retrieved from http://www.nature.com/news/crispr-technology-leaps-from-lab-to-industry-1.14299, retrieved on Oct. 3, 2016, 4 pages.
Sonstegard, "Applied Genomics in Cattle-Identification of the SLICK locus in tropically adapted cattle," SBCA Convention 2013, Bogota, Columbia, 2013, 57 pages.
Sonstegard et al., "The identification of a putative mutation for SLICK hair coat in Senepol cattle," Jul. 23, 2014, retrieved from http://asas.comfex.xom/asas/jam2014/webprogram/Paper8373.html, retrieved on Aug. 13, 2015, 4 pages.
Spencer, "'Jaw Dropping' new form of gene therapy could allow scientists to modify human DNA and transform treatment of incurable genetic diseases," *Daily Mail*, Oct. 3, 2016, 22 pages.
Stenn et al., "Controls of Hair Follicle Cycling," *Physiological Reviews* 81(1):449-494, 2001.
Tan et al., "Efficient nonmeiotic allele introgression in livestock using custom endonucleases," *PNAS* 110(41)16526-16531, 2013.
Tan et al., "Efficient non-meiotic allele introgression in livestock using TAL effector nucleases and the CRISPR-cas9 system," *Transgenic Research* 23:187-210, 2014 (Abstract). (1 page).
Tan et al., "Gene targeting of the swine myostatin gene using rAAV and TALENs," *Transgenic Research* 21:901-925, 2012. (1 page).
Tan, "Genome Engineering in Large Animals for Agricultural and Biomedical Applications," A Dissertation Submitted to the Faculty of University of Minnesota, 2013, 235 pages.
Tan et al., "Precision Editing of Large Animal Genomes," *Adv Genet.* 80:37-97, 2012.
Tesson et al., "Knockout rats generated by embryo microinjection of TALENs," *Nature Biotechnology* 29(8):695-696, 2011.
Turner et al., "A genome-wide association study of tick burden and milk composition in cattle," *Animal Production Science* 50:235-245, 2010.
Viitala et al., "The Role of the Bovine Growth Hormone Receptor and Prolactin Receptor Genes in Milk, Fat and Protein Production in Finnish Ayrshire Dairy Cattle," *Genetics* 173:2151-2164, 2006.
Wells, "Natural genotypes via genetic engineering," *PNAS* 110(41):16295-16296, 2013.
West, "Materials and Methods for Producing Animals With Short Hair," U.S. Appl. No. 62/054,169, filed Sep. 23, 2014, 26 pages.
Written Opinion of the International Searching Authority, dated Dec. 30, 2015, for International Application No. PCT/US2015/051717, 6 pages.
Dunshea et al., "Amelioration of thermal stress impacts in dairy cows," *Animal Production Science* 53:965-975, 2013.
NCBI, "Prolactin Receptor [*Bos taurus*]," GenBank Accession No. AAA51417.1, 1994. 2 pages.

\* cited by examiner

Figure 1

SEQ ID No. 4:
NCBI Reference Sequence: NM_001039726.2 Bos taurus prolactin receptor (PRLR) mRNA
Base deleted (at 39136559 on BTA20) in Senepol PRLR (c) is indicated.

```
ORIGIN
        1 ggcaaatgct gaggatactt tccaagtgaa ccctgagtga acctctaata tatttatttc
       61 ctgtggaaag aggaaggagc caacatgaag gaaaatgcag catctagagt ggttttcatt
      121 ttgctacttt ttctcagtgt cagccttctg aatggacagt cacctcctga aaacccaag
      181 ctcgttaaat gtcggtctcc tggaaaggaa acattcacct gctggtggga gctggggca
      241 gatggaggac ttcctaccaa ttacacgctg acttaccaca aggaaggaga acactcatc
      301 catgaatgtc cagactacaa aaccggggc cccaactcct gctactttag caagaagcac
      361 acctccatat ggaagatgta cgtcatcaca gtaaacgcca tcaaccagat gggaatcagt
      421 tcctcggatc cactttatgt gcacgtgact tacatagttg aaccagagcc tcctgcaaac
      481 ctgactttgg aattaaaaca tccagaagat agaaaaccat atctatggat aaaatggtct
      541 ccacccacca tgactgatgt aaaatctggt tggttcatta tccagtacga aattcgatta
      601 aaacctgaga agcaactga ttgggagact cattttactc tgaagcaaac tcagcttaag
      661 attttcaact tatatccagg acaaaaatac cttgtgcaga ttcgctgcaa gccagaccat
      721 ggatactgga gtgagtggag cccagagagc tccatccaga tacctaatga cttcccagtg
      781 aaggacacaa gcatgtggat ctttgtggcc atcctttctg ctgtcatctg tttgattatg
      841 gtctgggcag tggctttgaa gggctatagc atggtgacgt gcatcctccc accagttcca
      901 gggccaaaaa taaaaggatt tgatgttcat ctgctggaga agggcaagtc cgaagaactt
      961 ctgcgagctc tggaaagcca agacttcccc ccacttctg actgcgagga cttgctgatg
     1021 gagttcatag aggtagatga ctgtgaggac cagcagctga tgccacgccc ctccaaagaa
     1081 cacacggagc aaggcgtgaa gccatgcac ctggatcttg acagtgactc tggccggggc
     1141 agctgcgaca gccttcgct cttgtctgaa agtgtgatg aacctcaggc ccatccctcc
     1201 aagttccata ctcccgaggg ccctgagaag ctggagaatc cggaaacaaa ccttacatgt
     1261 ctccaggccc ctcagagcac aagcgtggag ggcaaaatcc cctatttttct ggccaatgga
     1321 cccaaatctt ccacatggcc tttcccgcag cccccagcc tatacagccc cagatattct
     1381 taccacaaca ttgctgacgt gtgtgagctg gccctgggca tggccggcac cacagccact
     1441 tcgctggacc aaacagacca acatgCttta aaagcctcaa aaaccattga aactggcagg
     1501 gaaggaaagg caaccaagca gagggagtca gaaggctgca gttccaagcc tgaccaagac
     1561 acggtgtggc cacgaccca agacaaaacc cccttgatct ctgctaaacc cttggaatac
     1621 gtggagatcc acaaggtcag ccaagatgga gtgctggctc tgttcccaaa acaaaacgag
     1681 aagtttggcg ccctgaagc cagcaaggag tactcaaagg tgtcccgggt gacagatagc
     1741 aacatcctgg tattggtgcc ggatccgcaa gcgcaaaacc tgactctgtt agaagaacca
     1801 gccaagaagg ccccgccagc cctgccatag aatccagcca aggccgacct ggctatctcc
     1861 cccacaaccc caggcaactg cagactccag ttgggctggg gactgggtcc cgcaggtttt
     1921 atgcactctt gcagtgagag ttatggaagg atgggttcaa ttgtgatttt ccttcaggga
     1981 acactacaga gtacgtgaaa tgcactctac cagagagggc tcaagaacag ggttagaatg
     2041 acactaccca actcccagtt cactcttaat tctctatttt caaccagttg cctctttgtc
     2101 caacagctga ttccagaaca aatcgttcca tcttgtgtga tttgtagatt tactttttg
     2161 ctattagttg tcagattata tgttcaaaga tataaaagca cattgcctag tattcttaag
     2221 agacagtgcc aataggtata taatctggaa aaggccttca tggtttcgta tgtgacagag
     2281 gggtataagt cagtcaaaat tgtttaccat gggaagatgg tagataggag agaaatgcca
     2341 tgaaaaccac tttgaagacc agttgcttaa cctttgcact cctcttt
```

Figure 2

SEQ ID No. 5:

/translation="MKENAASRVVFILLLFLSVSLLNGQSPPEKPKLVKCRSPGKETF
TCWWEPGADGGLPTNYTLTYHKEGETLIHECPDYKTGGPNSCYFSKKHTSIWKMYVIT
VNAINQMGISSSDPLYVHVTYIVEPEPPANLTLELKHPEDRKPYLWIKWSPPTMTDVK
SGWFIIQYEIRLKPEKATDWETHFTLKQTQLKIFNLYPGQKYLVQIRCKPDHGYWSEW
SPESSIQIPNDFPVKDTSMWIFVAILSAVICLIMVWAVALKGYSMVTCILPPVPGPKI
KGFDVHLLEKGKSEELLRALESQDFPPTSDCEDLLMEFIEVDDCEDQQLMPRPSKEHT
EQGVKPMHLDLDSDSGRGSCDSPSLLSEKCDEPQAHPSKFHTPEGPEKLENPETNLTC
LQAPQSTSVEGKIPYFLANGPKSSTWPFPQPPSLYSPRYSYHNIADVCELALGMAGTT
ATSLDQTDQHALKASKTIETGREGKATKQRESEGCSSKPDQDTVWPRPQDKTPLISAK
PLEYVEIHKVSQDGVLALFPKQNEKFGAPEASKEYSKVSRVTDSNILVLVPDPQAQNL
TLLEEPAKKAPPALP

Figure 3

Sequence ID No 6

ORIGIN
```
   1 ggcaaatgct gaggatactt tccaagtgaa ccctgagtga acctctaata tatttatttc
  61 ctgtggaaag aggaaggagc caacatgaag gaaaatgcag catctagagt ggttttcatt
 121 ttgctacttt ttctcagtgt cagccttctg aatggacagt cacctcctga aaaacccaag
 181 ctcgttaaat gtcggtctcc tggaaaggaa acattcacct gctggtggga gcctggggca
 241 gatggaggac ttcctaccaa ttacacgctg acttaccaca aggaaggaga aacactcatc
 301 catgaatgtc cagactacaa accgggggc cccaactcct gctactttag caagaagcac
 361 acctccatat ggaagatgta cgtcatcaca gtaaacgcca tcaaccagat gggaatcagt
 421 tcctcggatc cactttatgt gcacgtgact tacatagttg aaccagagcc tcctgcaaac
 481 ctgactttgg aattaaaaca tccagaagat agaaaaccat atctatggat aaaatggtct
 541 ccacccacca tgactgatgt aaaatctggt tggttcatta tccagtacga aattcgatta
 601 aaacctgaga agcaactga ttgggagact cattttactc tgaagcaaac tcagcttaag
 661 attttcaact tatatccagg acaaaaatac cttgtgcaga ttcgctgcaa gccagaccat
 721 ggatactgga gtgagtggag cccagagagc tccatccaga tacctaatga cttcccagtg
 781 aaggacacaa gcatgtggat ctttgtggcc atcctttctg ctgtcatctg tttgattatg
 841 gtctgggcag tggctttgaa gggctatagc atggtgacct gcatcctccc accagttcca
 901 gggccaaaaa taaaaggatt tgatgttcat ctgctggaga agggcaagtc cgaagaactt
 961 ctgcgagctc tggaaagcca agacttcccc cccacttctg actgcgagga cttgctgatg
1021 gagttcatag aggtagatga ctgtgaggac cagcagctga tgccacgccc ctccaaagaa
1081 cacacggagc aaggcgtgaa gcccatgcac ctggatcttg acagtgactc tggccggggc
1141 agctgcgaca gcccttcgct cttgtctgaa aagtgtgatg aacctcaggc ccatccctcc
1201 aagttccata ctcccgaggg ccctgagaag ctggagaatc cggaaacaaa ccttacatgt
1261 ctccaggccc ctcagagcac aagcgtggaa ggcaaaatcc ctattttct ggccaatgga
1321 cccaaatctt ccacatggcc tttcccgcag cccccagcc tatacagccc cagatattct
1381 taccacaaca ttgctgacgt gtgtgagctg gccctgggca tggccggcac cacagccact
1441 tcgctggacc aaacagacca acatg ttta aaagcctcaa aaaccattga aactggcagg
1501 gaaggaaagg caaccaagca gagggagtca gaaggctgca gttccaagcc tgaccaagac
1561 acggtgtggc cacgacccca agacaaaacc ccttgatct ctgctaaacc cttggaatac
1621 gtggagatcc acaaggtcag ccaagatgga gtgctggctc tgttcccaaa acaaaacgag
1681 aagtttggcg cccctgaagc cagcaaggag tactcaaagg tgtcccgggt gacagatagc
1741 aacatcctgg tattggtgcc ggatccgcaa gcgcaaaacc tgactctgtt agaagaacca
1801 gccaagaagg ccccgccagc cctgccatag aatccagcca aggccgacct ggctatctcc
1861 cccacaaccc caggcaactg cagactccag ttgggctggg gactgggtcc cgcaggtttt
1921 atgcactctt gcagtgagag ttatggaagg atgggttcaa ttgtgatttt ccttcaggga
1981 acactacaga gtacgtgaaa tgcactctac cagagagggc tcaagaacag ggttagaatg
2041 acactaccca actcccagtt cactcttaat tctctatttt caaccagttg cctctttgtc
2101 caacagctga ttccagaaca aatcgttcca tcttgtgtga tttgtagatt tacttttttg
2161 ctattagttg tcagattata tgttcaaaga tataaaagca cattgcctag tattcttaag
2221 agacagtgcc aataggtata taatctggaa aaggccttca tggtttcgta tgtgacagag
2281 gggtataagt cagtcaaaat tgtttaccat gggaagatgg tagataggag agaaatgcca
2341 tgaaaaccac tttgaagacc agttgcttaa cctttgcact cctcttt
```

Figure 4

Sequence ID No 7

/translation=MKENAASRVVFILLLFLSVSLLNGQSPPEKPKLVKCRSPGKETF
TCWWEPGADGGLPTNYTLTYHKEGETLIHECPDYKTGGPNSCYFSKKHTSIWKMYVIT
VNAINQMGISSSDPLYVHVTYIVEPEPPANLTLELKHPEDRKPYLWIKWSPPTMTDVK
SGWFIIQYEIRLKPEKATDWETHFTLKQTQLKIFNLYPGQKYLVQIRCKPDHGYWSEW
SPESSIQIPNDFPVKDTSMWIFVAILSAVICLIMVWAVALKGYSMVTCILPPVPGPKI
KGFDVHLLEKGKSEELLRALESQDFPPTSDCEDLLMEFIEVDDCEDQQLMPRPSKEHT
EQGVKPMHLDLDSDSGRGSCDSPSLLSEKCDEPQAHPSKFHTPEGPEKLENPETNLTC
LQAPQSTSVEGKIPYFLANGPKSSTWPFPQPPSLYSPRYSYHNIADVCELALGMAGTT
ATSLDQTDQHV

Figure 5:

SEQ ID No. 8
ORIGIN

```
   1 cgggcaaatg ctgaggatac tttccaagtg aaccctgagt gaacctctaa tatatttatt
  61 tcctgtggaa agaggaagga gccaacatga aggaaaatgc agcatctaga gtggttttca
 121 ttttgctact ttttctcagt gtcagccttc tgaatggaca gtcacctcct gaaaaccca
 181 agctcgttaa atgtcggtct cctggaaagg aaacattcac ctgctggtgg gaggctgggg
 241 cagatggagg acttcctacc aattacacgc tgacttacca caaggaagga gaacactca
 301 tccatgaatg tccagactac aaaaccgggg gccccaactc ctgctacttt agcaagaagc
 361 acacctccat atggaagatg tacgtcatca cagtaaacgc catcaaccag atgggaatca
 421 gttcctcgga tccactttat gtgcacgtga cttacatagt tgaaccagag cctcctgcaa
 481 acctgacttt ggaattaaaa catccagaag atagaaaacc atatctatgg ataaaatggt
 541 ctccacccac catgactgat gtaaaatctg gttggttcat tatccagtac gaaattcgat
 601 taaaacctga gaaagcaact gattgggaga ctcattttac tctgagcaa actcagctta
 661 agattttcaa cttatatcca ggacaaaaat accttgtgca gattcgctgc aagccagacc
 721 atggatactg gagtgagtgg agcccagaga gctccatcca gatacctaat gacttcccag
 781 tgaaggacac aagcatgtgg atctttgtgg ccatcctttc tgctgtcatc tgtttgatta
 841 tggtctgggc agtggctttg aagggctata gcatggtgac ctgcatcctc ccaccagttc
 901 cagggccaaa aataaaagga tttgatgttc atctgctgg gaagggcaag tccgaagaac
 961 ttctgcgagc tctggaaagc caagacttcc cccccactcc tgactgcgag gacttgctga
1021 tggagttcat agaggtagat gactgtgagg accagcagct gatgccacgc ccctccaaag
1081 aacacacgga gcaaggcgtg aagcccatgc acctggatct tgacagtgac tctggccggg
1141 gcagctgcga cagcccttcg ctcttgtctg aaagtgtga tgaacctcag gcccatccct
1201 ccaagttcca tactcccgag ggccctgaga agtggagaa tccggaaaca aaccttacat
1261 gtctccaggc ccctcagagc acaagcgtgg aaggcaaaat ccctattt ctggccaatg
1321 gacccaaatc ttccacatgg ccttcccgc agccccccag cctatacagc cccagatatt
1381 cttaccacaa cattgctgac gtgtgtgagc tggccctggg catggccggc accacagcca
1441 cttcgctgga ccaaacagac caacatgctt taaaagcctc aaaaaccatt gaaactggca
1501 gggaaggaaa ggcaaccaag cagagggagt cagaaggctg cagttccaag cctgaccaag
1561 acacggtgtg gccacgaccc caagacaaaa ccccctttgat ctctgctaaa ccttggaat
1621 acgtggagat ccacaaggtc agccaagatg gagtgctggc tctgttccca aaacaaaacg
1681 agaagtttgg cgccctgaa gccagcaagg agtactcaaa ggtgtcccgg gtgacagata
1741 gcaacatcct ggtattggtg ccggatccgc aagcgcaaaa cctgactctg ttagaagaac
1801 cagccaagaa ggccccgcca gccctgccat agaatccagc caaggccgac ctggctatct
1861 cccccacaac cccaggcaac tgcagactcc agttgggctg gggactgggt cccgcaggtt
1921 ttatgcactc ttgcagtgag agttatggaa ggatgggttc aattgtgatt ttccttcagg
1981 gaacactaca gagtacgtga atgcactct accagagagg gctcaagaac agggttagaa
2041 tgacactacc caactcccag ttcactctta attctctatt ttcaaccagt tgcctctttg
2101 tccaacagct gattccagaa caaatcgttc catcttgtgt gatttgtaga tttactttt
2161 tgctattagt tgtcagatta tatgttcaaa gatataaaag cacattgcct agtattctta
2221 agagacagtg ccaataggta tataatctgg aaaaggcctt catggtttcg tatgtgacag
2281 aggggtataa gtcagtcaaa attgtttacc atgggaagat ggtagatagg agagaaatgc
2341 catgaaaacc actttgaaga ccagttgctt aacctttgca ctcctcttt
```

GENETIC MARKERS AND USES THEREFOR

STATEMENT REGARDING SEQUENCE LISTING

The Sequence Listing associated with this application is provided in text format in lieu of a paper copy, and is hereby incorporated by reference into the specification. The name of the text file containing the Sequence Listing is 600094_401USPC_SEQUENCE_LISTING.txt. The text file is 18.9 KB, was created on Apr. 12, 2016, and is being submitted electronically via EFS-Web.

FIELD

The present invention relates, inter alia, to methods for determining whether or not an animal and/or its offspring are more likely than not to have an increased tolerance to heat, increased resistance to ticks, and/or a desirable coat texture, and particularly but not exclusively, to methods for selecting or rejecting animals, one or more cells or embryos, estimating the worth of an animal, breeding animals and herd formation.

BACKGROUND

The ability to maintain normal body temperatures under heat stress is an important trait for cattle and other animals. This is of particular importance for animals in subtropical and tropical regions. In cattle, for example, heat stress has been associated with decreases in milk production, decreases in estrus detection, lower fertility and pregnancy rates, and increases in embryo mortality. These factors can have a significant impact on the farming of production animals.

Some animals are naturally able to regulate body temperature more effectively than others in subtropical and tropical climates. An example of this is the Senepol breed of cattle. Senepol cattle have very short, sleek hair coats.

It would be useful to be able to identify animals that are more likely than not to be able to maintain a normal body temperature or more effectively regulate body temperature under heat stress. The animals could then be selected for inclusion in a herd or for breeding purposes. This may be of particular use where the animals are intended to be farmed in locations where they will be exposed to relatively high temperature conditions.

Bibliographic details of the publications referred to herein are collected at the end of the description.

OBJECT

It is an object of the present invention to provide one or more of a method of determining whether or not an animal and/or its offspring is more likely than not to have an increased tolerance to heat, an increased resistance to ticks, and/or a desirable coat texture, a method for selecting or rejecting animals, a method for selecting or rejecting one or more cells, a method for a method for estimating the worth of an animal, a method for breeding animals, a method for cloning an animal, a method for generating an animal, a method of forming a herd, a method for identify one or more marker which infers an increased tolerance to heat, an increased resistance to ticks, and/or a desirable coat texture, a method for identifying whether or not an animal (and/or its offspring), or one or more cells or an embryo may have a marker which is linked to increased tolerance to heat, an increased resistance to ticks, and/or a desirable coat texture, a nucleic acid, a peptide, a kit and/or at least to provide the public with a useful choice.

STATEMENT OF INVENTION

The inventors have identified that a sequence alteration or variation in the Prolactin Receptor (PRLR) gene is associated with an animal having an increased tolerance to heat, an increased resistance to ticks, and/or a desirable coat texture. The alteration or variation can be used as a genetic marker to determine whether or not an animal is more likely than not to have increased heat tolerance. Such information may be used in methods for selecting, screening and breeding animals, farm management, and for estimating an animal's worth to a particular industry, for example.

In a first aspect, the invention provides a method for determining whether it is more likely than not that an animal and/or its offspring will have an increased tolerance to heat, an increased resistance to ticks, and/or a desirable coat texture, the method comprising at least the step of analysing a nucleic acid from said animal to determine whether or not it includes one or more genetic variation in the PRLR gene and/or includes one or more genetic marker in linkage disequilibrium therewith, wherein where the nucleic acid includes said genetic variation and/or one or more genetic marker in linkage disequilibrium therewith, the animal and/or its offspring is determined to be more likely than not to have an increased tolerance to heat, an increased resistance to ticks, and/or a desirable coat texture.

In one embodiment, one or more genetic alteration in the PRLR gene results in an increase in PRLR activity.

In one embodiment, the method comprises analysing a nucleic acid from said animal to determine whether or not it includes one or more genetic alteration located within a region bounded by nucleotides corresponding to positions 39136469 and 39136649 of chromosome 20 of Bos Taurus and/or one or more genetic marker in linkage disequilibrium therewith. In one embodiment, the method comprises analysing a nucleic acid from said animal to determine whether or not it includes one or more genetic alteration located in the final exon of the PRLR gene and/or one or more genetic marker in linkage disequilibrium therewith.

In one embodiment, the method comprises analysing a nucleic acid from said animal to determine the nucleotide at a position corresponding to position 39136559 of chromosome 20 of Bos Taurus and/or the nucleotide sequence of one or more genetic marker in linkage disequilibrium therewith.

In one embodiment, the deletion of a C at the position corresponding to position 39136559 and/or the presence of one or more genetic marker in linkage disequilibrium therewith, infers that the animal and/or its offspring is more likely than not to have increased heat tolerance.

In a second aspect the invention provides a method for selecting or rejecting an animal, the method comprising at least the step of analysing a nucleic acid from said animal to determine whether or not it includes one or more genetic variation in the PRLR gene and/or includes one or more genetic marker in linkage disequilibrium therewith, wherein the presence of one or more genetic variation and/or one or more genetic marker in linkage disequilibrium therewith infers that the animal is more likely than not to have increased tolerance to heat, an increased resistance to ticks, and/or a desirable coat texture.

In one embodiment, an animal is selected if it includes one or more genetic variation in the PRLR gene and/or one or more genetic marker in linkage disequilibrium therewith and an animal is rejected if it does not include one or more genetic variation in the PRLR gene and/or one or more genetic marker in linkage disequilibrium therewith.

In one embodiment, one or more genetic alteration in the PRLR gene results in an increase in PRLR activity.

In one embodiment, an animal is selected if it is inferred to be more likely than not to have increased tolerance to heat, an increased resistance to ticks, and/or a desirable coat texture. In one embodiment, an animal is rejected if it is inferred not to be more likely than not to have increased tolerance to heat, an increased resistance to ticks, and/or a desirable coat texture.

In one embodiment, the method comprises analysing a nucleic acid from said animal to determine whether or not it includes one or more genetic alteration located within a region bounded by nucleotides corresponding to positions 39136469 and 39136649 of chromosome 20 of *Bos Taurus* and/or one or more genetic marker in linkage disequilibrium therewith. In one embodiment, the method comprises analysing a nucleic acid from said animal to determine whether or not it includes one or more genetic alteration located in the final exon of the PRLR gene and/or one or more genetic marker in linkage disequilibrium therewith.

In one embodiment, the method comprises at least the step of analysing a nucleic acid from said animal to determine the nucleotide at a position corresponding to position 39136559 of chromosome 20 of *Bos Taurus* and/or the nucleotide sequence of one or more genetic marker in linkage disequilibrium therewith.

In one embodiment, the method comprises at least the steps of:
a) analysing a nucleic acid from the animal to determine the nucleotide present at the position corresponding to position 39136559 and/or the nucleotide sequence of one or more genetic marker in linkage disequilibrium therewith; and,
b) selecting or rejecting an animal based on the nucleotide present at the position corresponding to position 39136559 and/or the nucleotide sequence of one or more genetic marker in linkage disequilibrium therewith.

In one embodiment, the animal is selected if there is a deletion of a C at the position corresponding to position 39136559 and/or has one or more genetic marker in linkage disequilibrium therewith.

In one embodiment, the method is performed for the purpose of selecting or rejecting an animal for milk production. In one embodiment, the method is performed for the purpose of selecting or rejecting an animal for meat production. In one embodiment, the method is performed for the purpose of selecting or rejecting an animal for egg production. In one embodiment, the method is performed for the purpose of selecting or rejecting an animal for fur, hair, wool, skin, or feather production. In one embodiment, the method is performed for selecting or rejecting an animal for a desirable coat texture. In another embodiment, the method is performed for the purpose of selecting or rejecting an animal for breeding purposes. In one embodiment, the method is performed for the purpose of selecting or rejecting an animal for inclusion in a herd. In one embodiment, where the method is for selecting or rejecting an animal for breeding purposes and/or for inclusion in a herd, the method comprises determining whether or not the animal is homozygous or heterozygous for the one or more genetic alteration and/or one or more genetic marker in linkage disequilibrium therewith. In one particular embodiment, the animal is selected where it is homozygous for the one or more genetic alteration and/or the one or more genetic marker in linkage disequilibrium therewith which infers that it is more likely than not that an animal will have an increased tolerance to heat, an increased resistance to ticks, and/or a desirable coat texture.

In a third aspect, the invention provides a method for estimating the worth of an animal and/or its offspring, the method comprising at least the step of analysing a nucleic acid from said animal to determine whether or not it includes one or more genetic variation in the PRLR gene and/or one or more genetic marker in linkage disequilibrium therewith, wherein the presence of one or more genetic variation and/or one or more genetic marker in linkage disequilibrium therewith infers that the animal and/or its offspring will more likely than not to have an increased tolerance to heat, an increased resistance to ticks, and/or a desirable coat texture.

In one embodiment, one or more genetic alteration in the PRLR gene results in an increase in PRLR activity.

In one embodiment, the method comprises analysing a nucleic acid from said animal to determine whether or not it includes one or more genetic alteration located within a region bounded by nucleotides corresponding to positions 39136469 and 39136649 of chromosome 20 of *Bos Taurus* and/or one or more genetic marker in linkage disequilibrium therewith. In one embodiment, the method comprises analysing a nucleic acid from said animal to determine whether or not it includes one or more genetic alteration located in the final exon of the PRLR gene and/or one or more genetic marker in linkage disequilibrium therewith.

In one embodiment, the method comprises analysing a nucleic acid from said animal to determine the nucleotide at a position corresponding to position 39136559 of chromosome 20 of *Bos Taurus* and/or the nucleotide sequence of one or more genetic marker in linkage disequilibrium therewith.

In one embodiment, if there is a deletion of a C at the position corresponding to position 39136559 and/or the presence of one or more genetic marker in linkage disequilibrium therewith infers that the animal and/or its offspring will more likely than not have increased tolerance to heat, an increased resistance to ticks, and/or a desirable coat texture.

In a fourth aspect, the invention provides a method for breeding animals, which method comprises at least the step of selecting at least a first animal that has one or more genetic variation in the PRLR gene and/or has one or more genetic marker in linkage disequilibrium therewith and mating said first animal with a second animal.

In one embodiment, the method further comprises selecting the second animal on the basis that it includes one or more genetic variation in the PRLR gene and/or has one or more genetic marker in linkage disequilibrium therewith. In one embodiment, one or more genetic alteration in the PRLR gene results in an increase in PRLR activity.

In one embodiment, the first and/or second animal is selected if it is inferred to be more likely than not to have increased tolerance to heat, an increased resistance to ticks, and/or a desirable coat texture.

In one embodiment, one or more genetic alteration in the PRLR gene results in an increase in PRLR activity.

In one embodiment, the one or more genetic alteration is located within a region bounded by nucleotides corresponding to positions 39136469 and 39136649 of chromosome 20 of *Bos Taurus*. In one embodiment, the one or more genetic alteration is located in the final exon of the PRLR gene.

In one embodiment, the method comprises selecting the first and/or second animal where it has a genetic variation at a position corresponding to position 39136559 of chromosome 20 of *Bos Taurus* and/or has one or more genetic marker in linkage disequilibrium therewith. In one embodiment, the method comprises selecting the first and/or second animal where there is a deletion of a C at the position corresponding to position 39136559 and/or has one or more genetic marker in linkage disequilibrium therewith.

In one embodiment, the method comprises selecting the first and/or second animal where the animal is determined to be homozygous for one or more particular genetic alteration and/or one or more genetic marker in linkage disequilibrium therewith.

In a fifth aspect the invention provides a method for selecting or rejecting one or more cell or embryo, the method comprising at least the step of analysing a nucleic acid from said one or more cell or embryo or an animal from which the one or more cell or embryo is derived, to determine whether or not it includes one or more genetic variation in the PRLR gene and/or includes one or more genetic marker in linkage disequilibrium therewith. In one embodiment, the presence of such one or more genetic variation and/or one or more genetic marker in linkage disequilibrium therewith infers that the one or more cell or embryo is suitable for use in a method for breeding or cloning an animal which is more likely than not to have increased tolerance to heat, an increased resistance to ticks, and/or a desirable coat texture.

In one embodiment, one or more cell or embryo is selected if it, or an animal from which the one or more cell or embryo is derived, includes one or more genetic variation in the PRLR gene and/or includes one or more genetic marker in linkage disequilibrium therewith. In one embodiment, one or more cell or embryo is rejected if it, or an animal from which the one or more cell or embryo is derived, does not include one or more genetic variation in the PRLR gene and/or one or more genetic marker in linkage disequilibrium therewith.

In one embodiment, one or more genetic alteration in the PRLR gene results in an increase in PRLR activity.

In one embodiment, the one or more genetic alteration is located within a region bounded by nucleotides corresponding to positions 39136469 and 39136649 of chromosome 20 of *Bos Taurus*. In one embodiment, the one or more genetic alteration is located in the final exon of the PRLR gene.

In one embodiment, the method comprises at least the step of analysing a nucleic acid from said one or more cell or embryo, or from an animal from which the one or more cell or embryo is derived, to determine the nucleotide at a position corresponding to position 39136559 of chromosome 20 of *Bos Taurus* and/or the nucleotide sequence of one or more genetic marker in linkage disequilibrium therewith.

In one embodiment, the method comprises at least the steps of:
a) analysing a nucleic acid from the one or more cell or embryo, or from an animal from which the one or more cell or embryo is derived, to determine the nucleotide present at the position corresponding to position 39136559 and/or the nucleotide sequence of one or more genetic marker in linkage disequilibrium therewith; and,
b) selecting or rejecting one or more cell or embryo, based on the nucleotide present at the position corresponding to position 39136559 and/or the nucleotide sequence of one or more genetic marker in linkage disequilibrium therewith.

In one embodiment, the one or more cell or embryo is selected if there is a deletion of a C at the position corresponding to position 39136559 and/or has one or more genetic marker in linkage disequilibrium therewith.

In one embodiment, the method comprises determining whether or not the one or more cell or embryo, or an animal from which the one or more cell or embryo is derived, is homozygous or heterozygous for the one or more genetic alteration and/or the one or more genetic marker in linkage disequilibrium therewith. In one particular embodiment, the one or more cell or embryo is selected where it, or an animal from which the one or more cell or embryo is derived, is homozygous for the one or more genetic alteration and/or the one or more genetic marker in linkage disequilibrium therewith.

In one embodiment, the method is performed for the purpose of selecting or rejecting one or more cell or embryo for use in cloning an animal and/or breeding an animal. In one embodiment, breeding an animal may involve IVF.

In a sixth aspect, the invention provides a method for breeding animals, the method comprising at least the step of selecting a first gamete that has one or more genetic variation in the PRLR gene and/or has one or more genetic marker in linkage disequilibrium therewith and fusing said first gamete with a second gamete to form a zygote.

In one embodiment, the method further comprises selecting the second gamete on the basis that it includes one or more genetic variation in the PRLR gene and/or has one or more genetic marker in linkage disequilibrium therewith.

In a seventh aspect, the invention provides a method of breeding an animal, the method comprising at least the step of selecting an embryo that has one or more genetic variation in the PRLR gene and/or has one or more genetic marker in linkage disequilibrium therewith.

In an eighth aspect, the invention provides a method of cloning an animal, the method comprising at least the step of selecting one or more cell that has one or more genetic variation in the PRLR gene and/or has one or more genetic marker in linkage disequilibrium therewith.

In one embodiment of any one of the sixth to eighth aspects, one or more genetic alteration in the PRLR gene results in an increase in PRLR activity. In one embodiment, the one or more genetic alteration is located within a region bounded by nucleotides corresponding to positions 39136469 and 39136649 of chromosome 20 of *Bos Taurus*. In one embodiment, the one or more genetic alteration is located in the final exon of the PRLR gene.

In one embodiment of any one of the sixth to eighth aspects, the methods comprise selecting the first and/or second gamete, the embryo or one or more cell where it has a genetic variation at a position corresponding to position 39136559 of chromosome 20 of *Bos Taurus* and/or has one or more genetic marker in linkage disequilibrium therewith. In one embodiment, the methods comprise selecting the first and/or second gamete, the embryo or the one or more cell where there is a deletion of a C at the position corresponding to position 39136559 and/or has one or more genetic marker in linkage disequilibrium therewith. In one embodiment, the method comprises selecting the first and/or second gamete, the embryo or one or more cell where it is determined to be homozygous for one or more genetic alteration and/or one or more genetic marker in linkage disequilibrium therewith.

In one embodiment of any one or more of the first to eighth broad aspects of the invention, the methods comprise analysing a nucleic acid to determine whether or not it includes one or more genetic variation in the PRLR gene alone or in combination with one or more genetic marker in linkage disequilibrium therewith. In one embodiment, the methods involve analysing a nucleic acid to determine the nucleotide present at a position corresponding to position 39136559 of chromosome 20 of *Bos Taurus* alone or in combination with one or more genetic marker in linkage disequilibrium therewith.

Preferably, analysis of a nucleic acid in accordance with any one or more of the first to eighth aspects of the invention occurs using one or more of: polymerase chain reaction (PCR); gel electrophoresis; Southern blotting; nucleic acid sequencing; restriction fragment length polymorphism (RFLP); single-strand confirmation polymorphism (SSCP); LCR (ligase chain reaction); denaturing gradient gel electrophoresis (DGGE); allele-specific oligonucleotides (ASOs); proteins which recognize nucleic acid mismatches; RNAse protection; oligonucleotide array hybridisation; denaturing HPLC (dHPLC); high resolution melting (HRM); and, matrix-assisted laser desorption/ionisation time-of-flight mass spectrometry (MALDI-TOF MS), qRT-PCR.

In a ninth aspect, the invention provides a method for determining whether it is more likely than not that an animal and/or its offspring will have an increased tolerance to heat, an increased resistance to ticks, and/or a desirable coat texture, the method comprising at least the step of observing in the animal the level of one or more of PRLR, one or more precursor thereof, one or more isoform thereof, one or more fragment thereof, and/or one or more nucleic acid encoding any one or more thereof.

In one embodiment, the method comprises comparing the level of PRLR, one or more precursor thereof, one or more isoform thereof, one or more fragment thereof, and/or one or more nucleic acid encoding any one or more thereof against one or more standard.

In one embodiment, the standard comprises a level of PRLR, one or more precursor thereof, one or more isoform thereof, one or more fragment thereof, and/or one or more nucleic acid encoding any one or more thereof which is associated with an animal having a substantially limited tolerance to heat and/or a desirable coat texture and a higher level of PRLR, one or more precursor thereof, one or more isoform thereof, one or more fragment thereof, and/or one or more nucleic acid encoding any one or more thereof from the animal compared to the standard infers that the animal and/or its offspring will more likely than not have an increased tolerance to heat, an increased resistance to ticks, and/or a desirable coat texture.

In one embodiment, the level of PRLR, one or more precursor thereof, one or more isoform thereof, one or more fragment thereof, and/or one or more nucleic acid encoding any one or more thereof is the level of expression thereof.

In a tenth aspect the invention provides a method for selecting or rejecting an animal the method comprising at least the step of observing the level of one or more of PRLR, one or more precursor thereof, one or more isoform thereof, one or more fragment thereof, and/or one or more nucleic acid encoding any one or more thereof.

In one embodiment, an animal is selected it if has a level of one or more of PRLR, one or more precursor thereof, one or more isoform thereof, one or more fragment thereof, and/or one or more nucleic acid encoding any one or more thereof which is indicative of an animal which has or is more likely than not to have an increased tolerance to heat, an increased resistance to ticks, and/or a desirable coat texture. In one embodiment, an animal is rejected if it does not have a level of one or more of PRLR, one or more precursor thereof, one or more isoform thereof, one or more fragment thereof, and/or one or more nucleic acid encoding any one or more thereof which is indicative of an animal which has or is more likely than not to have an increased tolerance to heat, an increased resistance to ticks and/or a desirable coat texture.

In one embodiment, the method comprises comparing the level of PRLR, one or more precursor thereof, one or more isoform thereof, one or more fragment thereof, and/or one or more nucleic acid encoding any one or more thereof against one or more standard.

In one embodiment, the standard comprises a level of PRLR, one or more precursor thereof, one or more isoform thereof, one or more fragment thereof, and/or one or more nucleic acid encoding any one or more thereof which is associated with an animal having a substantially limited tolerance to heat and/or an undesirable coat texture and a higher level of PRLR, one or more precursor thereof, one or more isoform thereof, one or more fragment thereof, and/or one or more nucleic acid encoding any one or more thereof from the animal compared to the standard infers that the animal will more likely than not have an increased tolerance to heat, an increased resistance to ticks, and/or a desirable coat texture.

In one embodiment, an animal is selected if it is inferred that it will more likely than not have an increased tolerance to heat, an increased resistance to ticks, and/or a desirable coat texture. In one embodiment, an animal is rejected if it is inferred not to be more likely than not to have an increased tolerance to heat, an increased resistance to ticks, and/or a desirable coat texture.

In one embodiment, the level of PRLR, one or more precursor thereof, one or more isoform thereof, one or more fragment thereof, and/or one or more nucleic acid encoding any one or more thereof is the level of expression thereof.

In one embodiment, the method is performed for the purpose of selecting or rejecting an animal for milk production. In one embodiment, the method is performed for the purpose of selecting or rejecting an animal for meat production. In one embodiment, the method is performed for the purpose of selecting or rejecting an animal for egg production. In one embodiment, the method is performed for the purpose of selecting or rejecting an animal for fur, hair, wool, skin, or feather production. In one embodiment, the method is performed for selecting or rejecting an animal for a desirable coat texture. In another embodiment, the method is performed for the purpose of selecting or rejecting an animal for breeding purposes. In one embodiment, the method is performed for the purpose of selecting or rejecting an animal for inclusion in a herd.

In an eleventh aspect the invention provides a method for estimating the worth of an animal and/or its offspring, the method comprising at least the step of observing the level of one or more of PRLR, one or more precursor thereof, one or more isoform thereof, one or more fragment thereof, and/or one or more nucleic acid encoding any one or more thereof.

In one embodiment, the method comprises comparing the level of PRLR, one or more precursor thereof, one or more isoform thereof, one or more fragment thereof, and/or one or more nucleic acid encoding any one or more thereof against one or more standard.

In one embodiment, the standard comprises a level of PRLR, one or more precursor thereof, one or more isoform thereof, one or more fragment thereof, and/or one or more nucleic acid encoding any one or more thereof which is associated with an animal having a substantially limited tolerance to heat and/or an undesirable coat texture and a higher level of PRLR, one or more precursor thereof, one or more isoform thereof, one or more fragment thereof, and/or one or more nucleic acid encoding any one or more thereof from the animal compared to the standard infers that the animal and/or its offspring will more likely than not have an increased tolerance to heat, an increased resistance to ticks, and/or a desirable coat texture.

In one embodiment, the level of PRLR, one or more precursor thereof, one or more isoform thereof, one or more fragment thereof, and/or one or more nucleic acid encoding any one or more thereof is the level of expression thereof.

In a twelfth aspect, the invention provides a method for breeding animals, the method comprising at least the step of selecting a first animal identified to have a level of one or more of PRLR, one or more precursor thereof, one or more isoform thereof, one or more fragment thereof, and/or one or more nucleic acid encoding any one or more thereof which is indicative of an animal which has or is more likely than not to have an increased tolerance to heat, an increased resistance to ticks and/or a desirable coat texture and mating said first animal with a second animal.

In another embodiment, the method further comprises selecting a second animal identified to have a level of one or more of PRLR, one or more precursor thereof, one or more isoform thereof, one or more fragment thereof, and/or one or more nucleic acid encoding any one or more thereof which is indicative of an animal which has or is more likely than not to have an increased tolerance to heat, an increased resistance to ticks and/or a desirable coat texture.

In one embodiment, the method comprises the step of observing the level of one or more of PRLR, one or more precursor thereof, one or more isoform thereof, one or more fragment thereof, and/or one or more nucleic acid encoding any one or more thereof from the first and/or second animal to identify whether or not it has a level of one or more of PRLR, one or more precursor thereof, one or more isoform thereof, one or more fragment thereof, and/or one or more nucleic acid encoding any one or more thereof which is indicative of an animal which has or is more likely than not to have an increased tolerance to heat, an increased resistance to ticks and/or a desirable coat texture.

In one embodiment, the method comprises comparing the level of one or more of PRLR, one or more precursor thereof, one or more isoform thereof, one or more fragment thereof, and/or one or more nucleic acid encoding any one or more thereof against one or more standard.

In one embodiment, the standard comprises a level of PRLR, one or more precursor thereof, one or more isoform thereof, one or more fragment thereof, and/or one or more nucleic acid encoding any one or more thereof which is associated with an animal having a substantially limited tolerance to heat and/or an undesirable coat texture and the first and/or second animal is selected where it is observed to have a higher level of one or more of PRLR, one or more precursor thereof, one or more isoform thereof, one or more fragment thereof, and/or one or more nucleic acid encoding any one or more thereof compared to the standard.

In one embodiment, the level of PRLR, one or more precursor thereof, one or more isoform thereof, one or more fragment thereof, and/or one or more nucleic acid encoding any one or more thereof is the level of expression thereof.

In one embodiment, the first and/or second animal is selected if it is inferred to be more likely than not to have increased tolerance to heat, an increased resistance to ticks, and/or a desirable coat texture.

In one embodiment of any one or more of the ninth to twelfth aspects, the methods comprise at least the steps of:

a) taking a sample from an animal;
b) detecting one or more of PRLR, one or more precursor thereof, one or more isoform thereof, one or more fragment thereof, and/or one or more nucleic acid encoding one or more thereof in the sample; and,
c) comparing the level of the one or more of PRLR, one or more precursor thereof, one or more isoform thereof, one or more fragment thereof, and/or one or more nucleic acid encoding one or more thereof against a standard.

In a thirteenth aspect the invention provides a method for selecting or rejecting one or more cell or embryo, the method comprising at least the step of observing the level of one or more of PRLR, one or more precursor thereof, one or more isoform thereof, one or more fragment thereof, and/or one or more nucleic acid encoding any one or more thereof, in the one or more cell or embryo or an animal from which it is derived.

In one embodiment, the one or more cell or embryo is selected where it, or an animal from which it is derived, is identified to have a level of one or more of PRLR, one or more precursor thereof, one or more isoform thereof, one or more fragment thereof, and/or one or more nucleic acid encoding any one or more thereof which is indicative of an animal which has or is more likely than not to have an increased tolerance to heat, an increased resistance to ticks and/or a desirable coat texture. In one embodiment, the one or more cell or embryo is rejected where it, or an animal from which it is derived, is identified not to have a level of one or more of PRLR, one or more precursor thereof, one or more isoform thereof, one or more fragment thereof, and/or one or more nucleic acid encoding any one or more thereof which is indicative of an animal which has or is more likely than not to have an increased tolerance to heat, an increased resistance to ticks and/or a desirable coat texture.

In one embodiment, the method comprises comparing the level of PRLR, one or more precursor thereof, one or more isoform thereof, one or more fragment thereof, and/or one or more nucleic acid encoding any one or more thereof from the one or more cell or embryo, or an animal from which it is derived, against one or more standard.

In one embodiment, the standard comprises a level of PRLR, one or more precursor thereof, one or more isoform thereof, one or more fragment thereof, and/or one or more nucleic acid encoding any one or more thereof which is associated with an animal having a substantially limited tolerance to heat and/or an undesirable coat texture and a higher level of PRLR, one or more precursor thereof, one or more isoform thereof, one or more fragment thereof, and/or one or more nucleic acid encoding any one or more thereof from the one or more cell or embryo, or an animal from which the one or more cell or embryo is derived, compared to the standard infers that the one or more cell or embryo is suitable for use in a method for breeding or cloning an animal which is more likely than not to have increased tolerance to heat, an increased resistance to ticks, and/or a desirable coat texture. In one embodiment, one or more cell or embryo is selected if it, or an animal from which the one or more cell or embryo is derived, has a higher level of PRLR, one or more precursor thereof, one or more isoform thereof, and/or one or more nucleic acid encoding any one or more thereof.

In one embodiment, the level of PRLR, one or more precursor thereof, one or more isoform thereof, one or more fragment thereof, and/or one or more nucleic acid encoding any one or more thereof is the level of expression thereof.

In one embodiment, the method is performed for the purpose of selecting or rejecting one or more cell or embryo for use in cloning an animal and/or breeding an animal. In one embodiment, breeding an animal may involve IVF.

In a fourteenth aspect, the invention provides a method for breeding animals, the method comprising at least the step of selecting a first gamete identified to have a level of one or more of PRLR, one or more precursor thereof, one or more isoform thereof, one or more fragment thereof, and/or one or more nucleic acid encoding any one or more thereof which is indicative of an animal which has or is more likely than not to have an increased tolerance to heat, an increased resistance to ticks and/or a desirable coat texture and fusing said first gamete with a second gamete to form a zygote.

In one embodiment, the method further comprises selecting the second gamete where it is identified to have a level of one or more of PRLR, one or more precursor thereof, one or more isoform thereof, one or more fragment thereof, and/or one or more nucleic acid encoding any one or more thereof which is indicative of an animal which has or is more likely than not to have an increased tolerance to heat, an increased resistance to ticks and/or a desirable coat texture.

In a fifteenth aspect, the invention provides a method of breeding an animal, the method comprising at least the step of selecting an embryo where it is identified to have a level of one or more of PRLR, one or more precursor thereof, one or more isoform thereof, one or more fragment thereof, and/or one or more nucleic acid encoding any one or more thereof which is indicative of an animal which has or is more likely than not to have an increased tolerance to heat, an increased resistance to ticks and/or a desirable coat texture.

In a sixteenth aspect, the invention provides a method of cloning an animal, the method comprising at least the step of selecting one or more cell where it is identified to have a level of one or more of PRLR, one or more precursor thereof, one or more isoform thereof, one or more fragment thereof, and/or one or more nucleic acid encoding any one or more thereof which is indicative of an animal which has or is more likely than not to have an increased tolerance to heat, an increased resistance to ticks and/or a desirable coat texture.

In one embodiment of the fourteenth to sixteenth aspects, the method comprises the step of observing the level of one or more of PRLR, one or more precursor thereof, one or more isoform thereof, one or more fragment thereof, and/or one or more nucleic acid encoding any one or more thereof in said first and/or second gamete, one or more cell or embryo to identify whether or not it has a level of one or more of PRLR, one or more precursor thereof, one or more isoform thereof, one or more fragment thereof, and/or one or more nucleic acid encoding any one or more thereof which is indicative of an animal which has or is more likely than not to have an increased tolerance to heat, an increased resistance to ticks and/or a desirable coat texture.

In one embodiment, the methods of the fourteenth to sixteenth aspects comprise comparing the level of one or more of PRLR, one or more precursor thereof, one or more isoform thereof, one or more fragment thereof, and/or one or more nucleic acid encoding any one or more thereof in said first and/or second gamete, embryo or one or more cell to one or more standard.

In one embodiment of any one of the fourteenth to sixteenth aspects, the standard comprises a level of PRLR, one or more precursor thereof, one or more isoform thereof, one or more fragment thereof, and/or one or more nucleic acid encoding any one or more thereof which is associated with an animal having a substantially limited tolerance to heat and/or an undesirable coat texture and the first and/or second gamete, embryo or one or more cell is selected where it is observed to have a higher level of one or more of PRLR, one or more precursor thereof, one or more isoform thereof, one or more fragment thereof, and/or one or more nucleic acid encoding any one or more thereof compared to the standard.

In one embodiment, the level of PRLR, one or more precursor thereof, one or more isoform thereof, one or more fragment thereof, and/or one or more nucleic acid encoding any one or more thereof is the level of expression thereof.

In certain embodiments of the ninth to sixteenth aspects the level of the one or more of PRLR, one or more precursor thereof, one or more isoform thereof, one or more fragment thereof, and/or one or more nucleic acid encoding one or more thereof is determined using an immunoassay, separation based on characteristics such as molecular weight and isoelectric point, gel electrophoresis, Western Blotting or mass spectroscopy. Preferably the immunoassay is an ELISA. Preferably the gel electrophoresis is 2D gel electrophoresis or gel-free systems based on microfluidics technologies.

In a seventeenth aspect, the invention provides a method for determining whether it is more likely than not that an animal and/or its offspring will have an increased tolerance to heat, an increased resistance to ticks, and/or a desirable coat texture, the method comprising at least the step of observing in the animal the level of activity of PRLR, one or more precursor thereof, one or more isoform thereof, and/or one or more fragment thereof.

In one embodiment, the method comprises comparing the level of activity of PRLR, one or more precursor thereof, one or more isoform thereof, and/or one or more fragment thereof against one or more standard.

In one embodiment, the standard comprises a level of activity of PRLR, one or more precursor thereof, one or more isoform thereof, and/or one or more fragment thereof associated with an animal having a substantially limited tolerance to heat and/or an undesirable coat texture and a higher level of activity of PRLR, one or more precursor thereof, one or more isoform thereof, and/or one or more fragment thereof in the animal compared to the standard infers that the animal and/or its offspring will more likely than not have an increased tolerance to heat, an increased resistance to ticks, and/or a desirable coat texture.

In an eighteenth aspect the invention provides a method for selecting or rejecting an animal the method comprising at least the step of observing the level of activity of PRLR, one or more precursor thereof, one or more isoform thereof, and/or one or more fragment thereof.

In one embodiment, an animal is selected it if has a level of activity of one or more of PRLR, one or more precursor thereof, one or more isoform thereof, and/or one or more fragment thereof which is indicative of an animal which has or is more likely than not to have an increased tolerance to heat, an increased resistance to ticks and/or a desirable coat texture. In one embodiment, an animal is rejected if it does not have a level of activity of one or more of PRLR, one or more precursor thereof, one or more isoform thereof, and/or one or more fragment thereof which is indicative of an animal which has or is more likely than not to have an increased tolerance to heat, an increased resistance to ticks and/or a desirable coat texture.

In one embodiment, the method comprises comparing the level of activity of PRLR, one or more precursor thereof, one or more isoform thereof, and/or one or more fragment thereof against one or more standard.

In one embodiment, the standard comprises a level of activity of PRLR, one or more precursor thereof, one or more isoform thereof, and/or one or more fragment thereof which is associated with an animal having a substantially limited tolerance to heat and/or an undesirable coat texture and a higher level of activity of PRLR, one or more precursor thereof, one or more isoform thereof, and/or one or more fragment thereof in the animal compared to the standard infers that the animal will more likely than not have an increased tolerance to heat, an increased resistance to ticks, and/or a desirable coat texture.

In one embodiment, an animal is selected if it is inferred that it will more likely than not have an increased tolerance to heat, an increased resistance to ticks, and/or a desirable coat texture. In one embodiment, an animal is rejected if it is inferred not to be more likely than not to have an increased tolerance to heat, an increased resistance to ticks, and/or a desirable coat texture.

In one embodiment, the method is performed for the purpose of selecting or rejecting an animal for milk production. In one embodiment, the method is performed for the purpose of selecting or rejecting an animal for meat production. In one embodiment, the method is performed for the purpose of selecting or rejecting an animal for egg production. In one embodiment, the method is performed for the purpose of selecting or rejecting an animal for fur, hair, wool, skin, or feather production. In one embodiment, the method is performed for selecting or rejecting an animal for a desirable coat texture. In another embodiment, the method is performed for the purpose of selecting or rejecting an animal for breeding purposes. In one embodiment, the method is performed for the purpose of selecting or rejecting an animal for inclusion in a herd.

In a nineteenth aspect the invention provides a method for estimating the worth of an animal and/or its offspring, the method comprising at least the step of observing the level of activity of PRLR, one or more precursor thereof, one or more isoform thereof, and/or one or more fragment thereof.

In one embodiment, the method comprises comparing the level of activity of PRLR, one or more precursor thereof, one or more isoform thereof, and/or one or more fragment thereof against one or more standard.

In one embodiment, the standard comprises a level of activity of PRLR, one or more precursor thereof, one or more isoform thereof, and/or one or more fragment thereof which is associated with an animal having a substantially limited tolerance to heat and/or an undesirable coat texture and a higher level of activity of PRLR, one or more precursor thereof, one or more isoform thereof, and/or one or more fragment thereof in the animal compared to the standard infers that the animal and/or its offspring will more likely than not have an increased tolerance to heat, an increased resistance to ticks, and/or a desirable coat texture.

In a twentieth aspect, the invention provides a method for breeding animals, the method comprising at least the step of selecting a first animal identified to have a level of activity of one or more of PRLR, one or more precursor thereof, one or more isoform thereof, and/or one or more fragment thereof which is indicative of an animal which has or is more likely than not to have an increased tolerance to heat, an increased resistance to ticks and/or a desirable coat texture and mating said first animal with a second animal.

In another embodiment, the method further comprises selecting a second animal that is identified to have a level of activity of one or more of PRLR, one or more precursor thereof, one or more isoform thereof and/or one or more fragment thereof which is indicative of an animal which has or is more likely than not to have an increased tolerance to heat, an increased resistance to ticks and/or a desirable coat texture.

In one embodiment, the method comprises the step of observing the level of activity of one or more of PRLR, one or more precursor thereof, one or more isoform thereof, and/or one or more fragment thereof from the first and/or second animal to identify whether or not it has a level of activity one or more of PRLR, one or more precursor thereof, one or more isoform thereof, and/or one or more fragment thereof which is indicative of an animal which has or is more likely than not to have an increased tolerance to heat, an increased resistance to ticks and/or a desirable coat texture.

In one embodiment, the method comprises comparing the level of activity of one or more of PRLR, one or more precursor thereof, one or more isoform thereof and/or one or more fragment thereof to one or more standard.

In one embodiment, the standard comprises a level of activity of PRLR, one or more precursor thereof, one or more isoform thereof, and/or one or more fragment thereof which is associated with an animal having a substantially limited tolerance to heat and/or an undesirable coat texture and the first and/or second animal is selected where it is observed to have a higher level of activity of PRLR, one or more precursor thereof, one or more isoform thereof, and/or one or more fragment thereof compared to the standard.

In one embodiment, the first and/or second animal is selected if it is inferred to be more likely than not to have increased tolerance to heat, an increased resistance to ticks, and/or a desirable coat texture.

In one embodiment of any one or more of the seventeenth to twentieth aspects, the methods comprise at least the steps of:
  a) taking a sample from an animal;
  b) detecting the level of activity of one or more of PRLR, one or more precursor thereof, one or more isoform thereof, and/or one or more fragment thereof in the sample; and,
  c) comparing the level of activity of PRLR, one or more precursor thereof, one or more isoform thereof, and/or one or more fragment thereof against a standard.

In a twenty first aspect the invention provides a method for selecting or rejecting one or more cell or embryo the method comprising at least the step of observing the level of activity of PRLR, one or more precursor thereof, one or more isoform thereof, and/or one or more fragment thereof.

In one embodiment, one or more cell or embryo is selected it if has a level of activity of one or more of PRLR, one or more precursor thereof, one or more isoform thereof, and/or one or more fragment thereof which is indicative of an animal which has or is more likely than not to have an increased tolerance to heat, an increased resistance to ticks and/or a desirable coat texture. In one embodiment, one or more cell or embryo is rejected if it does not have a level of activity of one or more of PRLR, one or more precursor thereof, one or more isoform thereof, and/or one or more fragment thereof which is indicative of an animal which has or is more likely than not to have an increased tolerance to heat, an increased resistance to ticks and/or a desirable coat texture.

In one embodiment, the method comprises comparing the level of activity of PRLR, one or more precursor thereof, one or more isoform thereof, and/or one or more fragment thereof against one or more standard.

In one embodiment, the standard comprises a level of activity of PRLR, one or more precursor thereof, one or more isoform thereof, and/or one or more fragment thereof which is associated with an animal having a substantially limited tolerance to heat and/or an undesirable coat texture and a higher level of activity of PRLR, one or more precursor thereof, one or more isoform thereof, and/or one or more fragment thereof in the one or more cell or embryo, or an animal from which the one or more cell or embryo is derived, compared to the standard infers that the one or more cell or embryo is suitable for use in a method for breeding or cloning an animal which will more likely than not have an increased tolerance to heat, an increased resistance to ticks, and/or a desirable coat texture.

In one embodiment, one or more cell or embryo is selected if it, or an animal from which the one or more cell or embryo is derived, has a higher level of PRLR, one or more precursor thereof, one or more isoform thereof, and/or one or more nucleic acid encoding any one or more thereof.

In one embodiment, the method is performed for the purpose of selecting or rejecting one or more cell or embryo for use in cloning an animal and/or breeding an animal. In one embodiment, breeding an animal may involve IVF.

In a twenty second aspect, the invention provides a method for breeding animals, the method comprising at least the step of selecting a first gamete identified to have level of activity of one or more of PRLR, one or more precursor thereof, one or more isoform thereof, and/or one or more fragment thereof which is indicative of an animal which has or is more likely than not to have an increased tolerance to heat, an increased resistance to ticks and/or a desirable coat texture and fusing said first gamete with a second gamete to form a zygote.

In one embodiment, the method further comprises selecting the second gamete where it is identified to have level of activity of one or more of PRLR, one or more precursor thereof, one or more isoform thereof, and/or one or more fragment thereof which is indicative of an animal which has or is more likely than not to have an increased tolerance to heat, an increased resistance to ticks and/or a desirable coat texture.

In a twenty third aspect, the invention provides a method of breeding an animal, the method comprising at least the step of selecting an embryo where it is identified to have level of activity of one or more of PRLR, one or more precursor thereof, one or more isoform thereof, and/or one or more fragment thereof which is indicative of an animal which has or is more likely than not to have an increased tolerance to heat, an increased resistance to ticks and/or a desirable coat texture.

In a twenty fourth aspect, the invention provides a method of cloning an animal, the method comprising at least the step of selecting one or more cell where it is identified to have level of activity of one or more of PRLR, one or more precursor thereof, one or more isoform thereof, and/or one or more fragment thereof which is indicative of an animal which has or is more likely than not to have an increased tolerance to heat, an increased resistance to ticks and/or a desirable coat texture.

In one embodiment of the methods of the twenty second to twenty fourth aspects, the methods comprise the step of observing the level of activity one or more of PRLR, one or more precursor thereof, one or more isoform thereof, and/or one or more fragment thereof in said first and/or second gamete, one or more cell or embryo to identify whether or not it has a level of activity of one or more of PRLR, one or more precursor thereof, one or more isoform thereof, and/or one or more fragment thereof which is indicative of an animal which has or is more likely than not to have an increased tolerance to heat, an increased resistance to ticks and/or a desirable coat texture.

In one embodiment of the methods of the twenty second to twenty fourth aspect, the methods comprise comparing the level of one or more of PRLR, one or more precursor thereof, one or more isoform thereof, and/or one or more fragment thereof in said first and/or second gamete, embryo or one or more cells to one or more standard.

In one embodiment of any one of the twenty second to twenty fourth aspects, the standard comprises a level of activity of PRLR, one or more precursor thereof, one or more isoform thereof, and/or one or more fragment thereof which is associated with an animal having a substantially limited tolerance to heat and/or an undesirable coat texture and the first and/or second gamete, embryo or one or more cell is selected where it is observed to have a higher level of activity of PRLR, one or more precursor thereof, one or more isoform thereof, and/or one or more fragment thereof compared to the standard.

In a twenty fifth aspect, the invention provides a method for determining whether it is more likely than not that an animal and/or its offspring will have an increased tolerance to heat, an increased resistance to ticks, and/or a desirable coat texture, the method comprising at least the step of analysing one or more of PRLR, one or more precursor thereof, one or more isoform thereof, and/or one or more fragment thereof from said animal to determine whether or not it includes one or more variation in the amino acid sequence, wherein where the one or more of PRLR, one or more precursor thereof, one or more isoform thereof, and/or one or more fragment thereof has said one or more variation the animal and/or its offspring is determined to be more likely than not to have an increased tolerance to heat, an increased resistance to ticks, and/or a desirable coat texture.

In a twenty sixth aspect the invention provides a method for selecting or rejecting an animal, the method comprising at least the step of analysing one or more of PRLR, one or more precursor thereof, one or more isoform thereof, and/or one or more fragment thereof from said animal to determine whether or not it includes one or more variation in the amino acid sequence, wherein the presence of said one or more variation infers that the animal is more likely than not to have an increased tolerance to heat, an increased resistance to ticks, and/or a desirable coat texture.

In one embodiment, an animal is selected if it is inferred to be more likely than not to have increased tolerance to heat, an increased resistance to ticks, and/or a desirable coat texture. In one embodiment, an animal is rejected if it is inferred not to be more likely than not to have increased tolerance to heat, an increased resistance to ticks, and/or a desirable coat texture.

In one embodiment, an animal is selected if it includes one or more amino acid variation in PRLR, one or more precursor thereof, one or more isoform thereof, and/or one or more fragment thereof and an animal is rejected if it does not include one or more amino acid variation in PRLR, one or more precursor thereof, one or more isoform thereof, and/or one or more fragment thereof.

In one embodiment, the method is performed for the purpose of selecting or rejecting an animal for milk production. In one embodiment, the method is performed for the purpose of selecting or rejecting an animal for meat production. In one embodiment, the method is performed for the purpose of selecting or rejecting an animal for egg production. In one embodiment, the method is performed for the purpose of selecting or rejecting an animal for fur, hair, wool, skin, or feather production. In one embodiment, the method is performed for selecting or rejecting an animal for a desirable coat texture. In another embodiment, the method is performed for the purpose of selecting or rejecting an animal for breeding purposes. In one embodiment, the method is performed for the purpose of selecting or rejecting an animal for inclusion in a herd.

In a twenty seventh aspect, the invention provides a method for estimating the worth of an animal and/or its offspring, the method comprising at least the step of analysing one or more of PRLR, one or more precursor thereof, one or more isoform thereof, and/or one or more fragment thereof from said animal to determine whether or not it includes one or more variation in the amino acid sequence, wherein the presence of said one or more variation infers that the animal and/or its offspring is more likely than not to have an increased tolerance to heat, an increased resistance to ticks, and/or a desirable coat texture.

In a twenty eighth aspect, the invention provides a method for breeding animals, which method comprises at least the step of selecting at least a first animal that has been identified to have one or more variation in the amino acid sequence of one or more of PRLR, one or more precursor thereof, one or more isoform thereof, and/or one or more fragment thereof and mating said first animal with a second animal.

In one embodiment, the method further comprises selecting the second animal on the basis that it has been identified to have one or more variation in the amino acid sequence of one or more of PRLR, one or more precursor thereof, one or more isoform thereof, and/or one or more fragment thereof.

In one embodiment, the first and/or second animal is selected if it is inferred to be more likely than not to have increased tolerance to heat, an increased resistance to ticks, and/or a desirable coat texture.

In a twenty ninth aspect the invention provides a method for selecting or rejecting one or more cell or embryo, the method comprising at least the step of analysing one or more of PRLR, one or more precursor thereof, one or more isoform thereof, and/or one or more fragment thereof from said one or more cell or embryo, or from an animal from which the one or more cell or embryo is derived, to determine whether or not it includes one or more variation in the amino acid sequence. In one embodiment, the presence of such one or more variation infers that the one or more cell or embryo is suitable for use in a method for breeding or cloning an animal which is more likely than not to have increased tolerance to heat, an increased resistance to ticks, and/or a desirable coat texture.

In one embodiment, one or more cell or embryo is selected if it, or an animal from which the one or more cell or embryo is derived, has one or more variation in the amino acid sequence of PRLR. In one embodiment, one or more cell or embryo is rejected if it, or an animal from which the one or more cell or embryo is derived, does not have one or more variation in the amino acid sequence of PRLR.

In one embodiment, the method is performed for the purpose of selecting or rejecting one or more cell or embryo for use in cloning an animal and/or breeding an animal. In one embodiment, breeding an animal may involve IVF.

In a thirtieth aspect, the invention provides a method for breeding animals, the method comprising at least the step of selecting a first gamete that has one or more variation in the amino acid sequence of one or more of PRLR, one or more precursor thereof, one or more isoform thereof, and/or one or more fragment thereof and fusing said first gamete with a second gamete to form a zygote.

In one embodiment, the method further comprises selecting the second gamete on the basis that it has one or more variation in the amino acid sequence of one or more of PRLR, one or more precursor thereof, one or more isoform thereof, and/or one or more fragment thereof.

In a thirty first aspect, the invention provides a method of breeding an animal, the method comprising at least the step of selecting an embryo that has one or more variation in the amino acid sequence of one or more of PRLR, one or more precursor thereof, one or more isoform thereof, and/or one or more fragment thereof.

In a thirty second aspect, the invention provides a method of cloning an animal, the method comprising at least the step of selecting one or more cell that has one or more variation in the amino acid sequence of one or more of PRLR, one or more precursor thereof, one or more isoform thereof, and/or one or more fragment thereof.

In one embodiment of any one of the twenty fifth to thirty second aspects, one or more variation in the amino acid sequence is one which results in an increase in PRLR activity.

In one embodiment of any one of the twenty fifth to thirty second aspects, one or more variation is a substitution of one or more amino acid, deletion of one or more amino acid, and/or addition of one or more amino acid. In one particular embodiment, one or more variation in the amino acid sequence is a deletion resulting in truncation of PRLR.

In one embodiment of any one of the twenty fifth to thirty second aspects, one or more amino acid variation is located within a region from a position corresponding to amino acid 430 to amino acid 490 of PRLR of *Bos Taurus*. In one embodiment, one or more variation results in a truncation of PRLR in a region from approximately an amino acid position corresponding to position 430 to an amino acid position corresponding to position 490 of PRLR of *Bos Taurus*.

In one embodiment of any one of the twenty fifth to thirty second aspects one or more amino acid variation comprises an alanine to valine substitution at a position corresponding to amino acid position 461 of PRLR of *Bos Taurus*. In one embodiment, one or more amino acid variation results in a truncation of PRLR to a position corresponding to amino acid position 461 of PRLR of *Bos Taurus*. In one embodiment, one or more amino acid variation is a substitution of an alanine with a valine at position 461 and truncation of PRLR to a position corresponding to amino acid position 461 of PRLR of *Bos Taurus*.

In a thirty third aspect, the invention provides a method for generating an animal which is more likely than not to have an increased tolerance to heat, an increased resistance to ticks, and/or a desirable coat texture, the method comprising at least the step of introducing one or more genetic alteration to the PRLR gene of one or more cell used to generate the animal. In a related aspect, the invention also provides a method for generating one or more cells which may be of use in generating an animal which is more likely than not to have an increased tolerance to heat, an increased resistance to ticks, and/or a desirable coat texture, the method comprising at least the step of introducing one or more genetic alteration to the PRLR gene of one or more cell. In another aspect, the invention provides a cell generated by said method.

In one embodiment, the method for generating the animal involves IVF. In one embodiment, the method for generating the animal is a cloning method.

In one embodiment, one or more genetic alteration is one which increases the activity of PRLR. In one embodiment, one or more genetic alteration includes a genetic alteration located within a region bounded by nucleotides corresponding to positions 39136469 and 39136649 of chromosome 20 of *Bos Taurus*. In one embodiment, one or more genetic alteration is a genetic alteration located in the final exon of the PRLR gene. In one embodiment, one or more genetic alteration includes a genetic alteration at a position corresponding to position 39136559 on chromosome 20 of *Bos Taurus*. In one embodiment, one or more genetic alteration includes a deletion of a C at the position corresponding to position 39136559 on chromosome 20 of *Bos Taurus*.

In one embodiment, the one or more cell is chosen from a gamete or a zygote. In one embodiment, the one or more cell is a somatic cell or a cell from a cell line.

In one embodiment, a cloning method of the thirty third aspect further comprises the step of selecting or rejecting one or more animal, cell or embryo using a method of any one or more of the methods of the second, fifth, tenth, thirteenth, eighteenth, twenty first, twenty sixth or twenty ninth aspects of the invention.

In one embodiment, an IVF method of the thirty third aspect further comprises the step of selecting or rejecting one or more animal, cell or embryo using a method of any one or more of the methods of the second, fifth, tenth, thirteenth, eighteenth, twenty first, twenty sixth or twenty ninth aspects of the invention.

In a related aspect, the invention provides an animal generated by a method of the thirty third aspect of the invention.

In a thirty fourth aspect, the invention provides a method of forming a herd the method comprising at least the steps of:
 a. performing a method of any one or more of the first, second, third, fourth, ninth, tenth, eleventh, twelfth, seventeenth, eighteenth, ninteenth, twentieth, twenty fifth, twenty sixth, twenty seventh or twenty eighty aspects of the invention;
 b. selecting or rejecting an animal based on the results of step a); and,
 c. forming a herd of selected animals.

In one embodiment, an animal is rejected if it is inferred not to be more likely than not to have an increased tolerance to heat, an increased resistance to ticks, and/or a desirable coat texture. In one embodiment, an animal is selected if it is inferred to be more likely than not to have an increased tolerance to heat, an increased resistance to ticks, and/or a desirable coat texture.

In one embodiment, an animal is selected if it includes one or more genetic variation in the PRLR gene and/or includes one or more genetic marker in linkage disequilibrium therewith. In one embodiment, an animal is selected if it includes one or more variation in the amino acid sequence of PRLR, one or more precursor thereof, one or more isoform thereof, and/or one or more fragment thereof. In one embodiment, an animal is selected if it has a higher level of PRLR, one or more precursor thereof, one or more isoform thereof, one or more fragment thereof and/or a nucleic acid encoding any one or more thereof compared to a standard, wherein the standard comprises a level of PRLR, one or more precursor thereof, one or more isoform thereof, one or more fragment thereof and/or a nucleic acid encoding any one or more thereof which is associated with an animal having a substantially limited tolerance to heat and/or an undesirable coat texture. In one embodiment, an animal is selected if it has a higher level of activity of PRLR, one or more precursor thereof, one or more isoform thereof, and/or one or more fragment thereof compared to a standard, wherein the standard comprises a level of activity of PRLR, one or more precursor thereof, one or more isoform thereof, and/or one or more fragment thereof which is associated with an animal having a substantially limited tolerance to heat and/or an undesirable coat texture.

In a related aspect, the invention provides a herd formed by a method of the thirty fourth aspect of the invention.

In a thirty fifth aspect, the invention provides a method for identifying one or more genetic variation in the PRLR gene which infers an increased tolerance to heat, an increased resistance to ticks, and/or a desirable coat texture in an animal. In one embodiment, the method comprises identifying one or more genetic variation in the PRLR gene and determining whether or not it results in an increase in the level or activity of PRLR. In one embodiment, where the one or more alteration results in an increase in the level or activity of PRLR it is determined to infer an increased tolerance to heat, an increased resistance to ticks, and/or a desirable coat texture in an animal.

In a thirty sixth aspect, the invention provides a method for identifying whether or not an animal (and/or its offspring), one or more cells or embryo has or may have one or more genetic alteration which is linked to an increased tolerance to heat, an increased resistance to ticks, and/or a desirable coat texture the method comprising observing the nucleic acid sequence to identify whether or not it includes one or more of the genetic variation in the PRLR gene and/or a genetic marker in linkage disequilibrium therewith. Where the nucleic acid sequence is identified to have one or more genetic variation in the PRLR gene and/or a genetic marker in linkage disequilibrium therewith, the animal, cell or embryo is identified as having one or more genetic alteration that is linked to an increased tolerance to heat, an increased resistance to ticks, and/or a desirable coat texture. In one embodiment, the one or more genetic alteration results in an increase in the level or activity of PRLR.

In a thirty seventh aspect, the invention provides a method for identifying one or more amino acid variation in PRLR which infers an increased tolerance to heat, an increased resistance to ticks, and/or a desirable coat texture in an animal. In one embodiment, the method comprises identifying one or more amino acid variation in PRLR and determining whether or not it results in an increase in the level or activity of PRLR. In one embodiment, where the one or more alteration results in an increase in the level or activity of PRLR it is determined to infer an increased tolerance to heat, an increased resistance to ticks, and/or a desirable coat texture in an animal.

In a thirty eighth aspect, the invention provides a method for identifying whether or not an animal (and/or its offspring), one or more cell or embryo has or may have one or more amino acid variation which is linked to an increased tolerance to heat, an increased resistance to ticks, and/or a desirable coat texture the method comprising observing the amino acid sequence to identify whether or not it includes one or more variation in the amino acid sequence of PRLR., one or more precursor thereof, one or more isoform thereof or one or more fragment thereof. Where it is identified that the animal, cell or embryo has one or more of the variation in the amino acid sequence of PRLR, one or more precursor thereof, one or more isoform thereof, or one or more fragment thereof the animal, cell or embryo is identified as having one or more amino acid variation that is linked to an increased tolerance to heat, an increased resistance to ticks, and/or a desirable coat texture. In one embodiment, the one or more amino acid variation results in an increase in the level or activity of PRLR, one or more precursor thereof, one or more isoform thereof or one or more fragment thereof.

In one embodiment of any one or more of the first to thirty eighth aspects of the invention, the animal is a mammal. In certain embodiments, the animal is from the Bovidae family, Phasianidae family, or Suidae family. In certain embodiments, the animal is of a genus, species or breed as herein after described. In one particular embodiment, the animal is bovine. In a particular embodiment the bovine animal is *Bos taurus* or *Bos indicus*. In a particular embodiment, the animal is chosen from the group consisting Jersey, Holstein, Friesian or crossbred dairy cattle. In other embodiments, the animal is chosen from the group consisting Creole including Romosinuano, Criollo, Carora, Senepol or crossbred cattle.

In one embodiment, the methods of any one or more of the first to thirty eighth aspects of the invention further comprise analysis of one or more additional biological markers. In one embodiment, the one or more biological markers are one or more genetic markers.

In one embodiment, a methods of the invention may comprise two or more of: analysing a nucleic acid to determine whether or not it includes one or more genetic variation in the PRLR gene and/or includes one or more genetic marker in linkage disequilibrium therewith; observing the level of one or more of PRLR, one or more precursor thereof, one or more isoform thereof, one or more fragment thereof, and/or one or more nucleic acid encoding any one or more thereof; observing in the animal the level of activity of PRLR, one or more precursor thereof, one or more isoform thereof, and/or one or more fragment thereof; and, analysing one or more of PRLR, one or more precursor thereof, one or more isoform thereof, and/or one or more fragment thereof from said animal to determine whether or not it includes one or more variation in the amino acid sequence. Such analysis and observation may be performed using one or more methods of the aspects of the invention described herein before.

In another aspect, the invention provides an isolated nucleic acid encompassing a del(C) alteration at a position corresponding to position 39136559 of chromosome 20 of *Bos Taurus*. In one embodiment, the invention provides an isolated nucleic acid in which the C is present at a position corresponding to position 39136559 of chromosome 20 of *Bos Taurus*. In another embodiment the nucleic acid comprises a nucleotide sequence in which the C at a position corresponding to position 39136559 of chromosome 20 of *Bos Taurus* has been deleted. In one embodiment, the invention provides an isolated nucleic acid comprising or consisting of the sequence GACCAAACAGACCAACAT-GTTTAAAAGCCTCAAAAACCA (SEQ ID No. 3) or a functionally equivalent variant thereof. In another embodiment, the invention provides an isolated nucleic acid comprising or consisting of the sequence of SEQ ID No. 6 or a functionally equivalent variant thereof.

In one aspect, the invention provides a cDNA comprising one or more genetic marker described herein.

In another aspect, the invention provides one or more additional nucleic acids as described further herein after.

In another aspect, the invention provides an isolated peptide as described herein. In one embodiment the invention provides an isolated peptide comprising or consisting of the sequence of SEQ ID No. 7 or a functionally equivalent variant thereof.

In other aspects, the invention provides:
An animal selected by a method of any one or more of the second, tenth, eighteenth, and twenty sixth aspects;
One or more cell or embryo selected by a method of any one or more of the fifth, thirteenth, twenty first and twenty ninth aspects;
Offspring or an animal produced by a method of any one or more of the fourth, sixth, seventh, eighth, twelfth, fourteenth, fifteenth, sixteenth, twentieth, twenty second, twenty third, twenty fourth, twenty eighth, thirtieth, thirty first, and thirty second aspects.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

FIGURES

These and other aspects of the present invention, which should be considered in all its novel aspects, will become apparent from the following description, which is given by way of example only, with reference to the accompanying figures, in which:

FIG. 1: Illustrates the nucleotide sequence of *Bos taunts* prolactin receptor (PRLR), transcript variant 2, mRNA (NCBI Reference Sequence: NM_001039726.2). PRLR long-form. Translated region is highlighted. Start codon beginning at position 85 corresponds to position 39115293 on UMD 3.1. Exon 1 as published by NCBI starts at 39115245. Stop codon beginning at position 1828 in mRNA sequence is at position 39136922 in genome build UMD3.1. The base deletion identified in DNA from Senepol cattle is at position 1466 in mRNA sequence (highlighted) and genomic position 39136559. The resulting frameshift codes for a valine followed by a stop codon resulting in protein truncation (FIG. 2).

FIG. 2: *Bos taurus* prolactin receptor (PRLR), transcript variant 2, mRNA.

Product is PRLR long-form (NCBI Reference Sequence: NM_001039726.2). The frame-shift mutation observed by the inventors will result in truncation of the protein from 581 amino acids to 461 amino acids through removal of the sequence highlighted and conversion of the new carboxy terminal amino acid from alanine to valine.

FIG. 3: *Bos taurus* prolactin receptor (PRLR), transcript variant 2, mRNA, showing alteration identified by the inventors—base deleted (at 39136559 on BTA20) in Senepol PRLR (c) is indicated by omission. Product is the PRLR long-form (NCBI Reference Sequence: NM_001039726.2).

FIG. 4: Predicted amino acid sequence (n461) of Senepol prolactin receptor as a result of the base C deletion at position 39136559 of *Bos Taurus* BTA 20.

FIG. 5: Illustrates the nucleotide sequence of *Bos taurus* prolactin receptor (PRLR), transcript variant 2, mRNA (NCBI Reference Sequence: NM_001039726.1). PRLR long-form. Translated region is highlighted. Start codon beginning at position 87 corresponds to position 39115293 on UMD 3.1. Exon 1 as published by NCBI starts at 39115245. Stop codon beginning at position 1830 in mRNA sequence is at position 39136922 in genome build UMD3.1. The base deletion identified in DNA from Senepol cattle is at position 1468 in mRNA sequence (highlighted) and genomic position 39136559. The resulting frameshift codes for a valine followed by a stop codon resulting in protein truncation (FIG. 2).

PREFERRED EMBODIMENT(S)

The following is a description of the present invention, including preferred embodiments thereof, given in general terms. The invention is further elucidated from the disclosure given under the section "Examples" which provides, inter alia, experimental data supporting the invention.

The inventors have identified that particular alleles of a genetic marker located in the prolactin receptor (PRLR) gene in a region of chromosome 20 in *Bos taurus* is associated with the very short, sleek hair coats observed in the Senepol breed of cattle who have increased heat tolerance. This is the first time that an alteration in the PRLR gene has been directly associated with the short and sleek hair coat and heat tolerance traits of cattle. Accordingly, the inventors contemplate that any genetic alteration in the PRLR gene, particularly those which result in an increase in the activity of PRLR, may be used as a marker to determine whether an animal is more likely than not to have an increased tolerance to heat. Accordingly, while the description which follows may focus on the analysis of the nucleotide sequence at a particular position in this gene, it should be understood to extend to the analysis of the nucleotide sequence at any other position within the gene.

The inventors also contemplate that the analysis of one or more genetic marker which is in linkage disequilibrium with such an alteration in the PRLR gene may also be used for the same purpose. In addition, haplotypes including a combination of two or more such genetic alterations and/or markers in linkage disequilibrium therewith may also be used for this purpose.

Further, the inventors contemplate that methods for determining whether an animal (and/or its offspring) is more likely than not to have an increased tolerance to heat could comprise observing the level of PRLR, one or more isoform, one or more precursor, one or more fragment and/or one or more nucleic acid encoding any one or more thereof, where in one embodiment an increase in the level of any one or more of these molecules infers it is more likely than not that it will have an increased tolerance to heat. In addition, the inventors contemplate methods involving observing the activity of PRLR (including reference to one or more isoform, one or more precursor, one or more fragment and/or one or more nucleic acid encoding any one or more thereof), where in one embodiment an increase in the level of activity of PRLR (including reference to one or more isoform, one or more precursor, one or more fragment and/or one or more nucleic acid encoding any one or more thereof) infers that the animal will more likely than not have an increased tolerance to heat.

In addition, to the extent that certain genetic variations or alterations result in changes in the amino acid sequence of PRLR, the inventors contemplate that methods for determining whether an animal (and/or its offspring) is more likely than not to have an increased tolerance to heat could comprise observing whether or not these molecules include one or more variation in their amino acid sequence. It should be appreciated that this could include observing a size variation in PRLR (including reference to one or more precursors, isoforms, fragments thereof, and/or a nucleic acid encoding any one or more thereof).

Analysis of one or more biological marker of relevance to PRLR in accordance with the invention could also be used for selecting or rejecting one or more cell or embryo. Such analysis may aid in methods for breeding or cloning animals, for example.

While the invention is described herein in terms of determining or inferring whether or not an animal and/or its offspring is more likely than not to have an increased tolerance to heat, it should be appreciated that it is equally applicable to methods of determining or inferring whether or not an animal and/or its offspring is more likely than not to have a decreased or substantially no increase in tolerance to heat. The description herein (including all aspects and embodiments of the invention) should be read accordingly to encompass this.

In addition to the use of the method of the invention for determining or inferring whether or not an animal and/or its offspring is more likely than not to have an increased tolerance to heat, the inventors contemplate the methods of the invention being useful for determining or inferring whether or not an animal and/or its offspring is more likely than not to have a desirable coat texture (such as a short and sleek coat in cattle) as this is associated with the phenotype observed in Senepol cattle and linked to heat tolerance. In addition, the inventors contemplate the methods of the invention being useful for determining or inferring whether or not an animal and/or its offspring is more likely than not to have a level of resistance to ticks. Tick resistance is associated with coat type, shorter coats enhancing tick resistance and long coats increasing tick infestation, and tick resistance is associated with Senepol cattle. Accordingly, while the methods of the invention may be described herein in relation to increased tolerance to heat, it should be understood that these methods (including all aspects and embodiments of the invention) may alternatively or in addition be used for the purpose of determining or inferring whether or not an animal and/or its offspring is more likely than not to have a desirable coat texture and/or a level of tick resistance or an increased resistance to ticks. The description should be read accordingly to encompass such alternative or additional methods.

In certain embodiments, "desirable coat texture" includes a thin, light, sleek and/or short coat. For example: in the case of the Bovidae and *Capra* families a "desirable coat texture" may be short and sleek; in the case of the *Ovis* family, a "desirable coat texture" may be short, thin and/or light; in the case of the Suidae family, a "desirable coat texture" may be short, thin and/or light; in the case of the Phasiadnidae family, "a desirable coat texture" may be thin and/or light feathering. In certain embodiments, an "undesirable coat texture" is one which is associated with an animal have substantially limited tolerance to heat. An "undesirable coat texture" may include a thick, heavy, rough and/or long coat.

Analysis of one or more biological marker in accordance with the invention may assist in, for example: predicting phenotypic performance, including use in production management systems known as Marker Assisted Selection; the selection or rejection of animals for breeding purposes; the selection or rejection of animals for milk production, meat production, egg production, fur, hair, wool, skin, or feather production, and/or desirable coat texture; managing animals in order to maximise their individual potential performance and value; estimating the worth or economic value of an animal; improving profits related to selling animals and/or products produced from the animals; improving the genetics of a population of animals by selecting and breeding desirable animals; generating and maintaining herds of animals; cloning animals likely to have or not have a specific trait; predicting the suitability of an animal and/or its offspring to use in different industries and/or environments and/or breeding programmes or cloning. Animals more or less suitable for a particular production system, industry or environment can be tested or screened to predict life time performance and segregated or managed to suit their genotype and therefore predicted phenotype. Animals may be tested or screened at any time during their life, including but not limited to early at birth, as gametes, zygotes, embryos, foetuses.

The identification by the inventors that an alteration in the PRLR gene is associated with heat tolerance and desirable coat texture (for example short and sleek hair coat in cattle) also allows for generation of animals having such desirable phenotypes using cloning and/or gene editing processes in which one or more specific genetic alteration is introduced into the PRLR gene. For example, one or more specific alteration may be introduced into individual gametes or a zygote during an IVF programme or in to one or more relevant cells during a cloning procedure. Accordingly, the invention should be taken to include methods for generating animals which are more likely than not to have increased tolerance to heat, an increased resistance to ticks, and/or a desirable coat texture.

While the inventors have identified the markers of relevance to the invention in bovine animals, they contemplate that the methods of the invention are equally applicable to a variety of different animals (as is described herein after), including, but not limited to, cattle, sheep, goats, chickens and pigs.

DEFINITIONS

The term "biological marker(s)" as used herein should be taken broadly and includes, for example, one or more genetic marker, the level of one or more protein (including reference to one or more fragments thereof, one or more precursors thereof, one or more isoforms thereof) or a nucleic acid encoding one or more protein (including reference to one or more fragments thereof, one or more precursors thereof, one or more isoforms thereof), the level of expression of one or more gene or protein (including reference to one or more fragments thereof, one or more precursors thereof, one or more isoforms thereof), the level of activity of one or more protein (including reference to one or more fragments thereof, one or more precursors thereof, one or more isoforms thereof) and/or variation in the amino acid sequence of a protein (including reference to one or more fragments thereof, one or more precursors thereof, one or more isoforms thereof) which may include observation of the size of a protein ((including reference to one or more fragments thereof, one or more precursors thereof, one or more isoforms thereof).

The term "genetic marker" as used herein refers to nucleic acids or specific genetic loci (including specific nucleotide positions) that are polymorphic or contain sequence alterations or variations within a population, the alleles of which can be detected and distinguished by one or more analytic methods.

The term "genetic marker" further includes within its scope a plurality of genetic markers co-segregating, in the form of a "haplotype". In this context, the term "haplotype" refers to a plurality of genetic markers that are generally inherited together. Typically, genetic markers within a haplotype are in linkage disequilibrium. The term "genetic marker" of "genetic marker of the invention" and like terms, may be used herein to describe one or more genetic variation in the PRLR gene in accordance with the invention.

Reference herein to analysing a nucleic acid to determine the nucleotide sequence of a "genetic marker" or at a particular genetic position or the presence or absence or nature of one or more genetic variation should be taken to include analysing and determining the nucleotide sequence on either strand of the nucleic acid. Skilled persons will readily be able to determine the nucleotide or base on an opposing strand based on well understood structure of DNA molecules: C pairs with G, A pairs with T. Accordingly, if reference is made to identifying the presence of a T at a particular position, it should be taken to include reference to identifying the presence of an A on the opposing strand of the DNA, and vice versa. Similarly, if reference is made to identifying the presence of a G at a particular position, it should be taken to include reference to identifying the presence of a C on the opposing strand of DNA, and vice versa.

The term "single nucleotide polymorphism" (SNP) refers to nucleic acid sequence variations that occur when a single nucleotide in the genome sequence is altered. A single nucleotide polymorphism may also be a single nucleotide insertion or deletion. The different nucleotides within a SNP are referred to as an allele.

The term "genotype" as used herein means the genetic constitution or nucleotide sequence at one or more genetic locus, in particular the nucleotide sequence of an allele of a genetic locus.

"Linkage disequilibrium" should be taken broadly to refer to the tendency of the presence of an allele at one genetic locus to predict the presence of an allele at one or more other genetic loci (for example a distinct genetic marker). The genetic loci need not necessarily be on the same chromosome. However, in a preferred embodiment, the genetic loci are located on the same chromosome. In one particular embodiment of the invention, the marker in linkage disequilibrium with a genetic alteration in accordance with the invention is located on chromosome 20 of *Bos taurus* mapping to a region between positions of approximately 38.35 Mb to approximately 39.85 Mb. In one particular embodiment, the marker in linkage disequilibrium is located on chromosome 20 mapping to a region between positions of approximately 38.4 Mb to approximately 39.8 Mb. In another embodiment, the marker in linkage disequilibrium is located on chromosome 20 mapping to a region between positions of approximately 38.5 Mb to approximately 39.7 Mb.

One measure of linkage disequilibrium is $DELTA^2$, which is calculated using the formula described by Devlin et al (Genomics 29 (2):311-22 (1995)), and is a measure of how well an allele X at a first genetic locus predicts the occurrence of an allele Y at a second genetic locus. A $DELTA^2$ value of 1.0 indicates the prediction is perfect (for example, if Y is present then X is present). It should be appreciated that reference to linkage disequilibrium herein should not be taken to imply a $DELTA^2$ value of 1.0. In particular embodiments, the linkage disequilibrium between an allele at one genetic locus and an allele at a second genetic locus, has a $DELTA^2$ value of at least 0.75, at least 0.80, at least 0.85, at least 0.90, at least 0.95, and most preferably 1.0.

Skilled persons will readily appreciate methods for determining whether any two alleles are in linkage disequilibrium. However, by way of example, see Genetic Data Analysis II, Weir, Sinauer Associates, Inc. Publishers, Sunderland, Mass., 1996.

Where reference is made herein to analysing a nucleic acid to determine whether or not it includes a genetic marker in linkage disequilibrium with one or more genetic variation in the PRLR gene, it should be appreciated that such a genetic marker may be native to the genome (of an animal or one or more cell for example) or it may have been artificially generated or inserted. An "artificially generated or inserted" genetic marker is one which has been introduced in to the genome. Such genetic marker may comprise any one or more of a variety of genetic alterations, including for example, the addition of one or more nucleotide to the genome, substitution of one or more nucleotide within the genome with one or more nucleotide, and/or deletion of one or more nucleotide from the genome. In one particular embodiment, the genetic marker is a heterologous nucleic acid comprising one or more nucleotides which is inserted into the genome. Persons of general skill in the art to which the invention relates will readily appreciate methods for introducing such a genetic marker into the genome of an animal, including a variety of recombinant techniques including, for example gene editing methodology and site directed mutagenesis. Such techniques may be described, for example, in: Sambrook and Russell, Molecular Cloning: A Laboratory Manual, 2001, Cold Spring Harbor Laboratory Press, Cold Spring Harbor, New York; and, Precision Editing of Large Animal Genomes, Wenfang (Spring) Tan, Daniel F. Carlson, Mark W. Walton, Scott C. Fahrenkrug and Perry B. Hackett, Adv Genet. 2012; 80: 37-97. doi:10.1016/B978-0-12-404742-6.00002-8; and, One-Step Generation of Mice Carrying Mutations in Multiple Genes by CRISPR/Cas-Mediated Genome Engineering, Haoyi Wang, Hui Yang, Chikdu S. Shivalila, Meelad M. Dawlaty, Albert W. Cheng, Feng Zhang, and Rudolf Jaenisch. *Cell*. 2013 May 9; 153(4): 910-918. doi:10.1016/j.cell.2013.04.025. By way of example only, such genetic marker may have been introduced into the genome of one or more cell to be tested, the genome of one or more cell of an ancestor of an animal, or the genome of one or more cell of an animal to be tested.

A "varation in the amino acid sequence" of PRLR, isoforms, fragments and/or precursors thereof should be considered broadly to include any change in the amino acid sequence. By way of example only, it should be taken to include subsitution of any one or more amino acid, addition of one or more amino acid and/or deletion of one or more amino acid.

A "genetic variation" should also be considered broadly to include any change in the nucleotide sequence. By way of example only, it should be taken to include subsitution of any one or more nucleotide, addition of one or more nucleotide and/or deletion of one or more nucleotide.

Where the invention is described in terms of identifying or determining whether or not a nucleic acid includes one or more genetic variation or a peptide or protein includes one or more variation in the amino acid sequence, it should be appreciated that such variation is a difference in the nucleic acid or amino acid sequence compared to the nucleic acid sequence associated with one or more animal which has a substantially limited tolerance to heat, a substantially limited resistance to ticks and/or an undesirable coat texture or does not have an increased tolerance to heat, an increased resistance to ticks, and/or a desirable coat texture. Typically, the variation will be determined in relation to a reference sequence. In certain embodiments, the reference sequence is a nucleic acid encoding part or all of a PRLR gene and/or one or more genetic marker in linkage disequilibrium therewith and the amino acid sequence of PRLR, an isoform, a precursor or a fragment thereof, which is associated with an animal that has substantially limited tolerance to heat, a substantially limited resistance to ticks and/or an undesirable coat texture, as defined herein. In one embodiment, the nucleic acid reference sequence is SEQ ID No.4 or a part thereof. In one embodiment, the amino acid reference sequence is SEQ ID No. 5 or a part thereof. In other embodiments, the reference sequence could be a nucleic acid or peptide or protein having a sequence which is already known to be associated with an increased tolerance to heat, an increased resistance to ticks, and/or a desirable coat texture, as defined herein. Accordingly, reference to "variation" should not be restricted to mean that the nucleic acid, peptide or protein being analysed is different from the reference sequence.

Reference to truncation of a protein or peptide "to a position corresponding to position Z", and like phrases, are intended to mean that the protein or peptide ends at position Z.

Reference to a region "bounded by" specific nucleotides or amino acids should be taken to mean a region comprising said nucleotides or amino acids. In other words, the region includes the terminal nucleotides or amino acids referred to. For example, a region "bounded by" nucleotides at position 39136469 and 39136649 includes the nucleotides present at position 39136469 and 39136649.

A "genetic alteration or variation which results in an increase in the activity of PRLR" may be any genetic change which has an affect on the level, expression or activity of the PRLR gene product (including reference to isoforms, fragments and/or precursor thereof). By way of example, it may increase the level of expression or alter the structure or function of the gene product. Similarly, a "variation in the amino acid sequence which results in an increase in the activity of PRLR", or like phrases, may be any change that has an affect on the level or activity of PRLR (including reference to isoforms, fragments and/or precursor thereof). The term "increase" should not be taken to imply any particular level of activity or function, all that is required is that there is at least some increase in activity compared to an animal or animals not having the variation or alteration (including reference to the same animal if it did not have a biological marker according to the invention).

In general, where reference is made to an "increase" or "decrease" in the level or activity of PRLR, an isoform thereof, a fragment thereof, a precursor thereof, and/or a nucleic acid encoding any one or more thereof it should be taken broadly to include any increase or decrease in said level compared to a reference animal or animals or a standard. Reference may also be made herein to a "higher" or a "lower" level or activity of PRLR, an isoform thereof, a fragment thereof, a precursor thereof, and/or a nucleic acid encoding any one or more thereof compared to a reference animal or animals or a standard. This should not be taken to imply a particular level or activity of PRLR, an isoform thereof, a fragment thereof, a precursor thereof, and/or a nucleic acid encoding any one or more thereof. One can readily determine whether a variation results in an increase or decrease in the level or activity of PRLR or a higher or lower level or activity of PRLR compared to a standard using standard assays known in the art, including those techniques exemplified herein after.

In one embodiment, the inventors contemplate at least an approximately 20% higher level or activity of PRLR compared to an animal or animals which do not have the desired phenotype (an increased tolerance to heat, an increased resistance to ticks, and/or desirable coat texture) may be indicative of an animal who does have a desirable phenotype (an increased tolerance to heat, an increased resistance to ticks, and/or a desirable coat texture).

Reference to the "PRLR gene" should be taken to include reference to the coding and non-coding regions of the gene, including upstream and downstream regulatory elements. The PRLR gene has been reported to be transcribed into two mRNA forms which differ in length; a short form and a long form. Accordingly, the "PRLR gene" may be referred to herein using terms such as "long form" or "short form", meaning the gene is transcribed into the long or short form mRNA, respectively. Reference to the specific location of a genetic alteration within the PRLR gene (for example, in the final exon) should be read having regard to the long form. However, general reference to the PRLR gene should be taken to include reference to both the short and the long form, unless otherwise specified. In one preferred embodiment of the invention, the PRLR gene is the long form.

"PRLR" is the prolactin receptor. Reference herein to "PRLR" should be taken to include reference to a precursor of PRLR, an isoform of PRLR and/or a fragment of PRLR unless the context requires otherwise. By way of example, methods of the invention may involve the analysis of the sequence, level, and/or activity of PRLR, an isoform of PRLR, a precursor of PRLR and/or a fragment of PRLR and/or a nucleic acid encoding any one or more thereof. In addition, PRLR is known to exist in two common isoforms, the long for and the short form. Reference herein to PRLR should be taken to include reference to both these forms. However, in one preferred embodiment, PRLR is the long form.

A "functionally equivalent variant" of any particular nucleic acid referred to herein should be taken broadly to encompass any nucleic acid whose nucleic acid sequence may vary from the specific sequence provided but which nucleic acid retains substantially the same function; for example, in the case of an oligonucleotide used to detect a genetic marker of the invention, the ability to bind to a particular target nucleic acid or prime a particular reaction with the desired specificity). The phrase "functionally equivalent" should not be taken to imply that the variant has the same level of activity as the nucleic acid of which it is a variant, although this may be desired. In one embodiment, "functionally equivalent variants" of any particular nucleic acid will have at least approximately 80%, approximately 90%, approximately 95%, or approximately 99% sequence homology or identity to the nucleic acid of which it is a variant.

A "functionally equivalent variant" of any particular peptide or protein referred to herein should be taken broadly to encompass any peptide or protein whose amino acid sequence may vary from the specific sequence provided but which peptide or protein retains substantially the same function. The phrase "functionally equivalent" should not be taken to imply that the variant has the same level of activity as the peptide or protein of which it is a variant, although this may be desired. In one embodiment, "functionally equivalent variants" of any particular peptide or protein will have at least approximately 80%, approximately 90%, approximately 95%, or approximately 99% sequence similarity or identity to the peptide or protein of which it is a variant.

The term "animal" should be taken broadly to include a variety of different animals. In one embodiment the "animal" is a mammal. In one particular embodiment, the animal is from the Bovidae family, the Phasianidae family, or the Suidae family.

In one embodiment, an animal from the Bovidae family is from the Bovinae subfamily. In one embodiment, the animal is of the *Bos* genus. In certain embodiments the animal is *Bos taurus* or *Bos indicus*. In one particular embodiment the animal is a beef and/or dairy breed. By way of further example, the animal may be chosen from the group of animals including, but not limited to, Jersey, Holstein, Friesian, Ayrshire, crossbred dairy cattle, Angus, Hereford, Simmental and crossbred beef cattle. In other embodiments, the animal is chosen from the group of the Creole breeds of cattle, including Romosinuano, Criollo, Carora, Senepol and crossbred dairy or beef cattle. In one particular embodiment, the animal is a crossbreed between a breed of animal known to have an increased tolerance to heat, an increased resistance to ticks, and/or a desirable coat texture and a breed of animal known to have substantially limited tolerance to heat, a substantially limited resistance to ticks, and/or an undesirable coat texture. Skilled persons will readily appreciate a variety of other species and breeds that the invention may be applied to.

In another embodiment, an animal from the Bovidae family is from the Caprinae subfamily. In one embodiment, the animal is of the *Capra* genus. In certain embodiments, the animal is *Capra* hircus. In one embodiment, the animal is a breed used for dairy, meat and/or wool farming and production. In certain embodiments, the animal may be chosen from the group of animals including, but not limited to Saanen, Alpine, Nubian, Boer and Cashmere. In another embodiment, the animal is of the *Ovis* genus. In certain embodiments, the animal is *Ovis aries*. In one embodiment, the animal is a breed used for dairy, meat and/or wool farming and production. In certain embodiments, the animal may be chosen from the group of animals including but not limited to Border Leicester, Merino, Wiltshire, Dorset, East Friesian, and Lacaune. Skilled persons will readily appreciate a variety of other species and breeds that the invention may be applied to.

In one embodiment, an animal from the Suidae family is from the Suinae subfamily. In one embodiment, the animal is of the *Sus* genus. In certain embodiments the animal is *Sus scrofa*. In one embodiment, the animal is a breed used for meat and/or leather farming and production. In certain embodiments, the animal may be chosen from the group of animals including, but not limited to, Landrace, Duroc, Meisham, Berkshire, and Philippine native. Skilled persons will readily appreciate a variety of other species and breeds that the invention may be applied to.

In one embodiment, an animal from the Phasiadnidae family is from the Phasianinae subfamily. In one embodiment, the animal is of the *Gallus* genus. In certain embodiments the animal is *Gallus gallus*. In one embodiment, the animal is a breed used for meat, feather and/or egg farming and production. In certain embodiments, the animal may be chosen from the group of animals including, but not limited to, Namtam, Leghorn, Silkie, and Wyandotte. Skilled persons will readily appreciate a variety of other species and breeds that the invention may be applied to.

The invention may be described herein by reference to a "herd" of animals. This term should be taken broadly to include any group of animals of the same species. The term should be taken to encompass other collective nouns used to refer to a group of animals of any particular species, such as a "flock" or a "drove".

"Increased tolerance to heat", "increased heat tolerance" and like phrases should be taken broadly to mean that an animal is better able to maintain or regulate body temperature under heat stress than an animal that does not have a genetic alteration or other biological marker as described herein. In one embodiment, the animal has a lower average body temperature under heat stress than an animal that does not have a biological marker in accordance with the invention (including reference to the same animal if it did not have a biological marker in accordance with the invention).

As used herein "substantially limited tolerance to heat" and like phrases means that the animal has a limited or substantially no capacity to maintain or regulate its body temperature under heat stress. In one embodiment, the animal will have a higher average body temperature under heat stress than an animal that has a biological marker in accordance with the invention (including reference to the same animal if it had a biological marker in accordance with the invention).

"Heat Stress" as used herein, should be taken broadly to mean exposure to a temperature of at least approximately 25° C. The temperature may be calculated as a composite temperature taking into account any one or more of air temperature, humidity, radiant heat, and convection heat using known methods. In one embodiment, "heat stress" includes exposure to a Temperature Humidity Index (THI) of approximately 72.

The use of "coat" herein should be taken to include reference to fur, hair, wool, or feathers, as the case may be for a particular animal.

"Tick resistance", "resistance to ticks" and like terms should be taken broadly to describe the ability of an animal to resist ticks, limit the number of ticks carried on the coat and/or limit the number of ticks that survive to maturity compared to an animal that does not have a biological marker as described herein (including reference to the same animal if it did not have a biological marker in accordance with the invention). It should not be taken to mean that absolutely no ticks will affect, infest or attack an animal or that no ticks will survive to maturity. In one embodiment, the presence of a biological marker of the invention infers at least some level of "increased" resistance to ticks. This should be taken broadly to mean that an animal is better able to resist ticks, including, for example, a reduction in ticks carried on the coat, a reduction in tick attack or infestation, and/or a lower number of ticks surviving to maturity compared to an animal that does not have a biological marker described herein (including reference to the same animal if it did not have a biological marker in accordance with the invention).

As used herein "substantially limited resistance to ticks" and like phrases mean that an animal has a limited or substantially no ability to resist tick attack or infestation. In one embodiment, in the presence of ticks, the animal will carry a higher number of ticks on its coat and/or a higher number of ticks which survive to maturity compared to an animal that has a biological marker in accordance with the invention (including reference to the same animal if it had a biological marker in accordance with the invention)..

As used herein the "worth" of an animal refers to an index used to evaluate the value of an animal, for breeding purposes, inclusion in a herd, herd management, for example. The "worth" is the sum of the estimated value of one or more characteristics which may be associated with the animal, typically weighted by an economic value. Exemplary characteristics include milk fat, protein, milk volume, liveweight, fertility, and milk somatic cells, growth rate, feed conversion efficiency, and egg production. The term "worth" should be taken to encompass "breeding worth" and other known indexes used to assess the value of an animal. Persons skilled in the art to which the invention relates will readily appreciate methods and formulae suitable for estimating breeding worth on the basis of any number of different characteristics. Results, data and/or information generated by a method of the invention may be used in calculations for estimating "worth".

It should be appreciated that where methods of the invention relate to breeding animals, any appropriate breeding methods may be utilised including for example natural insemination, artificial insemination and in vitro fertilisation (IVF). Accordingly, the word "mating" should be construed broadly and not limited to the physical pairing of two animals. It should be appreciated that methods of breeding animals may involve one or more gene editing steps and/or cloning techniques.

As noted herein previously herein, the methods of the invention may be used to identify animals suitable for cloning. They may also be used during cloning processes, to determine whether or not one or more cell, embryo or cloned animal has a genetic variation in the PRLR gene and is likely to have (or develop into an animal having) an increased tolerance to heat, an increased resistance to ticks, and/or desirable coat texture. Any appropriate cloning method could be used. However, by way of example, such cloning techniques include somatic cell nuclear transfer, chromatin transfer, and embryo splitting. Persons of general skill in the art will readily appreciate appropriate somatic cell nuclear transfer and chromatin transfer methodologies. However, by way of example, the methods described in the following publications may be used: Bovine somatic cell nuclear transfer, Ross P J and Cibelli, J B 2010. Methods in Molecular Biology 636: 155-177; and, Influence of cloning by chromatin transfer on placental gene expression at Day 45 of pregnancy in cattle. Mesquita F S, Machado S A, Drnevich J, Borowicz P, Wang Z, Nowak R A. Anim Reprod Sci. 2013 Jan. 30; 136(4):231-44. doi: 10.1016/j.anireprosci.2012.10.030. Epub 2012 Nov. 8.

Where IVF is employed in the context of the invention, any appropriate IVF methodology may be used, as will be apparent to persons of general skill in the art to which the invention relates. However, by way of example, appropriate methods are described, for example, in: Imai K, Tagawa M, Yoshioka H, Matoba S, Narita M, et al. (2006) The efficiency of embryo production by ovum pick-up and in vitro fertilization in cattle. J Reprod Dev 52: 19-29.

Methods of the invention may be described herein with reference to a "standard". The standard may comprise any appropriate sample or other information sufficient to compare the results from a sample from an animal against. In one embodiment the standard may be a control sample comprising PRLR (including reference to one or more isoform, precursor and/or fragment thereof) and/or nucleic acid encoding same from an animal with a known phenotype, which is tested concurrently with a sample from an animal to be tested. However, in another embodiment, the standard could be a printed chart or electronic information or the like containing previously generated data considered to provide an appropriate standard and which the test samples could be compared to on the basis of colour, fluorescence levels, or numerical values, for example. Examples of appropriate standards will be elucidated further herein after. However, in one embodiment the standard will be representative of an animal that has a substantially limited tolerance to heat, an increased resistance to ticks, and/or an undesirable coat texture. In another embodiment, the standard will be representative of an animal that has an increased tolerance to heat, an increased resistance to ticks, and/or a desirable coat texture. In certain embodiments, both of these standards may be used.

Methods of the invention may involve taking a "sample" from an animal to be tested. The sample may be any appropriate tissue or body fluid sample. In one embodiment, the sample may comprise one or more cell, blood, muscle, bone, somatic cell(s), saliva, skin, liver, brain, placenta, amniotic fluid and/or semen. A "sample" can be taken from an animal using standard techniques known in the art. It should be appreciated that a sample may be taken from an animal at any stage of life, including prior to birth; by way of non-limiting example, a zygote, an embryo, a foetus.

Individual gametes could also be tested using the methods of the invention. This may assist in breeding and/or cloning programmes. Accordingly, "sample" should be taken to include a zygote, embryonic tissue, foetal tissue and gametes. A sample may also be taken after the death of an animal.

In addition, it should be appreciated that where analysis or observation of a nucleic acid or peptide of an animal is conducted during gestation, the analysis or observation could be conducted by analysing protein, peptide, nucleic acid or one or more cell of that animal that may be present in the maternal blood supply, placenta, amniotic fluid or any other maternal tissue or fluid prior to birth of the animal. Accordingly, reference to analysing a nucleic acid from an animal, analysing PRLR, a precursor, an isoform and/or fragment thereof from an animal, observing the level of one or more PRLR, a precursor, an isoform and/or fragment thereof in an animal, and/or observing the level of activity of a PRLR, a precursor, an isoform and/or fragment thereof in an animal, and the like, should be taken to include reference to analysing and/or observing one or more of these from that animal that may be present in a maternal tissue or fluid.

"Embryo" should be taken broadly to include an organism from the first division of the zygote. In certain embodiments, an embryo is an organism between the first division of the zygote until the time it becomes a foetus. Reference to an "embryo" should be taken to include reference to an organism at different developmental stages, including a blastula, blastocyst, gastrula, and morula for example.

In one aspect, the invention provides methods for the selection or rejection of one or more cells. In certain embodiments, such "cells" may include a gamete (for example, sperm or ovum) or zygote. Selection of such cells may be of use in an IVF program, for example. In other embodiments, such "cells" may be somatic cells, embryonic cells, embryonic stem cells, cells in a cell line, one or more cells of use in cloning, for example. Selection of these cells may be of use in cloning procedures, or preparing cell lines for use in cloning and other procedures, for example.

Certain aspects and embodiments of the invention may be described herein with reference to "fusing a first and second gamete" to form a zygote. This phrase should be taken broadly to include fertilisation processes, such as may be used in in vitro fertilisation processes. Skilled persons will readily appreciate standard means of "fusing" gametes to form a zygote.

For ease of reference, the methods of the invention may be described herein after in terms of analysing a biological marker (such as a nucleic acid sequence, amino acid sequence, level of a protein and peptide or activity level of a protein or peptide) in or from an "animal" or to determine whether or not an "animal" has a particular marker linked to or associated with an increased tolerance to heat, an increased resistance to ticks, and/or a desirable coat texture or determining the genotype of an "animal", and the like. It should be appreciated that the methods of the invention are also applicable to analysing and determining whether or not individual cells, including gametes, and embryos may have relevant biological markers. Accordingly, reference to "animals" should also be taken to include reference to one or more cell or embryo, unless the context requires otherwise.

The invention may be described herein with reference to an amino acid or nucleic acid sequence, or a level or level of activity of PRLR (including reference to one or more isoform, precursor or fragment thereof) and/or one or more nucleic acid encoding same being "indicative" of an animal (or animals) who has or is more likely than not to have an increased tolerance to heat, an increased resistance to ticks, and/or a desirable coat texture. "Indicative" should not be taken to mean that the level is exactly the same as a level associated with such animal or animals. However, in one embodiment the level or level of activity is substantially similar to or substantially the same as that associated with such animal or animals. One can readily identify whether or not an amino acid or nucleic acid sequence, or a level or level of activity of PRLR (including reference to one or more isoform, precursor or fragment thereof) and/or one or more nucleic acid encoding same is "indicative" of an animal (or animals) who has or is more likely than not to have an increased tolerance to heat, an increased resistance to ticks, and/or a desirable coat texture using the various methods as described herein; for example, comparing the results from a test sample against one or more standard or reference. Reference to "animal or animals" should be taken to mean that a particular reference or standard is based on a value from a single animal or pooled or averaged from a group of animals.

Markers

The specific marker identified herein is located in the PRLR gene at a nucleotide position on chromosome 20 of *Bos Taurus*. The sequence and position given for this gene and the specific genetic marker is based on the genomic sequence of chromosome 20 in bovine build UMD3.1 (gi|258513347|ref|AC_000177.1|) in the GenBank database http://www.ncbi.nlm.nih.gov/). The position of the genetic marker should be read in accordance with base position being the start site of the alteration, given that the first nucleotide in the sequence (gi|12258513347|ref|AC_000177.1|) is denoted as position one. Further, sequence information for the PRLR gene and its location on chromosome 20 is provided on NCBI databases: Reference sequence NM_001039726.2 and Gene ID: 281422, for example. The PRLR gene maps to 38,951,611 and 39,146,316 (excluding promoter sequences). Reference herein to the location of a specific genetic alteration within the PRLR gene (see Table 3 below for example) is to be read relative to its position within the long form gene. Similarly, reference herein to the location of a specific amino acid variation within PRLR is to be read relative to its position within the long form PRLR protein of *Bos Taurus*. Exemplary transcript and protein sequence information for *Bos taurus* PRLR are provided in FIGS. 1 and 2 herein.

Reference is made herein to the PRLR transcript variant 2 mRNA provided on NCBI as NM_001039726.2. With reference to this sequence: the start codon begins at position 85 which corresponds to position 39115293 on UMD 3.1; exon 1 as published by NCBI starts at 39115245; the stop codon begins at position 1828 in mRNA sequence which is at position 39136922 in genome build UMD3.1; the base deletion identified by the inventors is at position 1466 and genomic position 39136559. It should be appreciated that there was a previous version of this NCBI sequence (NM_001039726.1)—FIG. 5, SEQ ID No. 8. With reference to this sequence: the start codon begins at position 87 which corresponds to position 39115293 on UMD 3.1; exon 1 as published by NCBI starts at 39115245; the stop codon begins at position 1830 in mRNA sequence which is at position 39136922 in genome build UMD3.1; the base deletion identified by the inventors is at position 1468 in the mRNA sequence which corresponds to genomic position 39136559.

It will be appreciated that the precise location of the genetic marker of the invention may vary slightly from genome to genome; for example, in a different species of animal, or different breed of animal, the location of the marker may vary. Likewise, the precise location of any amino acid variation in a PRLR protein may vary slightly from proteome to proteome; for example, in different species of animal, or different breeds of animal, the location of an alteration may vary. However, persons of skill in the art to which the invention relate will be able to readily identify a particular marker in different genomes and/or PRLR proteins (including isoforms, fragments and precursors thereof) through routine sequence alignment and with knowledge that it resides in the PRLR gene/PRLR protein ((including isoforms, fragments and precursors thereof). To account for this variation in the location of any particular genetic marker across genomes the marker is described herein as being "at a position corresponding to X position of chromosome 20 of *Bos Taurus*", X being the nucleotide or base pair number read against the chromosome 20 sequence in the UMD3.1 genome build. Similarly, to account for any variation in the location of a particular amino acid variation across proteomes the amino acid variation may be described herein as being "at a position corresponding to Y position of PRLR (or the long-form of PRLR) in *Bos Taurus*", Y being the amino acid number read relative to the *Bos Taurus* PRLR sequence provided in FIG. 2 herein after.

Exemplary PRLR nucleic acid and amino acid sequence information for animals other than *Bos Taurus* can be found on NCBI databases. However, the following database accession numbers are given by way of example:
Pig (*Sus Scrofa* (581)), NC_010458.3 (full nucleotide sequence) and NM_001001868.1 (protein sequence);
chicken (*Gallus Gallus*), NC_006127.3 (full nucleotide sequence) and NP_990185.1 (protein sequence);
sheep (*Ovis aries*), NC_019473.1 (full nucleotide sequence), 046561.1 (protein sequence); and, goat (*Capra Hircus*), JF966783.1 (full nucleotide sequence), AEJ76924.1 (protein sequence).

TABLE 3

Specific genetic marker identified

| Marker Name | Location (Region of gene) | Position (Chromosome 20 Bos Taurus) | Alteration |
|---|---|---|---|
| 39136559del(C) | Last exon | 39136559 | delC, resulting in frame shift |

While the inventors have observed that the alteration identified in table 3 is indicative of an animal being more likely than not to have increased tolerance to heat, an increased resistance to ticks, and/or a desirable coat texture, they contemplate that any variation in nucleotide sequence at this genetic locus may be indicative of an increased tolerance to heat, an increased resistance to ticks, and/or a desirable coat texture. Further, the inventors contemplate that any variation in the nucleotide sequence of the PRLR gene which results in an increase in activity of PRLR may be indicative of an increased tolerance to heat, an increased resistance to ticks, and/or a desirable coat texture. The invention should be interpreted accordingly. Such variations may include for example, the addition of one or more nucleotide, the deletion of one or more nucleotide, the substitution of one or more nucleotide or combinations of two or more thereof.

In one embodiment, one or more alteration is located within a region bounded by nucleotides corresponding to positions 39136469 and 39136649 of chromosome 20 of *Bos Taurus*. In other embodiments, one or more alteration is located within a region bounded by nucleotides corresponding to positions 39136498 and 39136620, to positions 39136528 and 39136590, or to positions 39136543 and 39136575. In one embodiment, the one or more genetic alteration is located in the final exon of the PRLR gene; for example, a region bounded by nucleotides corresponding to positions 39136033 to 39136920 of chromosome 20 of *Bos Taurus*.

In one embodiment, one or more alteration results in an alanine to valine substitution at a position corresponding to position 461 of PRLR of *Bos Taurus*. In one embodiment, one or more genetic alteration results in truncation of the transcript or peptide expressed from the PRLR gene. In certain embodiment, one or more alternation results in a truncation of PRLR to an amino acid position which is in a region from approximately an amino acid position corresponding to position 430 to an amino acid position corresponding to position 490 of PRLR of *Bos Taurus*, a truncation of PRLR to an amino acid position which is in a region from approximately an amino acid position corresponding to position 440 to amino acid position 480 of PRLR of *Bos Taurus*, a truncation of PRLR to an amino acid position which is in a region from approximately an amino acid position corresponding to position 450 to amino acid position 470 of PRLR of *Bos Taurus*, or a truncation of PRLR to an amino acid position which is in a region from approximately an amino acid position corresponding to position 455 to amino acid position 465 of PRLR of *Bos Taurus*. In one embodiment, one or more alternation results in truncation of PRLR to a position corresponding to amino acid position 461 of PRLR of *Bos Taurus*. In one embodiment, one or more alternation results in substitution of an alanine with a valine at position 461 and truncation of PRLR to a position corresponding to amino acid position 461 of PRLR of *Bos Taurus*.

Similarly, while the inventors have observed that the amino acid variation in PRLR described herein is indicative of an animal being more likely than not to have increased tolerance to heat, an increased resistance to ticks, and/or a desirable coat texture, they contemplate that any variation amino acid sequence at the same position may be indicative of an increased tolerance to heat, an increased resistance to ticks, and/or a desirable coat texture. Further, the inventors contemplate that any variation in the amino acid sequence of a PRLR which results in an increase in activity of PRLR may be indicative of an increased tolerance to heat, an increased resistance to ticks, and/or a desirable coat texture. The invention should be interpreted accordingly. Such variations may include for example, the addition of one or more amino acid, the deletion of one or more amino acid, the substitution of one or more amino acid or combinations of two or more thereof.

In certain embodiments of the invention, one or more amino acid variation is located in a region corresponding to amino acid position 430 to amino acid position 490 of PRLR of *Bos Taurus*, in a region corresponding to amino acid position 440 to amino acid position 480 of PRLR of *Bos Taurus*, in a region corresponding to amino acid position 450 to amino acid position 470 of PRLR of *Bos Taurus* or in a region corresponding to amino acid position 455 to amino acid position 465 of PRLR of *Bos* Taurus.

In one embodiment, one or more amino acid variation is an alanine to valine substitution at a position corresponding to position 461 of PRLR of *Bos Taurus*. In one particular embodiment, one or more variation in the amino acid sequence is a deletion resulting in truncation of PRLR. In one embodiment, one or more variation results in a truncation of PRLR to an amino acid position which is in a region from approximately an amino acid position corresponding to position 430 to an amino acid position corresponding to position 490 of PRLR or Bos Taurus, a truncation of PRLR to an amino acid position which is in a region from approximately an amino acid position corresponding to position 440 to amino acid position 480 of PRLR of Bos Taurus, a truncation of PRLR to an amino acid position which is in a region from approximately an amino acid position corresponding to position 450 to amino acid position 470 of PRLR of Bos Taurus, or a truncation of PRLR to an amino acid position which is in a region from approximately an amino acid position corresponding to position 455 to amino acid position 465 of PRLR of Bos Taurus. In one embodiment, one or more alternation results in a truncation of PRLR to a position corresponding to amino acid position 461 of PRLR of Bos Taurus. In one embodiment, one or more amino acid variation is a substitution of an alanine with a valine at position 461 and truncation of PRLR to a position corresponding to amino acid position 461 of PRLR of Bos Taurus.

The inventors note that the specific alteration referred to in table 3 is dominant in nature. They believe this will be the case for other alterations in the PRLR gene. Accordingly, for example, where an animal is heterozygous for an alteration it will be inferred that it is more likely than not to have an increased tolerance to heat, an increased resistance to ticks, and/or a desirable coat texture. In light of this, the methods of the invention do not require a determination of the homo- or heterozygosity of an animal. However, in certain embodiments, it may be desirable to determine whether the animal is homozygous. For example, in the case of selecting animals for breeding purposes or for inclusion in a herd, knowing whether the animal is homozygous may be of benefit as it will help ensure that any offspring carry the desired genetic alteration.

Alteration in Nucleic Acid Sequence

In certain embodiments, the methods of the invention involve the analysis of a nucleic acid (including one or more nucleic acid) from an animal to determine the presence or absence of one or more genetic alteration in the PRLR gene. Such one or more genetic alterations will be indicative of an animal and/or animals that has/have or is more likely than not to have an increased tolerance to heat, an increased resistance to ticks, and/or a desirable coat texture. In one embodiment, the one or more genetic alterations result in an increase in the activity of PRLR.

It should be appreciated that one or more genetic alteration may be identified by observing the size of the PRLR gene or a part or region thereof.

In one embodiment, one or more alteration is located within a region bounded by nucleotides corresponding to positions 39136469 and 39136649 of chromosome 20 of Bos Taurus. In other embodiments, one or more alteration is located within a region bounded by nucleotides corresponding to positions 39136498 and 39136620, to positions 39136528 and 39136590, or to positions 39136543 and 39136575. In one embodiment, the one or more genetic alteration is located in the final exon of the PRLR gene; for example, a region bounded by nucleotides corresponding to positions 39136033 to 39136920 of chromosome 20 of Bos Taurus.

In one embodiment, for example, the methods involve the analysis of a nucleic acid (including one or more nucleic acid) to determine the nucleotide present at a position corresponding to position 39136559 of chromosome 20 of Bos taurus.

Alternatively, or in addition, the methods may involve analysising the nucleotide sequence of a nucleic acid to determine the nucleotide sequence of one or more genetic marker in linkage disequilibrium with a genetic alteration in the PRLR gene, for example a genetic marker (genetic variation) at the above mentioned position.

In one particular embodiment, the methods of the invention may involve analysing the nucleotide sequence of a nucleic acid to determine the haplotype of an animal, one or more cells or an embryo, for example, wherein the haplotype includes the genetic marker (genetic variation in the PRLR gene) mentioned above in combination with one or more genetic markers in linkage disequilibirum therewith.

It should also be appreciated that one could analyse the nucleic acid sequence of either strand of the nucleic acid to identify the sequence at a particular genetic locus or position; for example, instead of analysing the strand associated with the sequence variant listed above, the nucleotide sequence of the opposite or complementary strand of DNA could be analysed. Persons of skill in the art will readily appreciate nucleic acid sequence variations on such opposite strand which correlate with the genotypes mentioned above, having regard to the information contained herein and nucleic acid base pairing principles (ie, A pairs with T and C pairs with G).

Nucleic acids can be analysed to determine the genotype/sequence of a genetic marker according to any appropriate technique. Such techniques include for example polymerase chain reaction (PCR), including allele-specific PCR, gel electrophoresis, the use of oligonucleotide probe hybridisation, Southern blotting, direct sequencing, restriction digestion, restriction fragment length polymorphism (RFLP), single-strand confirmation polymorphism (SSCP), LCR (ligase chain reaction), denaturing gradient gel electrophoresis (DGGE), the use of allele-specific oligonucleotides (ASOs), the use of proteins which recognize nucleic acid mismatches, such as E. coli mutS protein, RNAse protection assays, oligonucleotide array hybridisation (for example microarray), denaturing HPLC (dHPLC), fluorescence quenching PCR (TaqMan™, Applied Biosystems, CA 94404, USA), High Resolution Melting (HRM), matrix-assisted laser desorption/ionisation time-of-flight mass spectroscopy (MALDI-TOF MS), and qRT-PCR. Combinations of two or more of such techniques may be used. Such combination may increase the sensitivity of the analysis being conducted.

In certain embodiments, analysis can be conducted on a single cell. In such cases, genome amplification and/or next generation sequencing methodology may be used. Skilled persons will readily appreciate appropriate methodology. However, by way of example, the methodology described in Navin et al (Nature, 2011 Apr. 7; 472(7341):90-4. doi: 10.1038/nature09807. Epub 2011 Mar. 13. Tumour evolution inferred by single-cell sequencing) could be used.

The technique(s) used will depend on the nature of the marker to be detected as will be appreciated by skilled persons. For example, single nucleotide polymorphisms (SNPs), may be analysed using those techniques capable of resolving a single nucleotide difference between sequences; for example, direct sequencing or LCR, allele-specific PCR, RFLP, SSCP, DGGE, using allele-specific oligonucleotides (ASOs), or proteins which recognize nucleic acid mismatches, oligonucleotide array hybridisation, dHPLC, fluorescence quenching PCR, and matrix MALDI-TOF MS.

Any one or more of the techniques mentioned hereinbefore (including for example, SSCP, RFLP, DGGE, dHPLC and direct sequencing) may be used to analyse genetic markers which may include insertion or deletion of one or more nucleotide.

It should be appreciated that certain of the techniques of use in analysing a genetic marker in accordance with the invention will utilise one or more oligonucleotides which hybridise to a genetic region encompassing the marker, adjacent to the marker, or flanking the marker. Such oligonucleotides may be DNA, RNA or derivatised forms thereof and include nucleic acid primers, such as PCR and LCR primers, and nucleic acid probes.

Persons of ordinary skill in the art to which the invention relates will readily appreciate appropriate oligonucleotides of use in the invention having regard to one or more of the nucleic acid sequence of the PRLR gene, chromosome 20, particularly in the genetic regions proximal to a genetic marker, the nature of the genetic marker to be analysed, and the general principles of nucleic acid hybridisation. The nucleic acids will be capable of hybridising in a specific manner to a target nucleic acid and in the case of primers they will be capable of priming a PCR or like reaction. While such nucleic acids will preferably have 100% complementarity to their target region of the mRNA or cDNA of the protein of interest, they may contain one or more non-complementary nucleotides at a particular position while still substantially retaining specificity for the target nucleic acid to which they are designed to bind. By way of example, the nucleic acids may have approximately 80%, approximately 90%, approximately 95%, or approximately 99% complementarity or homology to its target. By way of further example, in certain cases, the oligonucleotides may be designed such that a mismatch at a particular nucleotide position is indicative of the nature of the genetic marker being analysed (for example, a SNP). By way of example, a mismatch in the nucleotide present at the 3' end of an LCR primer will inhibit the reaction providing an indication of the nature of the nucleotide at that position. Mismatches may similarly be utilised in techniques including RNAse protection assays and allele-specific PCR, as well as in fluorescence quenching PCR, for example. Typically, the nucleic acids will hybridise to their target nucleic acid under stringent hybridisation conditions (see for example, Sambrook and Russell, Molecular Cloning: A Laboratory Manual, 2001, Cold Spring Harbor Laboratory Press, Cold Spring Harbor, New York).

The oligonucleotide probes or primers may be of any length as is appropriate for a particular application, having regard to the sequence of the genetic region to which they are designed to bind. A probe or primer will typically be capable of forming a stable hybrid with the complementary sequence to which it is designed to hybridise. Accordingly, the length is dependent on the nucleic acid composition and percent homology between the oligonucleotide and its complementary sequence, as well as the hybridisation conditions which are utilised (for example, temperature and salt concentrations). Such hybridisation factors are well known in the art to which the invention relates. By way of example, oligonucleotides of use in the present invention may be from 2 to 500 nucleotides in length. In one embodiment, particularly where they are used as primers, the oligonucleotides may be of approximately 15 nucleotides to 30 nucleotides in length.

Non-limiting examples of oligonucleotides of use in the invention include CCTATTTTCTGGCCAATGGA (SEQ ID No. 1), CAGCCCAACTGGAGTCTGC (SEQ ID No. 2) and/or functionally equivalent variants of one or more thereof. In one embodiment, these oligonucleotides are used as forward and reverse primers in a method of the invention which utilizes PCR.

In one particular embodiment, the oligonucleotides CCTATTTTCTGGCCAATGGA (SEQ ID No. 1) and CAGCCCAACTGGAGTCTGC (SEQ ID No. 2) and/or functionally equivalent variants of one or more thereof are used as forward and reverse primers for detection of a genetic alteration at position 39136559 of chromosome 20 of Bos taurus in accordance with a method of the invention.

Oligonucleotide probes and primers of use in the invention may be prepared by any number of conventional DNA synthesis methods including recombinant techniques and chemical synthesis, or they may be purchase commercially. It will be appreciated that the usefulness of any probe or primer may be evaluated, at least notionally, using appropriate software and sequence information for the nucleic acid encoding the protein of interest. For example, software packages such as Primer3 (http://primer3.sourceforge.net/), PC Oligo5 (National Bioscience Inc), Amplify (University of Wisconsin), and the PrimerSelect program (DNAStar Inc) may be used to design and evaluate primers.

Where amplification techniques (for example PCR) are used in methods of the invention amplification may be conducted according to conventional procedures in the art to which this invention relates, such as described in U.S. Pat. No. 4,683,202. By way of example PCR reactions will generally include 0.1 µM-1 µM of each primer, 200 µM each dNTP, 3-7 mM $MgCl_2$, and 1U Taq DNA polymerase. Further, exemplary PCR cycling conditions include: denaturation at a temperature of approximately 94° C. for 30 to 60 seconds, annealing at a temperature calculated on the basis of the sequence and length of the primer (as herein after discussed) for 30 to 60 seconds, and extension at a temperature of approximately 70° C. to 72° C. for 30 to 60 seconds. By way of example, between 25 and 45 cycles are run.

It will be appreciated by those of ordinary skill in the art that any amplification conditions provided herein are merely exemplary and may be varied so as to optimise conditions where, for example, alternative PCR cyclers or DNA polymerases are used, where the quality of the template DNA differs, or where variations of the primers not specifically exemplified herein are used, without departing from the scope of the present invention. The PCR conditions may be altered or optimised by changing the concentration of the various constituents within the reaction and/or changing the constituents of the reaction, altering the number of amplification cycles, the denaturation, annealing or extension times or temperatures, or the quantity of template DNA, for example. Those of skill in the art will appreciate there are a number of other ways in which PCR conditions may be optimised to overcome variability between reactions.

It will be understood that whilst not specifically exemplified herein, appropriate annealing temperatures for any primer within the scope of the present invention may be derived from the calculated melting temperature of that primer. Such melting temperatures may be calculated using standard formulas, such as that described in Sambrook and Russell, 2001. As will be understood by those of ordinary skill in the art to which this invention relates annealing temperatures may be above or below the melting temperature but generally an annealing temperature of approximately 5° C. below the calculated melting temperature of the primer is suitable.

Oligonucleotides used for detection and/or analysis of genetic markers in accordance with the invention may be modified to facilitate such detection. Similarly, nucleic acid products obtained using techniques such as PCR may be modified to facilitate detection and/or analysis. For example, the nucleic acid molecules may be labelled to facilitate visual identification using techniques standard in the art. By way of example nucleic acids may be radio-labelled using $P^{32}$ as may be described in Sambrook and Russell, 2001. Further, nucleic acids may be appropriately labelled for use in colorigenic, fluorogenic or chemiluminescence procedures.

It will be appreciated that the methods of the invention may employ one or more control samples. Such control samples may be positive or negative controls for a particular genetic marker. The type of control samples used may vary depending on such factors as the nature of the genetic marker being analysed and the specific technique being used for such detection and analysis. Positive controls may include samples having known nucleic acid sequences or being of a known size, for example. Negative controls may include samples having no nucleic acid present. By way of general example, in analysing a SNP positive control samples could include nucleic acids known to have a particular nucleotide at the relevant position. In one embodiment, the method may utilise a control sample having a sequence which is not associated with increased tolerance to heat, an increased resistance to ticks, and/or a desirable coat texture or is associated with substantially limited tolerance to heat, a substantially limited resistance to ticks, and/or an undesirable coat texture. In another embodiment, the method may utilise a control sample having a sequence which is associated with increased tolerance to heat, an increased resistance to ticks, and/or a desirable coat texture.

The methods of this embodiment of the invention may involve comparing the sequence of a nucleic acid being tested to one or more reference sequences, as herein before described.

The methods of the invention may involve taking a sample (as herein before described) from an animal to be tested. In this embodiment of the invention, the samples are analysed using techniques which allow for the observation or analysis of nucleic acids, including the sequence of a particular nucleic acid.

In order to facilitate detection of a genetic marker in accordance with the invention, a sample may be processed prior to analysis. For example, the sample may be processed to isolate nucleic acid from the sample to be analysed or to amplify a specific genetic region to be analysed.

In one embodiment, nucleic acid is isolated or extracted from the sample prior to analysis. In one embodiment, genomic DNA is isolated or extracted from the sample. In an alternative embodiment, mRNA may be isolated or extracted from the sample. In such a case, the mRNA may be converted to cDNA using reverse transcription techniques known in the art. Techniques for isolating nucleic acids from samples will be readily appreciated by skilled persons. By way of Example, methods of use in isolating nucleic acids are described in Sambrook and Russell, 2001.

In an alternative form of this embodiment of the invention analysis of the nucleic acid may occur in situ obviating the need to extract nucleic acid from the sample. This may be done using PCR for example. Skilled persons will readily appreciate appropriate techniques and methodology to this end (see for example, Sambrook and Russell, 2001).

The methods of the invention may be combined with one or more other methods of use in assessing genotype, predicting phenotype, selecting an animal, cell or embryo based on certain characteristics, estimating breeding values or estimating worth and the like. Accordingly, the methods of the invention may include, in addition to analysis of a genetic marker identified herein, analysis of additional genetic markers, and/or the level of expression of certain genes/proteins, and/or one or more phenotypic traits, for example.

Nucleic Acids

The invention also provides nucleic acids carrying genetic markers of the invention. For example, isolated nucleic acids encompassing a region of a PRLR gene in which a genetic marker as herein before described resides are encompassed by the invention.

The invention also encompasses nucleic acids which can hydridise, preferably under stringent conditions (as herein before described), to a region of a PRLR gene in which one or more of genetic marker of the invention resides. Such nucleic acids may be used as primers or otherwise in analysis of genetic markers of the invention, as herein before described.

Nucleic acids of the invention may have 100% sequence identity, homology or complementarity to the relevant region of a PRLR gene, but may also have some sequence variation. For example, nucleic acids of the invention may have approximately 80%, approximately 90%, approximately 95% or approximately 99% sequence identity, homology or complementarity.

The nucleic acids of the invention may be of any appropriate length. In one embodiment, they are at least 4 nucleotides in length, or at least 10, 20, 30, 40, 50, 60, 70, 80 or more nucleotides in length.

In one embodiment, the invention provides a nucleic acid comprising (or in one embodiment consisting of) the nucleotide sequence GACCAAACAGACCAACATG (C) del TTTAAAAGCCTCAAAAACCA wherein (C)del indicates the absence of a C at that position (ie. GACCAAACAGAC-CAACATGTTTAAAAGCCTCAAAAACCA—SEQ ID No. 3).

In other embodiments, a nucleic acid of the invention comprises (or in one embodiment consisting of) the nucleotide sequence CCTATTTTCTGGCCAATGGA (SEQ ID No. 1), CAGCCCAACTGGAGTCTGC (SEQ ID No. 2), or a nucleotide sequence which is a functionally equivalent variant of any one or more thereof. Such nucleic acids may be used as primers in a method of the invention which involves the use of PCR.

In other embodiments, the invention provides one or more cDNA comprising a genetic alteration as described herein or encoding a PRLR, isoform, fragment or precursor thereof, including those comprising one or more variation in the amino acid sequence.

Variation in Amino Acid Sequence

In other embodiments, the methods of the invention comprise analysing one or more of PRLR, one or more precursor thereof, one or more isoform thereof, and/or one or more fragment thereof from said animal to determine whether or not it includes one or more variation in the amino acid sequence. Such one or more variation in the amino acid sequence will be indicative of an animal and/or animals that has/have or is more likely than not to have an increased tolerance to heat, an increased resistance to ticks, and/or a desirable coat texture. In one embodiment, the one or more variation results in an increase in the activity of PRLR. The variation in the amino acid sequence may be the addition of one or more amino acid, the deletion of one or more amino acid, the substitution of one or more amino acid or a combination of two or more thereof. In one particular embodiment, the variation in the amino acid sequence is a deletion of one or more amino acid. In one embodiment, the one or more variation is an amino acid substitution. In one embodiment, the amino acid sequence of PRLR is truncated. In certain embodiments, the one or more variation in the amino acid sequence is as herein before described.

It should be appreciated that one or more variation in the amino acid sequence may be identified by observing the size of PRLR, one or more precursor thereof, one or more isoform thereof and/or one or more fragment thereof.

In certain embodiments of the invention, the one or more amino acid variation is located in a region corresponding to amino acid position 430 to amino acid position 490 of PRLR of Bos Taurus, in a region corresponding to amino acid position 440 to amino acid position 480 of PRLR of Bos Taurus, in a region corresponding to amino acid position 450 to amino acid position 470 of PRLR of Bos Taurus or in a region corresponding to amino acid position 455 to amino acid position 465 of PRLR of Bos Taurus.

In one embodiment, one or more amino acid variation is an alanine to valine substitution at a position corresponding to position 461 of PRLR of Bos Taurus. In one particular embodiment, one or more variation in the amino acid sequence is a deletion resulting in truncation of PRLR. In one embodiment, one or more variation results in a truncation of PRLR to an amino acid position which is in a region from approximately an amino acid position corresponding to position 430 to an amino acid position corresponding to position 490 of PRLR or Bos Taurus, a truncation of PRLR to an amino acid position which is in a region from approximately an amino acid position corresponding to position 440 to amino acid position 480 of PRLR of Bos Taurus, a truncation of PRLR to an amino acid position which is in a region from approximately an amino acid position corresponding to position 450 to amino acid position 470 of PRLR of Bos Taurus, or a truncation of PRLR to an amino acid position which is in a region from approximately an amino acid position corresponding to position 455 to amino acid position 465 of PRLR of Bos Taurus. In one embodiment, one or more alternation results in a truncation of PRLR to a position corresponding to amino acid position 461 of PRLR of Bos Taurus. In one embodiment, one or more amino acid variation is a substitution of an alanine with a valine at position 461 and truncation of PRLR to a position corresponding to amino acid position 461 of PRLR of Bos Taurus. In one embodiment, a method of the invention could comprise testing for the presence or absence of a C-terminal valine, for example.

To the extent that a biological marker in accordance with the invention may include addition and/or deletion of one or more amino acid, the size of a protein (including reference to one or more precursor thereof, one or more isoform thereof, and/or one or more fragment thereof) methods of the invention may involve observation or measurement of the size of a protein, one or more precursor thereof, one or more isoform thereof, and/or one or more fragment thereof. In one particular embodiment, the presence of a PRLR which is 430 amino acids in length or shorter, 430 to 490 amino acids in length, 440 to 480 amino acids in length, 450 to 470 amino acids in length, 455 to 465 amino acids in length, infers that an animal, cell or embryo carries a biological marker linked to an increased tolerance to heat, an increased resistance to ticks and/or a desirable coat texture. In one particular embodiment, the presence of a PRLR which is 461 amino acids in length or smaller infers that an animal, cell or embryo carries a biological marker linked to an increased tolerance to heat, an increased resistance to ticks and/or a desirable coat texture.

PRLR, isoforms thereof, precursors thereof, and/or fragments thereof may be analysed using standard techniques known in the art. However, by way of example, peptide sequencing methods, mass spectrometry, Western blotting and ELISA could be used.

The methods may employ one or more control samples, such as positive and/or negative controls for a particular amino acid sequence variation. The type of control samples used may vary depending on such factors as the type of variation being analysed and the specific technique being used for detection and analysis. Positive controls may include samples having known amino acid sequences or being of a known size, for example. Negative controls may include samples having no peptide present. In one embodiment, the method may utilise a control sample having a sequence which is not associated with increased tolerance to heat, an increased resistance to ticks, and/or a desirable coat texture or is associated with substantially limited tolerance to heat, substantially limited resistance to ticks, and/or an undesirable coat texture. In another embodiment, the method may utilise a control sample having a sequence which is associated with increased tolerance to heat, an increased resistance to ticks, and/or a desirable coat texture.

The methods of this embodiment of the invention may involve comparing the sequence of a peptide or protein being tested to one or more reference sequences, as herein before described.

The methods of the invention may involve taking a sample for an animal to be tested. In order to facilitate analysis of a peptide in accordance with the invention, a sample may be processed prior to analysis according to any of a number of known methods. For example, the sample may be processed to remove one or more one or more high abundance proteins that might make it difficult to analyse PRLR, an isoform, fragment or precursor thereof. Exemplary techniques which may be employed to process a sample prior to analysis of PRLR, an isoform, fragment or precursor thereof are described elsewhere herein.

Proteins or Peptides

The invention also provides peptides and proteins carrying biological markers of the invention. For example, isolated peptides or proteins encompassing a region of PRLR in which a biological marker as herein before described resides are encompassed by the invention.

The peptides or proteins of the invention may be of any appropriate length. In one embodiment, they are at least 4 amino acids in length, or at least 10, 20, 30, 40, 50, 60, 70, 80 or more amino acids in length.

In one embodiment, the invention provides a peptide consisting or comprising (or in one embodiment consisting of) the amino acid sequence of SEQ ID No. 7.

Level of PRLR, Precursors, Fragments, and/or Isoforms

In another embodiment, the methods of the invention involve observing the level of one or more of PRLR (including reference to any one or more isoform of PRLR, any one or more precursor of PRLR, any one or more fragment of PRLR), and/or any one or more nucleic acid encoding one or more of the foregoing.

As mentioned herein before, the inventors contemplate that an increase in the level (for example, an increase in the level of expression) of PRLR (including reference to one or more isoform, precursor or fragment thereof) and/or a nucleic acid encoding same infers an animal will more likely than not have an increased tolerance to heat, an increased resistance to ticks, and/or a desirable coat texture. Therefore, the inventors contemplate that any increase in the level may be considered to infer an increased tolerance to heat (and/or an increased resistance to ticks and/or a desirable coat texture) in the animal and/or its offspring. Similarly, a decrease or substantially no increase in the level (for example, the level of expression) compared to a standard may also infer a decreased or substantially no increase in tolerance to heat, increase in resistance to ticks, and/or an undesirable coat texture for the animal and/or its offspring.

In certain embodiments of the invention the methods may taking a sample from an animal, observing the level (in one embodiment the level of expression) of PRLR (including reference to one or more isoform, precursor and/or fragment thereof) or nucleic acids encoding same, and comparing the level against one or more standard. The levels observed in the sample and any difference in the level between the sample and the standard infers whether the animal will more likely than not have an increased tolerance to heat, an increased resistance to ticks, and/or a desirable coat texture.

In one embodiment, the standard represents a level of PRLR (including reference to one or more isoform, precursor and/or fragment thereof) and/or a nucleic acid encoding same, which is associated with a level in an animal or animals which have substantially limited tolerance to heat, substantially limited resistance to ticks, and/or an undesirable coat texture. In another embodiment, the standard represents a level of PRLR (including reference to one or more isoform, precursor and/or fragment thereof) and/or a nucleic acid encoding same which is associated with a level in an animal (or animals) which has an increased tolerance to heat, an increased resistance to ticks, and/or a desirable coat texture.

In one embodiment, a higher level of PRLR (including reference to one or more isoform, precursor and/or fragment thereof) or a nucleic acid encoding same compared to a standard (having a level which is associated with an animal or animals which have substantially limited tolerance to heat, substantially limited resistance to ticks, and/or an undesirable coat texture, for example) infers that the animal will more likely than not have an increased tolerance to heat, an increased resistance to ticks, and/or a desirable coat texture. In one embodiment, substantially similar to, substantially the same as or a lower level of PRLR (including reference to one or more isoform, precursor or fragment thereof) or a nucleic acid encoding same infers that the animal will more likely than not have a decreased or substantially limited or substantially no increased tolerance to heat, increased resistance to ticks, and/or an undesirable coat texture.

In one embodiment, where the standard represents a level of PRLR (including reference to one or more isoform, precursor and/or fragment thereof) and/or a nucleic acid encoding same which is associated with a level in an animal (or animals) which has an increased tolerance to heat, an increased resistance to ticks, and/or a desirable coat texture and the animal being tested has a level of PRLR (including reference to one or more isoform, precursor and/or fragment thereof) or a nucleic acid encoding same substantially similar to, substantially the same as or higher than the standard, it is inferred that the animal will more likely than not have an increased tolerance to heat, an increased resistance to ticks, and/or a desirable coat texture. Where the animal being tested has a level lower than the standard, it may be inferred that the animal will more likely than not have a decreased or substantially limited or substantially no increased tolerance to heat, substantially no increased resistance to ticks, and/or an undesirable coat texture.

PRLR (including reference to one or more precursors, fragments and/or isoforms thereof) and nucleic acids encoding same may be detected and the levels thereof compared to a standard using any one or a combination of techniques which are of use in identifying, quantifying and/or highlighting differential levels or expression of one or more proteins. Such techniques will be readily appreciated by persons of ordinary skill in the art to which the invention relates. However, by way of example, the levels of PRLR (including reference to one or more precursors, fragments and/or isoforms thereof) may be measured using protein purification methods, immunological techniques, separation of proteins based on characteristics such as molecular weight and isoelectric point including gel electrophoresis (for example, PAGE) and microfluidics-based technologies as for example in gel-free protein separation techniques, and mass spectrometry (MS) utilizing isobaric label based MS such as iTRAQ or label-free approaches such as multiple reaction monitoring (MRM).

Appropriate immunological techniques include enzyme linked immunosorbent assay (ELISA) (sandwich ELISA, double sandwich ELISA, direct ELISA, microparticle ELISA), radioimmunoassay (RIA), immunoprecipitation, Western blotting, immunohistochemical staining, antibody arrays, or agglutination assays. Protocols for carrying out such techniques are readily available; for example, see "Antibodies a Laboratory Manual", Cold Spring Harbor Laboratory Press (1988).

Antibodies of use in such immunological techniques may be purchased commercially or produced according to standard methodology in the art having regard to the nature of the proteins to be tested. For example, polyclonal antibodies and monoclonal antibodies may be produced in accordance with the procedures described in the text "Antibodies a Laboratory Manual" (Cold Spring Harbor Laboratory Press, 1988) using one or more of the proteins or a fragment thereof as antigen. Preferably monoclonal antibodies are used.

Nucleic acid-based techniques of use in determining the level of a nucleic acid (for example cDNA levels) may include differential display procedures, Northern Blotting, competitive PCR, quantitative reverse transcriptase polymerase chain reaction (qRT-PCR), microarray analysis, and RNA sequencing. Persons skilled in the art to which the invention relates will readily appreciate methodology for performing these techniques.

Nucleic acids, such as oligonucleotide probes and primers, of use in detecting expression levels of proteins in accordance with the invention (for example using Northern blotting or competitive PCR) will be readily appreciated by skilled persons having regard to the information contained herein and any published amino acid and/or nucleic acid sequence information for PRLR. The nucleic acids will be capable of hybridising in a specific manner to an mRNA or cDNA associated with PRLR and in the case of primers they will be capable of priming a PCR or like reaction.

Mass spectroscopy techniques of use in the invention are described for example in "Proteins and proteomics-A laboratory manual" (RJ Simpson, Cold Spring Harbour Laboratory Press (2002).

The levels of PRLR (including reference to one or more fragment, precursor and/or isoform) or nucleic acids encoding same in a sample versus a standard may be compared using standard technology having regard to the method employed to detect the protein or nucleic acid. For example, colorimetric and fluorometric techniques may be used in which a detection molecule (such as an antibody or nucleic acid probe or primer) is labelled with a molecule which can be visualised by the naked eye or otherwise detected using a spectrophotometer, or fluorometer for example. Alternatively, detection molecules could be labelled with radioisotopes. Incorporating labels into nucleic acids during PCR amplification where it is employed (as opposed to labelling a detection molecule such as a probe or primer), is also contemplated.

Methods for labelling molecules and subsequently measuring the intensity of signals generated will be known to those of skill in the art to which the invention relates.

It should be appreciated that in addition to analysing samples and standards, the methods of the invention may include the testing of one or more positive or negative control samples to ensure the integrity of the results. For example, one could include a sample containing no protein/nucleic acid and one or more samples containing a known level of protein/nucleic acid so that results can be calibrated across different runs of the method.

A sample taken from an animal may be processed prior to analysing PRLR (including reference to one Or more isoform, precursor and/or fragment) and/or a nucleic acid encoding same to facilitate analysis of the proteins or nucleic acids. Skilled persons will readily appreciate appropriate processing steps and techniques suitable for performing them.

In one embodiment, high abundance proteins which have the potential to make it difficult to analyse, such as detect and/or measure the level of PRLR (including reference to one or more isoform, precursor and/or fragment) may be removed from the sample. For example, Top6 or Top7 depletion may be used. The sample may also be subject to proteolytic digestion. As such detection of a protein or isoform in accordance with the invention should be taken to include detection of any one or more fragments thereof. Fragments should be of a length sufficient to ensure specificity to PRLR. Such fragments will for example be at least 8 amino acids in length, more preferably at least 10, 15 or 20 amino acids in length.

Processing steps for preparing a sample for analysis of nucleic acids encoding PRLR (including reference to one or more isoform, precursor and/or fragment) may include lysing cells, isolating mRNA, and generating cDNA using standard procedures such as reverse transcription-PCR as will be known in the art to which the invention relates. In one embodiment, mRNA may be observed in situ.

Skilled persons may readily appreciate other means by which the sample may be processed for use in the invention.

Activity of PRLR, Precursors, Fragments, and/or Isoforms

In another embodiment, methods of the invention may involve observing the level of activity of PRLR (including reference to one or more precursor, isoform and/or fragment thereof).

As mentioned herein before, the inventors contemplate that an increase in the level of activity of PRLR (including reference to one or more isoform, precursor or fragment thereof) infers the animal will more likely than not have an increased tolerance to heat, an increased resistance to ticks, and/or a desirable coat texture. Therefore, the inventors contemplate that any increase in the level of activity may be considered to infer an increased tolerance to heat, an increased resistance to ticks, and/or a desirable coat texture in the animal and/or its offspring. Similarly, a decrease or substantially no increase in the level of activity compared to a standard may also infer a decreased or substantially no increase in tolerance to heat, increase in resistance to ticks, and/or an undesirable coat texture for the animal and/or its offspring.

In certain embodiments of the invention, the methods may involve taking a sample from an animal, observing the level of activity of PRLR (including reference to one or more isoform, precursor and/or fragment thereof), and comparing the level of activity against one or more standard. The level of activity observed in the sample and any difference between the sample and the standard infers whether the animal will more likely than not have an increased tolerance to heat, an increased resistance to ticks, and/or a desirable coat texture.

In one embodiment, the standard represents a level of activity of PRLR (including reference to one or more isoform, precursor and/or fragment thereof) which is associated with a level in an animal or animals which have substantially limited tolerance to heat, substantially limited resistance to ticks, and/or an undesirable coat texture. In another embodiment, the standard represents a level of activity of PRLR (including reference to one or more isoform, precursor and/or fragment thereof) which is associated with a level in an animal (or animals) which has an increased tolerance to heat, an increased resistance to ticks, and/or a desirable coat texture.

In one embodiment, a higher level of activity of PRLR (including reference to one or more isoform, precursor and/or fragment thereof) compared to a standard (having a level which is associated with an animal or animals which have substantially limited tolerance to heat, substantially limited resistance to ticks, and/or an undesirable coat texture, for example) infers that the animal will more likely than not have an increased tolerance to heat, an increased resistance to ticks, and/or a desirable coat texture. In one embodiment, the substantially similar to, substantially the same as, or a lower level of activity PRLR (including reference to one or more isoform, precursor or fragment thereof) infers that the animal will more likely than not have a decreased or substantially limited or substantially no increased tolerance to heat, substantially no increased resistance to ticks, and/or an undesirable coat texture.

In one embodiment, where the standard represents a level of activity of PRLR (including reference to one or more isoform, precursor and/or fragment thereof) which is associated with a level in an animal (or animals) which has an increased tolerance to heat, an increased resistance to ticks, and/or a desirable coat texture and the animal being tested has a level of activity of PRLR (including reference to one or more isoform, precursor and/or fragment thereof) substantially similar to, substantially the same as, or higher than the standard, it is inferred that the animal will more likely than not have an increased tolerance to heat, an increased resistance to ticks, and/or a desirable coat texture. Where the animal being tested has a level lower than the standard, it may be inferred that the animal will more likely than not have a decreased or substantially limited or substantially no increased tolerance to heat, substantially no increased resistance to ticks, and/or an undesirable coat texture.

The level of activity of PRLR may be measured using standard methodology as known in the art, having regard to the function of PRLR. By way of example, the methods used may involve one or more of the following techniques: Immunoprecipitation, Western blotting, ELISA, mass spectrometry, surface plasmon resonance, isothermal titration calorimetry, luciferase assays and reporter gene assays. In one embodiment, the activity of PRLR may be measured by measurement of one or more event downstream of PRLR signalling, such phosphorylation of one or more molecule, could be used. In one particular example, methods involving immunoprecipitation with a PRLR antibody followed by Western blot or ELISA measuring tyrosine phosphorylation of JAK2 (Janus Kinase 2) and/or other phosphorylated molecules downstream of PRLR signalling could be used. By way of further example, the methods described in Perot-Applanat et al, 1997, Mol Endo 11(8), could be used.

The level of PRLR (including reference to one or more fragment, precursor and/or isoform) activity in a sample and any differences therein versus a standard may be compared using standard technology having regard to the method employed to detect the activity. For example, colorimetric and fluorometric techniques may be used in which a detection molecule (such as an antibody or nucleic acid probe or primer) is labelled with a molecule which can be visualised by the naked eye or otherwise detected using a spectrophotometer, or fluorometer for example. Alternatively, detection molecules could be labelled with radio-isotopes. However, by way of example the methodology described in Perot-Applanat et al, 1997 Mol Endo 11(8) may be used.

It should be appreciated that in addition to analysing samples and standards, the methods of the invention may include the testing of one or more positive or negative control samples to ensure the integrity of the results. For example, one could include a sample containing no protein and one or more samples containing a protein with a known level of activity so that results can be calibrated across different runs of the method.

A sample may be processed prior to analysing PRLR (including reference to one or more isoform, precursor and/or fragment) activity. Skilled persons will readily appreciate appropriate processing steps and techniques suitable for performing them.

In one embodiment, high abundance proteins which have the potential to make it difficult to analyse, such as detect and/or measure the level of activity of PRLR (including reference to one or more isoform, precursor and/or fragment) may be removed from the sample. For example, Top6 or Top7 depletion may be used. By way of further example, immunoprecipitation of the protein of interest could also be used.

Processing steps for preparing the sample for analysis of PRLR (including reference to one or more isoform, precursor and/or fragment) activity may include cell lysis, immunoprecipitation and preparation of cell membranes, for example. Persons skilled in the art will readily appreciate other useful techniques that may be used.

Skilled persons may readily appreciate other means by which the sample may be processed for use in the invention.

Breeding and Cloning

As mentioned herein before, the invention provides methods for breeding animals. Various methods of the invention (such as those used to determine whether or not an animal is more likely than not to have an increased tolerance to heat, an increased resistance to ticks, and/or a desirable coat texture and methods for selecting animals (including selecting their gametes, for example) can be used to identify animals (or gametes, for example) of use in the breeding methods. Such methods may comprise identifying at least one first animal that has or is inferred to be more likely than not to have an increased tolerance to heat, an increased resistance to ticks, and/or a desirable coat texture (using one or more method as described herein) and mating said animal with a second animal. In one embodiment, the method may comprise further identifying at least one second animal that has or is inferred to be more likely than not to have an increased tolerance to heat, an increased resistance to ticks, and/or a desirable coat texture and mating said at least second animal with the at least one first animal. For example, a method may comprise selecting a first animal (and optionally also a second animal) identified to have one or more biological marker as described herein. In a preferred embodiment, the mating will produce one or more offspring.

The invention also encompasses breeding methods which comprise: 1) selecting a first gamete and/or a second gamete and fusing said first gamete with said second gamete to form a zygote; 2) selecting an embryo. The invention also provides a method of cloning an animal, comprising selecting one or more cell using a method of the invention. One or more methods of the invention (such as those for selecting or rejecting one or more cell or embryo) may be used to identify and select appropriate gametes and embryos for these breeding methods. For example, a method of these embodiments of the invention may comprise selecting a gamete, embryo or cell identified to have one or more biological marker as described herein.

In the breeding methods of the invention, animals may be mated using any appropriate methods including naturally, artificial insemination or IVF. In such cases, individual gametes may be selected for use in the process. Such gametes may be selected using a method of the invention; for example, a method of the invention may be used to identify animals that are inferred to be more likely than not to have an increased tolerance to heat, an increased resistance to ticks, and/or a desirable coat texture and gametes from those animals selected for use in a breeding program or process or gametes may be tested in accordance with the invention and then selected for use in a breeding program or process. In one particular embodiment, a method of selecting or rejecting one or more animal (according to the second, tenth, eighteenth or twenty sixth aspects of the invention described herein before, for example) could be used to select the first and/or second animal and their gametes used in IVF. In another embodiment, a method of selecting or rejecting one or more cells (according to the fifth, thirteenth, twenty first or twenty ninth aspects of the invention) could be used to select a first and/or second gamete and selected gametes used in IVF. Following selection of male and female gametes, the female gamete is fertilised in vitro. At the relevant time, one or more embryo is transferred to a gestational carrier.

In one embodiment, in vitro fertilisation of a female gamete may occur and then a method of the invention used to determine whether or not an embryo has a desired genotype/phenotype and should be selected or rejected for further use in a breeding programme. This might occur where individual gametes, or animals from which they have been obtained or derived, have not been tested to determine if they are likely to have an increased tolerance to heat, an increased resistance to ticks, and/or desirable coat texture prior to fertilisation (accordingly, the invention should be taken to include methods of breeding where the first and/or second animal and/or gametes are not selected on the basis of such a test, but a resulting embryo or offspring is tested and selected). Alternatively, a method of the invention could be used where the individual gametes or animals from which they have been obtained or derived have been tested and selected on the basis of having a desirable genotype/phenotype, for quality control purposes or to double check that the resulting embryos have the same desirable genotype/phenotype.

Optionally, following mating of the animals, one or more method of the invention may be used to determine whether or not any offspring has or may be inferred to have the desired characteristics associated with PRLR as herein before described. Such testing may occur at any time during the life of the offspring, including before birth; by way of example only, testing an embryo, a foetus, amniotic fluid, placenta, maternal blood, at birth.

In certain cases, cloning may be used to generate an animal. In such cases, the method may comprise identifying at least one first animal that has or is inferred to be more likely than not to have an increased tolerance to heat, an increased resistance to ticks, and/or a desirable coat texture (using one or more method as described herein) and using the nucleus or chromatin from one or more cell of that animal in a cloning procedure (such as somatic cell nuclear transfer, chromatin transfer techniques, and embryo splitting). Such cloning methods are described, for example, in Bovine somatic cell nuclear transfer Ross P J and Cibelli, J B 2010. Methods in Molecular Biology 636: 155477. At the relevant time during the cloning procedure, one or more embryo will be transferred to a gestational carrier.

In certain embodiments, a cloning procedure may utilise a cell derived from a cell line and a method of the invention may be used to select such a cell which is, or cell line whose cells are, capable of being used to generate an animal which is more likely than not to have an increased tolerance to heat, an increased resistance to ticks, and/or a desirable coat texture. In one embodiment, the cell line may be an embryonic cell line.

One or more cell of use in cloning may be selected using a method of the invention. Following selection of one or more cells a cloning procedure can be conducted. For example, a method of the invention may be used to identify animals that are inferred to be more likely than not to have an increased tolerance to heat, an increased resistance to ticks, and/or a desirable coat texture and cells from those animals selected for use in a cloning process. Similarly, a method of the invention may be used to identify cells from a cell line which comprise one or more genetic alteration as described herein and may be of use in generating an animal which is more likely than not to have an increased tolerance to heat, an increased resistance to ticks, and/or a desirable coat texture. Methods of the fifth, tenth, fifteenth and/or twentieth aspects of the invention may be used for such purposes. Methods of the invention could also be used to identify animals whose cells could be used to generate cell lines for cloning purposes.

In one particular embodiment, a method of selecting or rejecting one or more animal (according to the second, tenth, eighteenth or twenty sixth aspects of the invention described herein before, for example) could be used to select an animal for cloning. In another embodiment, a method of selecting or rejecting one or more cells (according to the fifth, thirteenth, twenty first or twenty ninth aspects of the invention) could be used to select one or more cells of use in cloning.

Optionally, at various stages during the cloning procedure, one or more method of the invention may be used to determine whether or not any cloned animal has or may be inferred to have the desired characteristics associated with PRLR as herein before described. Such testing may occur at any time during the life of the cloned animal. By way of example only, testing of a blastocyst, an embryo, a foetus, amniotic fluid, placenta, maternal blood, at birth.

In addition, a cloning method of the invention may involve selecting desirable cells without testing those cells or the animals or cell line from which they came for the presence or absence of a biological marker associated with increased heat tolerance and/or desirable coat texture. The cloning procedure can be initiated and then a method of the invention used to determine whether an embryo, foetus or animal resulting from the cloning procedure has a relevant biological marker in accordance with the invention and an embryo, foetus or animal selected where it has a desirable genotype/phenotype.

The breeding and cloning methods of the invention may involve subjecting one or more cell, zygote, embryo and/or feotus, for example, to any one of a number of standard growth and/or gestation methods.

Forming a Herd

The invention also provides methods for forming a herd of animals. Such methods may comprise determining whether or not an animal carries a biological marker linked to increased tolerance to heat, an increased resistance to ticks, and/or a desirable coat texture according to the thirty sixth or thirty eighth aspect of the invention described herein, determining whether or not an animal (and/or its offspring) is more likely than not to have an increased tolerance to heat, an increased resistance to ticks, and/or a desirable coat texture according to the first, ninth, seventeenth, and/or twenty fifth aspects of the invention described herein, selecting or rejecting an animal according to the second, tenth, eighteenth and/or twenty sixth aspects of the invention as described herein, and/or estimating the worth of an animal according to the third, eleventh, ninteenth and/or twenty seventh aspects of the invention as described herein, for example. In certain embodiments, methods of the invention which involve selecting or rejecting one or more cells may also be used to select one or more animals for inclusion in a herd. Animals may be selected or rejected for inclusion in the herd based on the results of one or more of the aforementioned methods of the invention. In certain embodiments, where an animal is identified to have one or more biological marker in accordance with the invention or is inferred to be more likely than not to have an increased tolerance to heat, an increased resistance to ticks, and/or a desirable coat texture and/or to have a desirable "worth", it may be selected for inclusion in the herd. Where an animal is identified not to have one or more biological marker in accordance with the invention or is inferred to be more likely than not to have an increased tolerance to heat, an increased resistance to ticks, and/or desirable coat texture or inferred to have substantially limited tolerance to heat and/or an undesirable coat texture and/or not to have a desirable "worth", it may be rejected and not selected for inclusion in the herd.

In certain embodiments, animals which are homozygous for one or more biological marker in accordance with the invention are selected for inclusion in a herd, although, this may not be prefered.

Accordingly, in certain embodiments methods of this aspect of the invention involve testing one or more animals or cells in accordance with a method of any one or more of the first, second, third, fifth, ninth, tenth, eleventh, thirteenth, seventeenth, eighteenth, ninteenth, twenty first, twenty fifth, twenty sixth, twenty seventh and/or twenty ninth aspects of the invention, selecting animals having a desirable genotype/phenotype or inferred to have one or more desired characteristic or worth and forming a herd with the selected animals.

The invention should also be taken to include a herd formed by the methods described herein.

The herd of animals may be formed for any desirable reason. However, by way of example only, it may desirable to form a herd for: beef farming; milk production; meat production; egg production; and/or fur, hair, wool, skin, or feather production.

Gene Editing Methods

As noted herein before, the identification by the inventors that an alteration in the PRLR gene is associated with desirable coat texture and heat tolerance also allows for generation of animals having such desirable phenotypes using cloning and/or gene editing processes in which one or more genetic alteration is introduced into the PRLR gene. For example, one or more specific alteration may be introduced into one or more cells that may be used to generate an animal. Accordingly, the invention provides one or more cell into which one or more specification alteration has been introduced in accordance with the invention.

The genetic alteration introduced into the PRLR gene may be of any nature, including insertion of one or more nucleotide, deletion of one or more nucleotide, and/or substitution of one or more nucleotide. In one embodiment, the one or more genetic alteration is one which increases the activity of PRLR. In one embodiment, the one or more genetic alteration includes a genetic alteration at a position corresponding to position 39136559 on chromosome 20 of *Bos Taurus*. In one embodiment, the one or more genetic alteration includes a deletion of a C at the position corresponding to position 39136559 on chromosome 20 of *Bos Taurus*. In other embodiments, the one or more genetic alteration is as described herein before.

In one embodiment, the one or more cell used to generate an animal includes individual gametes, zygotes, embryos, somatic cells, cells from a cell line, for example. In one embodiment, where IVF is used, one or more genetic alteration may be introduced into one or more gamete or zygote, for example. In one embodiment, where cloning is used, one or more genetic alteration may be introduced into one or more somatic cell or cell from a cell line, for example.

Such methods may further comprise testing or screening one or more cell, embryo, or animal after a gene editing step to ensure they include the desired genetic alteration and that it may be inferred that an animal generated by the process will be more likely than not to have an increased tolerance to heat, an increased resistance to ticks, and/or a desirable coat texture.

Any one of a number of standard methods may be used to introduce one or more genetic alteration to the PRLR gene in accordance with the invention. However, by way of example, TALEN or CRISPR methods may be used. With CRISPR, embryo genomes can be directly modified by injection of Cas9 mRNA and sgRNA into the fertilised egg resulting in the efficient production of animals carrying biallelic mutations in a given gene, for example. Such techniques are described for example in: Precision Editing of Large Animal Genomes, Wenfang (Spring) Tan, Daniel F. Carlson, Mark W. Walton, Scott C. Fahrenkrug and Perry B. Hackett, Adv Genet. 2012; 80: 37-97. doi:10.1016/B978-0-12-404742-6.00002-8; and, One-Step Generation of Mice Carrying Mutations in Multiple Genes by CRISPR/Cas-Mediated Genome Engineering, Haoyi Wang, Hui Yang, Chikdu S. Shivalila, Meelad M. Dawlaty, Albert W. Cheng, Feng Zhang, and Rudolf Jaenisch. *Cell*. 2013 May 9; 153(4): 910-918. doi:10.1016/j.cell.2013.04.025.

In one embodiment, the breeding method may involve IVF. In this example, one may first chose individual male and female gametes based on their genetic merit or otherwise, conduct gene editing methods on one or both gametes to introduce at least one desired alteration into the PRLR gene, and fertilise the female gamete in vitro. Alternatively, individual male and female gametes may be chosen, the female gamete fertilised in vitro, and then a gene editing method conducted on the fertilised zygote to introduce at least one desired alteration into the PRLR gene. It should be appreciated that one or more other alteration could also be introduced into the genome of a gamete or zygote. At the relevant time, one or more embryo may be transferred to a gestational carrier.

The methods of this embodiment may optionally comprise conducting a method of the invention described herein before to determine whether or not any cell or animal has a desired alteration and it can be inferred that the animal will be more likely to have an increased tolerance to heat, an increased resistance to ticks, and/or desirable coat texture. Such testing may occur at any time during the process and life of any animal. By way of example testing of a blastocyst, an embryo, a foetus, amniotic fluid, placenta, maternal blood, at birth. In one embodiment, an embryo is tested prior to transferring to the gestational carrier. In another embodiment, the animal is tested at birth.

In one embodiment, gene editing is combined with cloning. In this example, one may first chose an animal for use in cloning based on its genetic merit or otherwise. A cell from the animal may be subject to gene editing methods to introduce at least one desired alteration into the PRLR gene. The nucleus from such cell may then be used in known cloning processes, such as chromatin transfer, somatic cell nuclear transfer and embryo splitting. It should be appreciated that one or more other alteration could also be introduced into the genome if desired. At the relevant time, one or more embryo may be implanted into a carrier female animal for gestation.

The methods of this embodiment one may optionally comprise conducting a method of the invention described herein before to determine whether or not any cloned cell or animal has a desired alteration and it can be inferred that the animal will be more likely to have an increased tolerance to heat, an increased resistance to ticks, and/or a desirable coat texture. Such testing may occur at any time during the process and life of any animal. By way of example testing of an embryo, a foetus, amniotic fluid, placenta, maternal blood, at birth. In one embodiment, an embryo is tested prior to transferring to the gestational carrier. In another embodiment, the animal is tested at birth.

Kits

The invention also relates to kits which are of use in a method of the invention.

In one embodiment, the kit comprises at least one or more reagents suitable for analysis of one or more genetic marker in accordance with the invention. Reagents suitable for analysis of one or more of the markers include one or more nucleic acid probes and/or primers as herein described.

In another embodiment, the kit comprises at least one or more reagents suitable for detection of the level or activity of one or more of PRLR, one or more precursor thereof, one or more isoform thereof, one or more fragment thereof and/or one or more nucleic acid encoding one or more thereof.

By way of example, where an immunological procedure is used the kit may comprise one or more antibody specific to PRLR (including reference to one or more precursors, isoforms and/or fragments thereof). In a particular embodiment, ELISA is used and the kit comprises one or more capture and/or detection antibody for PRLR (including reference to one or more precursors, isoforms and/or fragments thereof).

By way of further example, where a method of the invention involves detection of the level of one or more nucleic acids encoding one or more of PRLR, one or more precursors, one or more isoforms and/or one or more fragments thereof it may comprise one or more nucleic acid probes and/or primers which have specificity for the target nucleic acid(s).

The kits may also comprise one or more standard and/or other control including one or more nucleic acid whose sequence or genotype at a particular position is known, or containing a known amount of one or more of PRLR, one or more precursor thereof, one or more isoform thereof and/or one or more fragment thereof and/or one or more nucleic acid encoding same. Further, kits of the invention can also comprise instructions for the use the components of the kit as well as printed charts or the like that could be used as standards against which results obtained from test samples could be compared. Reagents may be held in any suitable container.

EXAMPLES

Example 1

Semen from a Senepol bull was obtained from Genetic Enterprises Ltd 21 Grace Ave., Leamington, Cambridge, New Zealand. Genomic DNA was extracted from the semen using a standard phenol/chloroform extraction procedure. DNA fragments encoding the prolactin receptor were amplified using various primer pairs including those provided in Table 1 and the KAPA2G Robust PCR system (KAPA Biosystems). PCR was performed as per the manufacturer's instructions using buffer A (containing 1.5 mM Magnesium Chloride) and 25 ng genomic DNA in 50 uL reactions. PCR cycling (30 cycles per run) was performed as per the manufacturer's instructions including a temperature gradient of 55-68 degrees Celsius for the annealing step. Extension was carried out at 72 degrees Celsius for 60 seconds. PCR products were assessed with a 1% agarose/TBE gel. PCR reactions containing sufficient and clean product were sequenced by Sanger sequencing (Centre for Genomics, Proteomics and Metabolomics, The University of Auckland) using the same primers that were used for PCR amplification.

TABLE 1

| Primer name | Sequence | SEQ ID No. |
|---|---|---|
| PRLR_Final exon_F2 | CCTATTTTCTGGCCAATGGA | 1 |
| PRLR_Final exon_R2 | CAGCCCAACTGGAGTCTGC | 2 |

On analysis of the sequence data obtained, the inventors have identified a genetic alteration in the PRLR gene which has not previously been observed and appears to be unique to Senepol cattle.

This alteration is 39136559delC (located in the final exon of the gene); Table 2. The position of the alteration is read relative to the position on chromosome 20 of *Bos taurus*, build UMD3.1 (gi|1258513347|ref|AC_000177.1|) in the GenBank database http://www.ncbi.nlm.nih.gov/), as detailed herein before. The inventors have also mapped the location of the alteration in the long form PRLR gene (Table 2).

Using RNA sequencing in mammary tissue the inventors empirically determined the structure of the bovine prolactin receptor transcript. This transcript contained an additional upstream 5'UTR exon approximately 120 kb of the reference PRLR transcript (NCBI Gene ID: 281422. AC_000177.1), similar to that seen in transcript XM05221577.1 for Gene ID: 281422. The experimentally derived transcript also had a much larger 3'UTR, approximately 10 kb in length. The inventors used this updated annotation to design PCR primers and amplicons representing all PRLR exons, 5 kb of promoter sequence and the 3'UTR.

TABLE 2

| Marker | Location (within PRLR gene) | Sequence around and including alteration | SEQ ID No. |
|---|---|---|---|
| 39136559delC | Final Exon | GACCAAACAGACCAACATG (C) del TTTAAAAGCCTCAAAAACCA | 3 |

39136559delC was identified to be a frameshift mutation in the final exon of PRLR and therefore predicted to have major functional consequences to the activity of the long form of the prolactin receptor. These data suggest that this frameshift mutation may be the (or at least a) causative mutation for heat tolerance and slick coat in Senepol; while not wishing to be bound by any particular theory, the inventors contemplate that this is likely through enhanced activation of the prolactin signalling pathway.

FIGS. 1 and 2 illustrate the nucleotide (SEQ ID No. 4) and amino acid (SEQ ID No. 5) sequences of *Bos taurus* prolactin receptor (PRLR), long-form (NM_001039726.2), indicating the location of the 39136559delC. The base deletion (C) identified is at position 1466 in mRNA sequence (arrow) and genomic position 39136559. The nucleotide sequence of the gene including the deleted C at this position is provided in FIG. 3 (SEQ ID No. 6). The resulting frameshift codes for a valine followed by a stop codon resulting in protein truncation (FIG. 2). The frameshift mutation observed will result in truncation of the protein from 581 amino acids to 461 amino acids through removal of the sequence highlighted (FIG. 2) and conversion of the new carboxy terminal amino acid from alanine to valine. The truncated protein sequence is illustrated in FIG. 4 (SEQ ID no. 7). The long-form of PRLR is important for many aspects of Prolactin function.

The NCBI Reference Sequence NM_174155.2 for the short-form of PRLR results in a PRLR variant of 296 amino acids, meaning the single base deletion variant identified by the inventors is unlikely to affect the amino acid sequence of this isoform. However, the inventors believe that the deletion may also impact the function of the short isoform since the variant is still contained within the 3'UTR of this transcript.

The results obtained correlate with a mutation previously identified by the inventors and located in the prolactin hormone gene (PRL) which is associated with reduced heat tolerance and 'shaggy' coat composition phenotypes. Accordingly, the inventors believe that alterations in the PRLR gene are responsible for the short, sleek coat and increased thereto or heat tolerance of Senepol compared to other breeds of cattle. This is the first demonstration of a direct link between alterations in the PRLR gene and these phenotypes in Senepol cattle. Previously, there had been some uncertainty as to the gene involved in short, sleek coat and increased heat tolerance of these cattle, with various other genes having been proposed to be linked to the phenotype.

Example 2

The Romosinuano breed of cattle has also been reported to possess the "slick" phenotype.

Earpunch samples were taken from five Costa Rican Romosinuano cattle for PRLR genotyping. Earpunch samples were sent to GeneSeek (Lincoln, Nebr., USA) for DNA extraction and genotyping of the chr20:39136559delC PRLR variant using Sequenom iPLEX (Sequenom), targeting alleles in both forward and reverse strand orientations.

The inventors identified the chr20:39136559delC frameshift mutation in two "slick" phenotype animals of the Romosinuano breed. Both animals were heterozygous for the deletion (genotype C.Del).

These data show that the frameshift mutation identified by the inventors, which is associated with heat tolerance and slick coat, has been identified in non-Senepol cattle.

Example 3

The inventors targeted 28 crossbred cattle with Senepol ancestry, and including Red Angus and/or Tuli ancestry, for PRLR genotyping. The cattle's coats were qualitatively scored as either slick or normal.

Hair samples were sent to GeneSeek (Lincoln, Nebr., USA) for DNA extraction and genotyping of the chr20:39136559delC PRLR variant using Sequenom iPLEX (Sequenom), targeting alleles in both forward and reverse strand orientations.

Table 3 shows the genotype and phenotype information for the 28 crossbred animals with Senepol ancestry. All of the animals qualitatively classified as having slick coats showed perfect segregation with the frameshift deletion at chr20:39136559delC. All of these animals were heterozygous for the deletion (genotype C.Del) except for a single homozygote (genotype Del.Del). Seven animals not carrying the mutation (genotype CC) were qualitatively classified as having "normal coats".

TABLE 3

| Identifier | Genotype at chr20:39136559 | Coat type |
| --- | --- | --- |
| Jessi | CC | Normal |
| Wally | CC | Normal |
| Charity | Del.Del | Slick |
| Cana | C.Del | Slick |
| Blondie | C.Del | Slick |
| Faith | C.Del | Slick |
| Chi | C.Del | Slick |
| Lucy | C.Del | Slick |
| Petunia | C.Del | Slick |
| Epsilon | C.Del | Slick |
| Perky | C.Del | Slick |
| Sherry | C.Del | Slick |
| Beth | C.Del | Slick |
| Grey Bull | C.Del | Slick |
| Alpha | C.Del | Slick |
| Sally | C.Del | Slick |
| Stevie | C.Del | Slick |
| Queen | C.Del | Slick |
| Tina | C.Del | Slick |
| Chiffon | C.Del | Slick |
| Dusty | C.Del | Slick |
| Kathy | C.Del | Slick |
| Berry | C.Del | Slick |
| Judy | CC | Normal |
| Abby | CC | Normal |
| Beta | CC | Normal |
| Tokay | CC | Normal |
| Misty | CC | Normal |

Analysis of these data in PLINK1 (version 1.07, Purcell, S. http://pngu.mgh.harvard.edu/purcell/plink) using a dominance genetic model gave a highly significant association of the frameshift deletion with coat type (P<0.00000012).

These data show that the frameshift mutation identified by the inventors is strongly associated with heat tolerance and slick coat. While not wishing to be bound by any particular theory, the inventors contemplate that this is likely through enhanced activation of the prolactin signalling pathway.

This data supports the inventors' finding that alterations in the PRLR gene are responsible for a short, sleek coat and increased thermo or heat tolerance. These traits are commonly found in the Senepol breed of cattle. The data also demonstrates a direct link between alterations in the PRLR gene and these phenotypes.

Example 4

Exome sequencing was conducted on 115 animals representing Holstein Friesian (N=10), Jersey (N=10), Angus (N=9), Belgian Blue (N=29), Brahman (N=10), Charolais (N=10), Nelore (N=10), Senepol (N=9), Simmental (N=10) and Yak (N=8) breeds.

Custom capture targeting RefSeq, Ensembl, and human paralogous genes was performed using the SureSelect Target Enrichment System (Agilent), with 101 bp paired-end sequencing conducted on the HiSeq 2000. Mean sequencing depth across exome targets was 25-40× per sample.

Restricting analysis to a 1 Mbp consensus interval reported in independent analyses of Senepol and Senepol crossbreeds, and filtering to non-reference variants that were present in all Senepol, but absent in the other breeds, yielded only the frameshift deletion at chr20:39136559delC.

These results show that the frameshift deletion identified by the inventors in the reported 'slick' consensus interval of chromosome 20 is present in "slick" phenotype Senepol cattle but not present in animals which are observed not to have a "slick" phenotype.

These data further show that the frameshift mutation identified by the inventors is strongly associated with heat tolerance and slick coat. While not wishing to be bound by any particular theory, the inventors contemplate that this is likely through enhanced activation of the prolactin signalling pathway.

This data further supports the inventors' finding that alterations in the PRLR gene are responsible for a short, sleek coat and increased thermo or heat tolerance. These traits are commonly found in the Senepol breed of cattle. The data also further demonstrates a direct link between alterations in the PRLR gene and these phenotypes.

Example 5

Production of Animals Using Gene Editing

Embryos are generated by in vitro fertilisation of eggs from a desirable (usually high genetic merit for a performance trait) dam with sperm from a desirable sire.

For the target species of farm livestock one or more genetic alteration in the PRLR gene, for example those which result in an increase in the activity of PRLR, are identified. In one example, mutations that will truncate the protein produced by the long-form of the PRLR gene to a length of 461 amino acids in cattle or truncation to an equivalent amino acid position for the target species, are identified. These mutations may consist of a single base deletion, as in the Senepol 'slick' mutation, a single base addition, or may be more complex producing a stop codon at the desired position in the PRLR gene. The one or more genetic alteration may be identified by reference to pre-existing information or knowledge (such as known genetic alterations), or by analysis of one or more animal to identify a previously unknown desirable genetic alteration.

Having identified one or more appropriate genetic change in the PRLR gene, gene editing tools will be used (such as those described in Wang et al., 2013 and Wenfang et al., 2013) to introduce the desired base change(s) to the PRLR gene in a zygote.

Once gene editing has occurred, embryos may be grown in vitro so that cells may be taken to verify that the edits are correct. Selected embryos will then be implanted in the uteri of recipient cows to carry them through to term.

This procedure in particular may enable the production of high genetic merit males which can be used for widespread inseminations to introduce the heat tolerance characteristic to a population or populations of cattle, pigs, sheep goats or chickens.

Example 6

Production of Animals Through Cloning

Cloning technology (such as described by Brophy et al., 2003. Nature Biotechnology 21, 157-162) can be used to introduce one or more desirable genetic alteration to an animal. Briefly, this will involve the introduction of the one or more desired mutation into a cell line in vitro and nuclear transfer to an enucleated oocyte.

As in example 2, embryos can be grown in vitro to enable biopsy and testing of embryos to enable selection of those carrying the desirable genotype.

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. The invention also includes all of the steps, features, compositions and compounds referred to or indicated in this specification, individually or collectively, and any and all combinations of any two or more of said steps or features. Furthermore, titles, headings, or the like are provided to enhance the reader's comprehension of this document, and should not be read as limiting the scope of the present invention.

The entire disclosures of all applications, patents and publications, cited above and below, if any, are hereby incorporated by reference. However, the reference to any applications, patents and publications in this specification is not, and should not be taken as, an acknowledgment or any form of suggestion that they constitute valid prior art or form part of the common general knowledge in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

The invention claimed is:

1. A method of selecting a variation in a prolactin receptor (PRLR) gene that results in a desirable phenotype in a non-human mammal, comprising:
   (a) obtaining a nucleic acid sample from one or a plurality of non-human mammals, non-human mammalian embryos, or non-human mammalian cells; and
   (b) detecting in the nucleic acid sample of (a) at least one of:
      (i) one or more genetic variation in the PRLR gene, and
      (ii) one or more genetic marker in linkage disequilibrium with one or more genetic variation in the PRLR gene, and therefrom selecting the variation in the PRLR gene that results in the desirable phenotype, wherein the desirable phenotype in the non-human mammal comprises at least one of an increased tolerance to heat, an increased resistance to ticks, and a desirable coat texture which comprises at least one of a thin coat, a light coat, a sleek coat, and a short coat, relative, respectively, to the tolerance to heat, the resistance to ticks, and the coat texture in a non-human mammal that does not carry the one or more genetic variation.

2. The method of claim 1, wherein the one or more genetic variation in the PRLR gene results in an increase in PRLR activity in the non-human mammal relative to PRLR activity in the non-human mammal that does not carry the one or more genetic variation.

3. The method of claim 1, wherein the genetic variation in the PRLR gene is one or more of:
   (a) a variation resulting in a truncated PRLR polypeptide;
   (b) a variation which results in truncation of a PRLR polypeptide in a region from approximately an amino acid position corresponding to position 430 to approximately an amino acid corresponding to position 490 of Bos taurus PRLR;
   (c) a variation located in a final exon of the PRLR gene;
   (d) a variation located within a region bounded by nucleotides corresponding to positions 39136469 and 39136649 of chromosome 20 of Bos taurus;
   (e) a variation at a nucleotide position corresponding to position 39136559 of chromosome 20 of Bos taurus;
   (f) a variation corresponding to a deletion of a C at a nucleotide position corresponding to position 39136559 of chromosome 20 of Bos taurus; and
   (g) one or more genetic marker in linkage disequilibrium with at least one of (a)-(f).

4. The method of claim 1 which further comprises selecting the non-human mammal, non-human mammalian embryo, or non-human mammalian cell of (a) based on its being more likely than not to have or result in the desirable phenotype, or rejecting the non-human mammal, non-human mammalian embryo, or non-human mammalian cell based on its not being more likely than not to have or result in the desirable phenotype, said method comprising at least one of:
   (c) selecting the non-human mammal, non-human mammalian embryo, or non-human mammalian cell from which the nucleic acid sample has been obtained, which mammal, embryo, or cell has been determined to carry said at least one of (i) one or more genetic variation in the PRLR gene, and (ii) one or more genetic marker in linkage disequilibrium with one or more genetic variation in the PRLR gene, wherein said genetic variation in the PRLR gene results in a desirable phenotype in a non-human mammal comprising at least one of an increased tolerance to heat, an increased resistance to ticks, and a desirable coat texture, relative, respectively, to the tolerance to heat, the resistance to ticks, and the coat texture in a non-human mammal that does not carry the one or more genetic variation, and thereby selecting the non-human mammal, non-human mammalian embryo, or non-human mammalian cell that is more likely than not to have or result in the desirable phenotype; and
   (d) rejecting the non-human mammal, non-human mammalian embryo, or non-human mammalian cell from which the nucleic acid sample has been obtained, which mammal, embryo, or cell has been determined not to carry said at least one of (i) one or more genetic variation in the PRLR gene, and (ii) one or more genetic marker in linkage disequilibrium with one or more genetic variation in the PRLR gene, wherein said genetic variation in the PRLR gene results in a desirable phenotype in a mammal comprising at least one of an increased tolerance to heat, an increased resistance to ticks, and a desirable coat texture, relative, respectively, to the tolerance to heat, the resistance to ticks, and the coat texture in a non-human mammal that does not carry the one or more genetic variation, and thereby rejecting the non-human mammal, non-human mammalian embryo, or non-human mammalian cell that is not more likely than not to have or result in the desirable phenotype.

5. The method of claim 1 which further comprises calculating an estimated economic value or worth of the non-human mammal from which the nucleic acid sample has been obtained, based on one of (i) said one or more genetic variation in the PRLR gene, or (ii) said one or more genetic marker in linkage disequilibrium with one or more genetic variation in the PRLR gene as detected in step (b).

6. The method of claim 1 which further comprises breeding non-human mammals having the desirable phenotype, said method comprising:
   (c) selecting as a first animal the non-human mammal from which the nucleic acid sample has been obtained, which first animal has been determined to carry said at least one of (i) one or more genetic variation in the PRLR gene, and (ii) one or more genetic marker in linkage disequilibrium with one or more genetic variation in the PRLR gene; and
   (d) mating the first animal of (c) to a second animal, wherein the second animal is selected from:
      (i) a randomly selected second non-human mammal, and (ii) a second animal that is a non-human mammal which has been determined, according to the method of claim 1, to carry at least one of (i) one or more genetic variation in the PRLR gene, and (ii) one or more genetic marker in linkage disequilibrium with one or more genetic variation in the PRLR gene, and thereby breeding non-human mammals having the desirable phenotype.

7. The method of claim 1 which further comprises breeding a non-human mammal having the desirable phenotype, said method comprising:
   (c) selecting the embryo from which the nucleic acid sample has been obtained, which embryo has been determined to carry said at least one of (i) one or more genetic variation in the PRLR gene, and (ii) one or more genetic marker in linkage disequilibrium with one or more genetic variation in the PRLR gene; and
   (d) transferring the embryo to a gestational carrier, and thereby breeding a non-human mammal having the desirable phenotype.

8. The method of claim 1 which further comprises cloning animal non-human mammal having the desirable phenotype, said method comprising:
   (c) selecting the embryo from which the nucleic acid sample has been obtained, which embryo has been determined to carry said at least one of (i) one or more genetic variation in the PRLR gene, and (ii) one or more genetic marker in linkage disequilibrium with one or more genetic variation in the PRLR gene, to obtain a selected embryo; and
   (d) splitting by an embryo splitting technique the selected embryo of (c) to obtain a part of an embryo that is capable of being transferred to a gestational carrier, and thereby cloning animal non-human mammal having the desirable phenotype.

9. The method of claim 1 which further comprises:
   (c) selecting the plurality of non-human mammals from which the nucleic acid sample has been obtained, which non-human mammals have been determined to carry said at least one of (i) one or more genetic variation in the PRLR gene, and (ii) one or more genetic marker in linkage disequilibrium with one or more genetic variation in the PRLR gene, thereby to obtain selected non-human mammals;
   (d) rejecting the plurality of non-human mammals from which the nucleic acid sample has been obtained, which non-human mammals have been determined not to carry said at least one of (i) one or more genetic variation in the PRLR gene, and (ii) one or more genetic marker in linkage disequilibrium with one or more genetic variation in the PRLR gene, thereby to obtain rejected non-human mammals; and
   (e) forming a herd of the selected non-human mammals of (c) and excluding from the herd the rejected non-human mammals of (d), thereby to form a herd of non-human mammals more likely than not to have the desirable phenotype.

10. A method of selecting a variation in a prolactin receptor (PRLR) gene that results in an increase in PRLR activity in a non-human mammal relative to PRLR activity in non-human mammal that does not carry the one or more genetic variation, comprising:
    (a) obtaining a nucleic acid sample from one or a plurality of non-human mammalian animals, embryos, or cells; and
    (b) detecting in the nucleic acid sample of (a) at least one of:
        (i) one or more genetic variation in the PRLR gene, which genetic variation is associated with at least one of an increased tolerance to heat, an increased resistance to ticks, and a desirable coat texture which comprises at least one of a thin coat, a light coat, a sleek coat, and a short coat, relative, respectively, to the tolerance to heat, the resistance to ticks, and the coat texture in non-human mammal that does not carry the one or more genetic variation, and
        (ii) one or more genetic marker in linkage disequilibrium with the one or more genetic variation in the PRLR gene, which genetic variation is associated with at least one of an increased tolerance to heat, an increased resistance to ticks, and a desirable coat texture which comprises at least one of a thin coat, a light coat, a sleek coat, and a short coat, relative, respectively, to the tolerance to heat, the resistance to ticks, and the coat texture in non-human mammal that does not carry the one or more genetic variation,
    and thereby selecting the variation in the PRLR gene that results in the increase in PRLR activity in the non-human mammal, wherein the increase in PRLR activity is associated with a desirable phenotype.

11. The method of claim 10, wherein the desirable phenotype in the non-human mammal comprises at least one of an increased tolerance to heat, an increased resistance to ticks, and a desirable coat texture, relative, respectively, to the tolerance to heat, the resistance to ticks, and the coat texture in non-human mammal that does not carry the one or more genetic variation.

12. The method of claim 10, wherein the genetic variation in the PRLR gene is one or more of:
    (a) a variation resulting in a truncated PRLR polypeptide;
    (b) a variation which results in truncation of a PRLR polypeptide in a region from approximately an amino acid position corresponding to position 430 to approximately an amino acid corresponding to position 490 of *Bos taurus* PRLR;
    (c) a variation located in a final exon of the PRLR gene;
    (d) a variation located within a region bounded by nucleotides corresponding to positions 39136469 and 39136649 of chromosome 20 of *Bos taurus;*
    (e) a variation at a nucleotide position corresponding to position 39136559 of chromosome 20 of *Bos taurus;*
    (f) a variation corresponding to a deletion of a C at a nucleotide position corresponding to position 39136559 of chromosome 20 of *Bos taurus*; and
    (g) one or more genetic marker in linkage disequilibrium with at least one of (a)-(f).

13. The method of claim 10 which further comprises selecting or rejecting the non-human mammalian animal, embryo, or cell based on its being more likely than not to have the variation in the PRLR gene that results in the desirable phenotype, said method comprising at least one of:
    (c) selecting the non-human mammalian animal, embryo, or cell from which the nucleic acid sample has been obtained, which animal, embryo, or cell has been determined to carry said at least one of (i) one or more genetic variation in the PRLR gene, and (ii) one or more genetic marker in linkage disequilibrium with one or more genetic variation in the PRLR gene, thereby to obtain selected animals, embryos, or cells; and
    (d) rejecting the animal, embryo, or cell from which the nucleic acid sample has been obtained, which animal, embryo, or cell has been determined not to carry said at least one of (i) one or more genetic variation in the PRLR gene, and (ii) one or more genetic marker in linkage disequilibrium with one or more genetic variation in the PRLR gene, thereby to obtain rejected animals, embryos, or cells.

14. The method of claim 10, wherein the one or plurality of non-human mammalian cells comprises a first gamete, the method further comprising:
    (c) selecting the cell or plurality of cells from which the nucleic acid sample has been obtained, which cells have been determined to carry said at least one of (i) one or more genetic variation in the PRLR gene, and (ii) one or more genetic marker in linkage disequilibrium with one or more genetic variation in the PRLR gene, thereby to obtain selected cells comprising a first gamete containing a variation in the PRLR gene that results in the desirable phenotype; and
    (d) fusing said first gamete with a second gamete by in vitro fertilization.

15. The method of claim 10, wherein the one or plurality of non-human mammalian animals, embryos, or cells comprises a somatic cell, the method further comprising:
    (c) selecting the non-human mammalian animal, embryo, cell or plurality of animals, embryos, or cells from which the nucleic acid sample has been obtained, which animals, embryos, or cells have been determined to carry said at least one of (i) one or more genetic variation in the PRLR gene, and (ii) one or more genetic marker in linkage disequilibrium with one or more genetic variation in the PRLR gene, thereby to obtain selected non-human mammalian animals, embryos, or cells comprising a somatic cell nucleus containing a variation in the PRLR gene that results in the desirable phenotype; and
    (d) cloning non-human mammalian animal by somatic cell nuclear transfer of the somatic cell nucleus of (c) into an enucleated oocyte to form a reconstituted oocyte that is capable of being transferred to a gestational carrier, and thereby cloning non-human mammalian animal having the desirable phenotype.

16. The method of claim 10, wherein the one or plurality of non-human mammalian animals, embryos, or cells comprises a somatic cell, the method further comprising:
    (c) selecting the non-human mammalian animal, embryo, or cell or plurality of animals, embryos, or cells from which the nucleic acid sample has been obtained, which animals, embryos, or cells have been determined to carry said at least one of (i) one or more genetic variation in the PRLR gene, and (ii) one or more genetic marker in linkage disequilibrium with one or more genetic variation in the PRLR gene, thereby to obtain selected somatic cells comprising a somatic cell nucleus containing a variation in the PRLR gene that results in the desirable phenotype; and
    (d) cloning non-human mammalian animal by chromatin transfer from the somatic cell nucleus of (c) via fusion of the somatic cell to an enucleated oocyte to form a reconstituted oocyte that is capable of being transferred to a gestational carrier, and thereby cloning a non-human mammalian animal having the desirable phenotype.

17. A method of selecting a variation in a prolactin receptor (PRLR) gene that results in a desirable phenotype in a non-human mammal, comprising:
    (A) obtaining a nucleic acid sample from one or a plurality of non-human mammalian animals, embryos, or cells; and
    (B) detecting in the nucleic acid sample of (A) at least one genetic variation in the PRLR gene that is selected from:
        (1) a variation at a nucleotide position corresponding to position 39136559 of chromosome 20 of *Bos taurus,* and
        (2) a variation corresponding to a deletion of a C at a nucleotide position corresponding to position 39136559 of chromosome 20 of *Bos taurus,* and therefrom selecting the variation in the PRLR gene that results in the desirable phenotype;
    wherein the desirable phenotype in the non-human mammal comprises at least one of an increased tolerance to heat, an increased resistance to ticks, and a desirable coat texture which comprises at least one of a thin coat, a light coat, a sleek coat, and a short coat, relative, respectively, to the tolerance to heat, the resistance to ticks, and the coat texture in animal non-human mammal that does not carry the one or more genetic variation.

18. The method of claim 17 which further comprises breeding non-human mammals having the desirable phenotype, said method comprising:
    (C) selecting as a first animal the non-human mammal from which the nucleic acid sample has been obtained, which first animal has been determined to carry said at least one or more genetic variation in the PRLR gene; and
    (D) mating the first animal of (C) to a second animal, wherein the second animal is a non-human mammal selected from:
        (i) a randomly selected second animal, and
        (ii) a second animal which has been determined, according to the method of claim 17, to carry said at least one genetic variation in the PRLR gene, and thereby breeding non-human mammals having the desirable phenotype.

19. The method of claim 17 which further comprises breeding animal non-human mammal having the desirable phenotype, said method comprising:
    (C) selecting the non-human mammalian embryo from which the nucleic acid sample has been obtained, which embryo has been determined to carry said at least one genetic variation in the PRLR gene; and
    (D) transferring the embryo to a gestational carrier, and thereby breeding a non-human mammal having the desirable phenotype.

20. The method of claim 17 which further comprises cloning animal non-human mammal having the desirable phenotype, said method comprising:
    (C) selecting the non-human mammalian embryo from which the nucleic acid sample has been obtained, which embryo has been determined to carry said at least one genetic variation in the PRLR gene, to obtain a selected embryo; and
    (D) splitting by an embryo splitting technique the selected embryo of (C) to obtain a part of an embryo that is capable of being transferred to a gestational carrier, and thereby cloning animal non-human mammal having the desirable phenotype.

21. The method of claim 17 which further comprises:
    (C) selecting the plurality of non-human mammalian animals from which the nucleic acid sample has been obtained, which animals have been determined to carry said at least one genetic variation in the PRLR gene, thereby to obtain selected animals;

(D) rejecting the plurality of non-human mammalian animals from which the nucleic acid sample has been obtained, which animals have been determined not to carry said at least one genetic variation in the PRLR gene, thereby to obtain rejected animals; and (E) forming a herd of the selected animals of (C) and excluding from the herd the rejected animals of (D), thereby to form a herd of non-human mammalian animals more likely than not to have the desirable phenotype.

22. The method of claim 17 in which step (B) further comprises detecting, in the nucleic acid sample of (A), one or more genetic marker in linkage disequilibrium with one or more genetic variation in the PRLR gene.

\* \* \* \* \*

UNITED STATES PATENT AND TRADEMARK OFFICE
CERTIFICATE OF CORRECTION

PATENT NO. : 10,779,518 B2
APPLICATION NO. : 15/029124
DATED : September 22, 2020
INVENTOR(S) : Mathew Douglas Littlejohn et al.

Page 1 of 1

It is certified that error appears in the above-identified patent and that said Letters Patent is hereby corrected as shown below:

In the Claims

Column 75, Claim 8, Lines 21-22:
"cloning animal non-human mammal" should read --cloning a non-human mammal--

Column 75, Claim 8, Line 34:
"cloning animal non-human mammal" should read --cloning the non-human mammal--

Column 75, Claim 10, Line 61:
"in non-human mammal" should be: --in a non-human mammal--

Column 76, Claim 10, Line 8:
"in non-human mammal" should be: --in a non-human mammal--

Column 76, Claim 10, Line 18:
"in non-human mammal" should be: --in a non-human mammal--

Column 76, Claim 11, Line 29:
"in non-human mammal" should be: --in a non-human mammal--

Column 77, Claim 15, Line 34:
"(d) cloning non-human mammalian" should be: --(d) cloning a non-human mammalian--

Column 77, Claim 15, Line 39:
"cloning non-human mammalian" should be: --cloning a non-human mammalian--

Signed and Sealed this
Sixteenth Day of February, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 8

<210> SEQ ID NO 1
<211> LENGTH: 20
<212> TYPE: DNA
<213> ORGANISM: Bos taurus

<400> SEQUENCE: 1
cctattttct ggccaatgga                                              20

<210> SEQ ID NO 2
<211> LENGTH: 19
<212> TYPE: DNA
<213> ORGANISM: Bos taurus

<400> SEQUENCE: 2
cagcccaact ggagtctgc                                               19

<210> SEQ ID NO 3
<211> LENGTH: 39
<212> TYPE: DNA
<213> ORGANISM: Bos taurus

<400> SEQUENCE: 3
gaccaaacag accaacatgt ttaaaagcct caaaaacca                         39

<210> SEQ ID NO 4
```

-continued

<211> LENGTH: 2387
<212> TYPE: DNA
<213> ORGANISM: Bos taurus

<400> SEQUENCE: 4

| | | | | | |
|---|---|---|---|---|---|
| ggcaaatgct | gaggatactt | tccaagtgaa | ccctgagtga | acctctaata | tatttatttc | 60 |
| ctgtggaaag | aggaaggagc | caacatgaag | gaaaatgcag | catctagagt | ggttttcatt | 120 |
| ttgctacttt | ttctcagtgt | cagccttctg | aatggacagt | cacctcctga | aaaacccaag | 180 |
| ctcgttaaat | gtcggtctcc | tggaaaggaa | acattcacct | gctggtggga | gcctggggca | 240 |
| gatggaggac | ttcctaccaa | ttacacgctg | acttaccaca | aggaaggaga | aacactcatc | 300 |
| catgaatgtc | cagactacaa | aaccgggggc | cccaactcct | gctactttag | caagaagcac | 360 |
| acctccatat | ggaagatgta | cgtcatcaca | gtaaacgcca | tcaaccagat | gggaatcagt | 420 |
| tcctcggatc | cactttatgt | gcacgtgact | tacatagttg | aaccagagcc | tcctgcaaac | 480 |
| ctgactttgg | aattaaaaca | tccagaagat | agaaaaccat | atctatggat | aaaatggtct | 540 |
| ccacccacca | tgactgatgt | aaaatctggt | tggttcatta | tccagtacga | aattcgatta | 600 |
| aaacctgaga | agcaactga | ttgggagact | cattttactc | tgaagcaaac | tcagcttaag | 660 |
| attttcaact | tatatccagg | acaaaaatac | cttgtgcaga | ttcgctgcaa | gccagaccat | 720 |
| ggatactgga | gtgagtggag | cccagagagc | tccatccaga | tacctaatga | cttcccagtg | 780 |
| aaggacacaa | gcatgtggat | ctttgtggcc | atcctttctg | ctgtcatctg | tttgattatg | 840 |
| gtctgggcag | tggctttgaa | gggctatagc | atggtgacct | gcatcctccc | accagttcca | 900 |
| gggccaaaaa | taaaaggatt | tgatgttcat | ctgctggaga | agggcaagtc | cgaagaactt | 960 |
| ctgcgagctc | tggaaagcca | agacttcccc | cccacttctg | actgcgagga | cttgctgatg | 1020 |
| gagttcatag | aggtagatga | ctgtgaggac | cagcagctga | tgccacgccc | tccaaagaa | 1080 |
| cacacggagc | aaggcgtgaa | gcccatgcac | ctggatcttg | acagtgactc | tggccggggc | 1140 |
| agctgcgaca | gcccttcgct | cttgtctgaa | aagtgtgatg | aacctcaggc | ccatccctcc | 1200 |
| aagttccata | ctcccgaggg | ccctgagaag | ctggagaatc | cggaaacaaa | ccttacatgt | 1260 |
| ctccaggccc | ctcagagcac | aagcgtgaa | ggcaaaatcc | cctatttct | ggccaatgga | 1320 |
| cccaaatctt | ccacatggcc | tttcccgcag | cccccagcc | tatacagccc | cagatattct | 1380 |
| taccacaaca | ttgctgacgt | gtgtgagctg | gccctgggca | tggccggcac | cacagccact | 1440 |
| tcgctggacc | aaacagacca | acatgcttta | aaagcctcaa | aaaccattga | aactggcagg | 1500 |
| gaaggaaagg | caaccaagca | gagggagtca | gaaggctgca | gttccaagcc | tgaccaagac | 1560 |
| acggtgtggc | cacgaccca | agacaaaacc | cccttgatct | ctgctaaacc | cttggaatac | 1620 |
| gtggagatcc | acaaggtcag | ccaagatgga | gtgctggctc | tgttcccaaa | acaaaacgag | 1680 |
| aagtttggcg | cccctgaagc | cagcaaggag | tactcaaagg | tgtcccgggt | gacagatagc | 1740 |
| aacatcctgg | tattggtgcc | ggatccgcaa | gcgcaaaacc | tgactctgtt | agaagaacca | 1800 |
| gccaagaagg | ccccgccagc | cctgccatag | aatccagcca | aggccgacct | ggctatctcc | 1860 |
| cccacaaccc | caggcaactg | cagactccag | ttgggctggg | gactgggtcc | cgcaggtttt | 1920 |
| atgcactctt | gcagtgagag | ttatggaagg | atgggttcaa | ttgtgatttt | ccttcaggga | 1980 |
| acactacaga | gtacgtgaaa | tgcactctac | cagagagggc | tcaagaacag | ggttagaatg | 2040 |
| acactaccca | actcccagtt | cactcttaat | tctctatttt | caaccagttg | cctctttgtc | 2100 |
| caacagctga | ttccagaaca | aatcgttcca | tcttgtgtga | tttgtagatt | tacttttttg | 2160 |
| ctattagttg | tcagattata | tgttcaaaga | tataaaagca | cattgcctag | tattcttaag | 2220 |

```
agacagtgcc aataggtata taatctggaa aaggccttca tggtttcgta tgtgacagag    2280
gggtataagt cagtcaaaat tgtttaccat gggaagatgg tagataggag agaaatgcca    2340
tgaaaaccac tttgaagacc agttgcttaa cctttgcact cctcttt                  2387
```

<210> SEQ ID NO 5
<211> LENGTH: 581
<212> TYPE: PRT
<213> ORGANISM: Bos taurus

<400> SEQUENCE: 5

```
Met Lys Glu Asn Ala Ala Ser Arg Val Val Phe Ile Leu Leu Leu Phe
1               5                  10                  15

Leu Ser Val Ser Leu Leu Asn Gly Gln Ser Pro Pro Glu Lys Pro Lys
            20                  25                  30

Leu Val Lys Cys Arg Ser Pro Gly Lys Glu Thr Phe Thr Cys Trp Trp
        35                  40                  45

Glu Pro Gly Ala Asp Gly Gly Leu Pro Thr Asn Tyr Thr Leu Thr Tyr
    50                  55                  60

His Lys Glu Gly Glu Thr Leu Ile His Glu Cys Pro Asp Tyr Lys Thr
65                  70                  75                  80

Gly Gly Pro Asn Ser Cys Tyr Phe Ser Lys Lys His Thr Ser Ile Trp
                85                  90                  95

Lys Met Tyr Val Ile Thr Val Asn Ala Ile Asn Gln Met Gly Ile Ser
            100                 105                 110

Ser Ser Asp Pro Leu Tyr Val His Val Thr Tyr Ile Val Glu Pro Glu
        115                 120                 125

Pro Pro Ala Asn Leu Thr Leu Glu Leu Lys His Pro Glu Asp Arg Lys
    130                 135                 140

Pro Tyr Leu Trp Ile Lys Trp Ser Pro Pro Thr Met Thr Asp Val Lys
145                 150                 155                 160

Ser Gly Trp Phe Ile Ile Gln Tyr Glu Ile Arg Leu Lys Pro Glu Lys
                165                 170                 175

Ala Thr Asp Trp Glu Thr His Phe Thr Leu Lys Gln Thr Gln Leu Lys
            180                 185                 190

Ile Phe Asn Leu Tyr Pro Gly Gln Lys Tyr Leu Val Gln Ile Arg Cys
        195                 200                 205

Lys Pro Asp His Gly Tyr Trp Ser Glu Trp Ser Pro Glu Ser Ser Ile
    210                 215                 220

Gln Ile Pro Asn Asp Phe Pro Val Lys Asp Thr Ser Met Trp Ile Phe
225                 230                 235                 240

Val Ala Ile Leu Ser Ala Val Ile Cys Leu Ile Met Val Trp Ala Val
                245                 250                 255

Ala Leu Lys Gly Tyr Ser Met Val Thr Cys Ile Leu Pro Pro Val Pro
            260                 265                 270

Gly Pro Lys Ile Lys Gly Phe Asp Val His Leu Leu Glu Lys Gly Lys
        275                 280                 285

Ser Glu Glu Leu Leu Arg Ala Leu Glu Ser Gln Asp Phe Pro Pro Thr
    290                 295                 300

Ser Asp Cys Glu Asp Leu Leu Met Glu Phe Ile Glu Val Asp Asp Cys
305                 310                 315                 320

Glu Asp Gln Gln Leu Met Pro Arg Pro Ser Lys Glu His Thr Glu Gln
                325                 330                 335

Gly Val Lys Pro Met His Leu Asp Leu Asp Ser Asp Ser Gly Arg Gly
```

```
                340             345             350
Ser Cys Asp Ser Pro Ser Leu Leu Ser Glu Lys Cys Asp Glu Pro Gln
            355                 360                 365

Ala His Pro Ser Lys Phe His Thr Pro Glu Gly Pro Glu Lys Leu Glu
        370                 375                 380

Asn Pro Glu Thr Asn Leu Thr Cys Leu Gln Ala Pro Gln Ser Thr Ser
385                 390                 395                 400

Val Glu Gly Lys Ile Pro Tyr Phe Leu Ala Asn Gly Pro Lys Ser Ser
                405                 410                 415

Thr Trp Pro Phe Pro Gln Pro Pro Ser Leu Tyr Ser Pro Arg Tyr Ser
            420                 425                 430

Tyr His Asn Ile Ala Asp Val Cys Glu Leu Ala Leu Gly Met Ala Gly
                435                 440                 445

Thr Thr Ala Thr Ser Leu Asp Gln Thr Asp Gln His Ala Leu Lys Ala
            450                 455                 460

Ser Lys Thr Ile Glu Thr Gly Arg Glu Gly Lys Ala Thr Lys Gln Arg
465                 470                 475                 480

Glu Ser Glu Gly Cys Ser Ser Lys Pro Asp Gln Asp Thr Val Trp Pro
                485                 490                 495

Arg Pro Gln Asp Lys Thr Pro Leu Ile Ser Ala Lys Pro Leu Glu Tyr
            500                 505                 510

Val Glu Ile His Lys Val Ser Gln Asp Gly Val Leu Ala Leu Phe Pro
            515                 520                 525

Lys Gln Asn Glu Lys Phe Gly Ala Pro Glu Ala Ser Lys Glu Tyr Ser
            530                 535                 540

Lys Val Ser Arg Val Thr Asp Ser Asn Ile Leu Val Leu Val Pro Asp
545                 550                 555                 560

Pro Gln Ala Gln Asn Leu Thr Leu Leu Glu Pro Ala Lys Lys Ala
                565                 570                 575

Pro Pro Ala Leu Pro
            580

<210> SEQ ID NO 6
<211> LENGTH: 2386
<212> TYPE: DNA
<213> ORGANISM: Bos taurus

<400> SEQUENCE: 6
ggcaaatgct gaggatactt tccaagtgaa ccctgagtga acctctaata tatttatttc      60
ctgtggaaag aggaaggagc aacatgaag gaaaatgcag catctagagt ggttttcatt     120
ttgctacttt ttctcagtgt cagccttctg aatggacagt caccctcctga aaacccaag    180
ctcgttaaat gtcggtctcc tggaaaggaa acattcacct gctggtggga gcctggggca    240
gatggaggac ttcctaccaa ttacacgctg acttaccaca aggaaggaga aacactcatc    300
catgaatgtc cagactacaa aaccgggggc cccaactcct gctactttag caagaagcac    360
acctccatat ggaagatgta cgtcatcaca gtaaacgcca tcaaccagat gggaatcagt    420
tcctcggatc cactttatgt gcacgtgact tacatagttg aaccagagcc tcctgcaaac    480
ctgactttgg aattaaaaca tccagaagat agaaaaccat atctatggat aaaatggtct    540
ccacccacca tgactgatgt aaaatctggt tggttcatta ccagtacga aattcgatta    600
aaacctgaga agcaactga ttgggagact cattttactc tgaagcaaac tcagcttaag    660
attttcaact tatatccagg acaaaaatac cttgtgcaga ttcgctgcaa gccagaccat    720
```

```
ggatactgga gtgagtggag cccagagagc tccatccaga tacctaatga cttcccagtg    780
aaggacacaa gcatgtggat ctttgtggcc atcctttctg ctgtcatctg tttgattatg    840
gtctgggcag tggctttgaa gggctatagc atggtgacct gcatcctccc accagttcca    900
gggccaaaaa taaaaggatt tgatgttcat ctgctggaga agggcaagtc cgaagaactt    960
ctgcgagctc tggaaagcca agacttcccc cccacttctg actgcgagga cttgctgatg   1020
gagttcatag aggtagatga ctgtgaggac cagcagctga tgccacgccc tccaaagaa    1080
cacacggagc aaggcgtgaa gcccatgcac ctggatcttg acagtgactc tggccggggc   1140
agctgcgaca gcccttcgct cttgtctgaa aagtgtgatg aacctcaggc ccatccctcc   1200
aagttccata ctcccgaggg ccctgagaag ctggagaatc cggaaacaaa ccttacatgt   1260
ctccaggccc ctcagagcac aagcgtggaa ggcaaaatcc cctatttcct ggccaatgga   1320
cccaaatctt ccacatggcc tttcccgcag ccccccagcc tatacagccc cagatattct   1380
taccacaaca ttgctgacgt gtgtgagctg ccctgggca tggccggcac cacagccact   1440
tcgctggacc aaacagacca acatgtttaa aagcctcaaa aaccattgaa actggcaggg   1500
aaggaaaggc aaccaagcag agggagtcag aaggctgcag ttccaagcct gaccaagaca   1560
cggtgtggcc acgaccccaa gacaaaaccc ccttgatctc tgctaaaccc ttggaatacg   1620
tggagatcca caaggtcagc caagatggag tgctggctct gttcccaaaa caaaacgaga   1680
agtttggcgc ccctgaagcc agcaaggagt actcaaaggt gtcccgggtg acagatagca   1740
acatcctggt attggtgccg atccgcaag cgcaaaacct gactctgtta aagaaccag    1800
ccaagaaggc cccgccagcc ctgccataga atccagccaa ggccgacctg gctatctccc   1860
ccacaacccc aggcaactgc agactccagt tgggctgggg actgggtccc gcaggtttta   1920
tgcactcttg cagtgagagt tatggaagga tgggttcaat tgtgattttc cttcagggaa   1980
cactacagag tacgtgaaat gcactctacc agagagggct caagaacagg gttagaatga   2040
cactacccaa ctcccagttc actcttaatt ctctattttc aaccagttgc ctctttgtcc   2100
aacagctgat tccagaacaa atcgttccat cttgtgtgat ttgtagattt actttttttgc   2160
tattagttgt cagattatat gttcaaagat ataaaagcac attgcctagt attcttaaga   2220
gacagtgcca ataggtatat aatctggaaa aggccttcat ggtttcgtat gtgacagagg   2280
ggtataagtc agtcaaaatt gtttaccatg ggaagatggt agataggaga gaaatgccat   2340
gaaaaccact ttgaagacca gttgcttaac ctttgcactc ctcttt                  2386
```

<210> SEQ ID NO 7
<211> LENGTH: 461
<212> TYPE: PRT
<213> ORGANISM: Bos taurus

<400> SEQUENCE: 7

```
Met Lys Glu Asn Ala Ala Ser Arg Val Val Phe Ile Leu Leu Leu Phe
1               5                   10                  15

Leu Ser Val Ser Leu Leu Asn Gly Gln Ser Pro Glu Lys Pro Lys
            20                  25                  30

Leu Val Lys Cys Arg Ser Pro Gly Lys Glu Thr Phe Thr Cys Trp Trp
        35                  40                  45

Glu Pro Gly Ala Asp Gly Gly Leu Pro Thr Asn Tyr Thr Leu Thr Tyr
    50                  55                  60

His Lys Glu Gly Glu Thr Leu Ile His Glu Cys Pro Asp Tyr Lys Thr
65                  70                  75                  80
```

| | | | | | | | | | | | | |
|---|---|---|---|---|---|---|---|---|---|---|---|---|
| Gly | Gly | Pro | Asn | Ser | Cys | Tyr | Phe | Ser | Lys | Lys | His | Thr | Ser | Ile | Trp |
| | | | | 85 | | | | 90 | | | | 95 | | | |
| Lys | Met | Tyr | Val | Ile | Thr | Val | Asn | Ala | Ile | Asn | Gln | Met | Gly | Ile | Ser |
| | | | 100 | | | | | 105 | | | | | 110 | | |
| Ser | Ser | Asp | Pro | Leu | Tyr | Val | His | Val | Thr | Tyr | Ile | Val | Glu | Pro | Glu |
| | | | 115 | | | | | 120 | | | | | 125 | | |
| Pro | Pro | Ala | Asn | Leu | Thr | Leu | Glu | Leu | Lys | His | Pro | Glu | Asp | Arg | Lys |
| | 130 | | | | | 135 | | | | | 140 | | | | |
| Pro | Tyr | Leu | Trp | Ile | Lys | Trp | Ser | Pro | Pro | Thr | Met | Thr | Asp | Val | Lys |
| 145 | | | | | 150 | | | | | 155 | | | | | 160 |
| Ser | Gly | Trp | Phe | Ile | Ile | Gln | Tyr | Glu | Ile | Arg | Leu | Lys | Pro | Glu | Lys |
| | | | | 165 | | | | 170 | | | | | 175 | | |
| Ala | Thr | Asp | Trp | Glu | Thr | His | Phe | Thr | Leu | Lys | Gln | Thr | Gln | Leu | Lys |
| | | | 180 | | | | | 185 | | | | | 190 | | |
| Ile | Phe | Asn | Leu | Tyr | Pro | Gly | Gln | Lys | Tyr | Leu | Val | Gln | Ile | Arg | Cys |
| | | | 195 | | | | | 200 | | | | | 205 | | |
| Lys | Pro | Asp | His | Gly | Tyr | Trp | Ser | Glu | Trp | Ser | Pro | Glu | Ser | Ser | Ile |
| | 210 | | | | | 215 | | | | | 220 | | | | |
| Gln | Ile | Pro | Asn | Asp | Phe | Pro | Val | Lys | Asp | Thr | Ser | Met | Trp | Ile | Phe |
| 225 | | | | | 230 | | | | | 235 | | | | | 240 |
| Val | Ala | Ile | Leu | Ser | Ala | Val | Ile | Cys | Leu | Ile | Met | Val | Trp | Ala | Val |
| | | | | 245 | | | | 250 | | | | | 255 | | |
| Ala | Leu | Lys | Gly | Tyr | Ser | Met | Val | Thr | Cys | Ile | Leu | Pro | Pro | Val | Pro |
| | | | | 260 | | | | 265 | | | | | 270 | | |
| Gly | Pro | Lys | Ile | Lys | Gly | Phe | Asp | Val | His | Leu | Leu | Glu | Lys | Gly | Lys |
| | | | 275 | | | | | 280 | | | | | 285 | | |
| Ser | Glu | Glu | Leu | Leu | Arg | Ala | Leu | Glu | Ser | Gln | Asp | Phe | Pro | Pro | Thr |
| | 290 | | | | | 295 | | | | | 300 | | | | |
| Ser | Asp | Cys | Glu | Asp | Leu | Leu | Met | Glu | Phe | Ile | Glu | Val | Asp | Asp | Cys |
| 305 | | | | | 310 | | | | | 315 | | | | | 320 |
| Glu | Asp | Gln | Gln | Leu | Met | Pro | Arg | Pro | Ser | Lys | Glu | His | Thr | Glu | Gln |
| | | | | 325 | | | | 330 | | | | | 335 | | |
| Gly | Val | Lys | Pro | Met | His | Leu | Asp | Leu | Asp | Ser | Asp | Ser | Gly | Arg | Gly |
| | | | 340 | | | | | 345 | | | | | 350 | | |
| Ser | Cys | Asp | Ser | Pro | Ser | Leu | Leu | Ser | Glu | Lys | Cys | Asp | Glu | Pro | Gln |
| | | 355 | | | | | 360 | | | | | 365 | | | |
| Ala | His | Pro | Ser | Lys | Phe | His | Thr | Pro | Glu | Gly | Pro | Glu | Lys | Leu | Glu |
| | 370 | | | | | 375 | | | | | 380 | | | | |
| Asn | Pro | Glu | Thr | Asn | Leu | Thr | Cys | Leu | Gln | Ala | Pro | Gln | Ser | Thr | Ser |
| 385 | | | | | 390 | | | | | 395 | | | | | 400 |
| Val | Glu | Gly | Lys | Ile | Pro | Tyr | Phe | Leu | Ala | Asn | Gly | Pro | Lys | Ser | Ser |
| | | | | 405 | | | | 410 | | | | | 415 | | |
| Thr | Trp | Pro | Phe | Pro | Gln | Pro | Ser | Leu | Tyr | Ser | Pro | Arg | Tyr | Ser |
| | | | 420 | | | | | 425 | | | | | 430 | | |
| Tyr | His | Asn | Ile | Ala | Asp | Val | Cys | Glu | Leu | Ala | Leu | Gly | Met | Ala | Gly |
| | | | 435 | | | | | 440 | | | | | 445 | | |
| Thr | Thr | Ala | Thr | Ser | Leu | Asp | Gln | Thr | Asp | Gln | His | Val |
| | 450 | | | | | 455 | | | | | 460 | |

<210> SEQ ID NO 8
<211> LENGTH: 2389
<212> TYPE: DNA
<213> ORGANISM: Bos taurus

<400> SEQUENCE: 8

```
cgggcaaatg ctgaggatac tttccaagtg aaccctgagt gaacctctaa tatatttatt     60
tcctgtggaa agaggaagga gccaacatga aggaaaatgc agcatctaga gtggttttca    120
ttttgctact ttttctcagt gtcagccttc tgaatggaca gtcacctcct gaaaaaccca    180
agctcgttaa atgtcggtct cctggaaagg aaacattcac ctgctggtgg gagcctgggg    240
cagatggagg acttcctacc aattacacgc tgacttacca caaggaagga gaaacactca    300
tccatgaatg tccagactac aaaaccgggg gccccaactc ctgctacttt agcaagaagc    360
acacctccat atgaagatg tacgtcatca cagtaaacgc catcaaccag atgggaatca    420
gttcctcgga tccactttat gtgcacgtga cttacatagt tgaaccagag cctcctgcaa    480
acctgacttt ggaattaaaa catccagaag atagaaaacc atatctatgg ataaaatggt    540
ctccacccac catgactgat gtaaaatctg gttggttcat tatccagtac gaaattcgat    600
taaaacctga gaaagcaact gattgggaga ctcattttac tctgaagcaa actcagctta    660
agattttcaa cttatatcca ggacaaaaat accttgtgca gattcgctgc aagccagacc    720
atggatactg gagtgagtgg agcccagaga gctccatcca gatacctaat gacttcccag    780
tgaaggacac aagcatgtgg atctttgtgg ccatcctttc tgctgtcatc tgtttgatta    840
tggtctgggc agtggctttg aagggctata gcatggtgac ctgcatcctc ccaccagttc    900
cagggccaaa aataaaagga tttgatgttc atctgctgga agggcaag tccgaagaac    960 ttctgcgagc tctggaaagc caagacttcc cccccacttc tgactgcgag acttgctga   1020 tggagttcat agaggtagat gactgtgagg accagcagct gatgccacgc ccctccaaag   1080
aacacacgga gcaaggcgtg aagcccatgc acctggatct tgacagtgac tctggccggg   1140
gcagctgcga cagcccttcg ctcttgtctg aaaagtgtga tgaacctcag gcccatcct   1200 ccaagttcca tactcccgag ggccctgaga agctggaaga tccggaaaca aaccttacat   1260
gtctccaggc ccctcagagc acaagcgtgg aaggcaaaat cccctatttt ctggccaatg   1320
gacccaaatc ttccacatgg ccttcccgc agcccccag cctatacagc ccagatatt   1380 cttaccacaa cattgctgac gtgtgtgagc tggcccctggg catggccggc accacagcca   1440
cttcgctgga ccaaacagac caacatgctt taaaagcctc aaaaaccatt gaaactggca   1500
gggaaggaaa ggcaaccaag cagagggagt cagaaggctg cagttccaag cctgaccaag   1560
acacggtgtg ccacgaccc caagacaaaa ccccccttgat ctctgctaaa cccttggaat   1620
acgtggagat ccacaaggtc agccaagatg gagtgctggc tctgttccca aaacaaaacg   1680
agaagtttgg cgcccctgaa gccagcaagg agtactcaaa ggtgtcccgg gtgacagata   1740
gcaacatcct ggtattggtg ccggatccgc aagcgcaaaa cctgactctg ttagaagaac   1800
cagccaagaa ggccccgcca gccctgccat agaatccagc caaggccgac ctggctatct   1860
cccccacaac cccaggcaac tgcagactcc agttgggctg gggactgggt cccgcaggtt   1920
ttatgcactc ttgcagtgag agttatggaa ggatgggttc aattgtgatt ttccttcagg   1980
gaacactaca gagtacgtga atgcactct accagagagg gctcaagaac agggttagaa   2040
tgacactacc caactcccag ttcactctta attctctatt ttcaaccagt tgcctctttg   2100
tccaacagct gattccagaa caaatcgttc catcttgtgt gatttgtaga tttacttttt   2160
tgctattagt tgtcagatta tatgttcaaa gatataaaag cacattgcct agtattctta   2220
```

```
agagacagtg ccaataggta tataatctgg aaaaggcctt catggtttcg tatgtgacag    2280
aggggtataa gtcagtcaaa attgtttacc atgggaagat ggtagatagg agagaaatgc    2340
catgaaaacc actttgaaga ccagttgctt aacctttgca ctcctcttt                2389
```